United States Patent
Landis et al.

(10) Patent No.: US 7,507,820 B2
(45) Date of Patent: Mar. 24, 2009

(54) DIAZAPHOSPHACYCLES

(75) Inventors: Clark R. Landis, Madison, WI (US); Wiechang Jin, Madison, WI (US); Jonathan S. Owen, Pasadena, CA (US); Thomas P. Clark, Somerville, MA (US); Ryan C. Nelson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 467 days.

(21) Appl. No.: 10/914,048

(22) Filed: Aug. 6, 2004

(65) Prior Publication Data
US 2005/0202507 A1  Sep. 15, 2005

Related U.S. Application Data

(60) Provisional application No. 60/492,879, filed on Aug. 6, 2003.

(51) Int. Cl.
C07F 9/28  (2006.01)
C07F 9/02  (2006.01)

(52) U.S. Cl. ...................................... 544/225; 544/232

(58) Field of Classification Search ................. 544/225, 544/232
See application file for complete search history.

(56) References Cited

U.S. PATENT DOCUMENTS

2003/0055254 A1   3/2003   Landis et al.

FOREIGN PATENT DOCUMENTS

WO   WO 91/17988   11/1991
WO   WO 03/010174   2/2003

OTHER PUBLICATIONS

U.S. Appl. No. 10/787,554, filed Feb. 26, 2004, Landis et al.
U.S. Appl. No. 10/787,555, filed Feb. 26, 2004, Landis et al.
Märkl, G., et al., "1.5-Diaza-3-Phospha-Cycloheptane N.N'-Bis-[Phosphinomethyl]-Ethylendiamine Mit Optisch Aktiven Seitenketten," Tetrahedron Letters, vol. 21, pp. 3467-3470 (1980); published by Pergamon Press Ltd., Oxford, Great Britain.
Märkl, G., et al., "1.2-Diaza-4-Phospha-Cyclopentane—1.5-Diaza-3.7-Diphospha-Bicyclo-[3.3.0] Octane N.N'-[Bisphosphinomethylen]-N.N'-Dimethylhydrazine 1.3-Diaza-5-Phospha-Cyclohexane," Tetrahedron Letters, vol. 22, pp. 229-232 (1981); published by Pergamon Press Ltd., Oxford, Great Britain.
Arbuzov, B. A., et al., "Synthesis and Structure of 1,5-Diaza-3,7-Diphosphacyclooctanes," Bulletin of Academy of Science of USSR, Division of Chemical Science, pp. 1672-1676 (1984); published by Plenum Publishing Corp., New York, New York translated from Izvestiya Akademii Nauk SSSR, Seriya Khimicheskaya, No. 8, pp. 1846-1850, Aug. 1983.
Alcock, N., et al., "Substrate-induced Kinetic Resolution of Racemic Biphosphines in situ for Homogeneous Catalysis," J. Chem. Soc. Chem. Commun., pp. 1532-1534 (1986); published by Royal Chemical Society, London, England.

Burk, M. J., et al., "New Electron-Rich Chiral Phosphines for Asymmetric Catalysis," Organometallics, vol. 9, pp. 2653-2655 (1990); published by the American Chemical Society, Washington, D.C.
Burk, M. J., et al., "$C_2$-Symmetric Bis(phospholanes) and Their use in Highly Enantioselective Hydrogenation Reactions," J. Am. Chem. Soc., vol. 113, pp. 8518-8519 (1991); published by American Chemical Society, Washington, D.C.
Faller, J. W., et al., "Chiral Poisoning: A Novel Strategy for Asymmetric Catalysis," J. Am. Chem. Soc., vol. 115, pp. 804-805 (1993); published by American Chemical Society, Washington, D.C.
Khairullin, V. K., et al., "Reaction of N,N'-Dibenzylidenehydrazine with Dialkyl Hydrogen Phosphites and Phosphinic and Thioglycolic Acids," Russian Journal of General Chemistry, vol. 64, No. 4, pp. 557-559 (1994); published by Plenium Publishing Corp., New York, New York.
Kacker, S., et al., "Alternating Copolymers of Functional Alkenes with Carbon Monoxide," Macromolecules, vol. 29, pp. 5852-5858 (1996); published by American Chemical Society, Washington, D.C.
Jandeleit, B., et al., "Combinatorial Materials Science and Catalysis," Angew. Chem. Int. Ed., vol. 38, pp. 2495-2532 (1999); published by Wiley-VCH Verlag GmbH, Weinheim, Germany.
Portnoy, M., et al., "Solid-Phase Synthesis of an α-Aminophosphine Library," J. Comb. Chem., vol. 3, pp. 524-527 (2001); published by American Chemical Society, Washington, D.C.
Wilhelm, H., et al., "Zur Reaktion Von Phosphoryl- Und Thiophosphorylisothiocyanaten Mit Phosphanen-Die Kristallstruktur Des $(C_6H_5O)_2P(O)$-NH-C(S)P$(C_6H_5)_2$," Phosphorus, Sulfur, and Silicon, vol. 73, pp. 81- 91 (1992); published by Gordon Breach Science Publishers S. A., United States.
Ben-Arroya, B., et al., "Addition of borane-protected secondary phosphines to imines. A route to protected mono-N-substituted-α-aminophosphines," Tetrahedron Letters, vol. 41, pp. 6143-6147 (2000); published by Pergamon Press Ltd., Oxford, Great Britain.

(Continued)

*Primary Examiner*—James O. Wilson
*Assistant Examiner*—Ebenezer Sackey
(74) *Attorney, Agent, or Firm*—Foley & Lardner LLP

(57) ABSTRACT

Diazaphosphacycles comprising compounds having the formula XI and salts of the compound are provided, wherein the variables W, T, $R^1$, $R^{14}$, and $R^{15}$ are as described herein. Transition metal catalysts incorporating such diazaphosphacycles and methods of use thereof are also disclosed. There are further provided compositions comprising diazaphosphacycles covalently attached to a solid support and methods of use thereof.

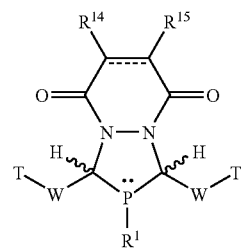

XI

44 Claims, 17 Drawing Sheets

OTHER PUBLICATIONS

Landis, C. R. et al., "Rapid Access to Diverse Arrays of Chiral 3,4-Diazaphospholanes," Agnew. Chem. Int. Ed., vol. 40, pp. 3432-3434 (2001); published by Wiley-VCH Verlag GmbH, Weinheim, Germany.

Clark, T. P. et al., "Resolved Chiral 3,4-Diazaphospholanes and Their Application to Catalytic Asymmetric Allylic Alkylation," J. Am. Chem. Soc., vol. 125, pp. 11792-11793 (2003); published by American Chemical Society.

Landis, C. R. et al., "Solid-phase synthesis of chiral 3,4-diazaphospholanes and their application to catalytic asymmetric allylic alkylation," PNAS, vol. 101, No. 15, pp. 5428-5432 (2004).

Clark et al, "Highly Active, Regioselective, and Enantioselective Hydroformylation with Rh Catalysts Ligated by Bis-3,4-diazaphospholanes," J. Am. Chem. Soc., 2005, 127, pp. 5040-5042; published by American Chemical Society.

$^1$H NMR

DIAZAPHOSPHACYCLES

CROSS-REFERENCE TO RELATED APPLICATION

This application claims priority to U.S. Application No. 60/492,879, filed Aug. 6, 2003, the entire contents of which are incorporated by reference herein and for all purposes.

GOVERNMENT RIGHTS

This invention was made with United States government support awarded by the following agency: DOE DE-FG02-99-ER14949. The United States has certain rights in this invention.

FIELD OF THE INVENTION

The invention relates generally to diazaphosphacycles and to methods for synthesizing them. The invention also relates to metal complexes that may be formed from the novel diazaphosphacycles and to their use as catalysts.

BACKGROUND OF THE INVENTION

Phosphines are used as ligands in a large number of known transition metal complexes, and phosphine ligands are included in many transition metal complexes used as catalysts. One of the reasons is that phosphines are known to be one of the best ligands for stabilizing transition metals. Phosphine ligands are often included in transition metal complexes used to catalyze hydroformylation reactions where hydrogen, an alkene, and carbon monoxide are converted to the corresponding aldehyde.

Phosphines are also included as ligands in various transition metal complexes used to catalyze hydrogenation reactions. In many of these reactions, inexpensive phosphines such as triphenylphosphine perform suitably. However, phosphines have also found a niche in more specialized areas such asymmetric hydrogenation and other catalytic transformations. The use of a chiral phosphine allows enantioselectivity in the catalytic reaction, and often high enantiomeric excesses may be achieved when a chiral phosphine is used as a ligand. The use of an enantioselective catalyst allows a desired enantiomer to be produced reducing undesired products while simultaneously reducing separation costs associated with the separation of enantiomers. Enantioselective hydrogenation catalysts may be as fast and selective as some of the best known enzymes, and such catalysts can result in greater than 99.9% production of one enantiomer.

Asymmetric hydrogenation is used to make commercially important products including biologically active compounds such as pesticides and pharmaceuticals. Asymmetric hydrogenation is being used more frequently in the pharmaceutical industry where expensive intermediate compounds are too valuable to waste. One of the first reactions employing a phosphine-containing catalyst in the pharmaceutical industry was the selective production of L-DOPA rather than R-DOPA.

As noted above, chiral phosphine ligands are central to many developments in transition metal-catalyzed enantioselective transformations. R. Noyori, *Asymmetric Catalysis*; John Wiley: New York, 1994. Recent demonstrations of high enantioselectivity for a wide range of hydrogenation reactions with Rh complexes of the DuPHOS, PennPHOS, RoPHOS, BASPHOS, CnrPHOS, and related ligands highlight the unusual efficacy of rigid phosphacycles. M. J. Burk, J. Am. Chem. Soc. 1991, 113, 8518-8519; M. J. Burk, Chemtracts-Organic Chemistry 1998, 11, 787-802; M. J. Burk, A. Pizzano, J. A. Martin, L. M. Liable-Sands, A. L. Rheingold, Organometallics 2000, 19, 250-260; M. J. Burk, F. Bienewald, S. Challenger, A. Derrick, J. A. Ramsden, J. Org. Chem. 1999, 64, 3290-3298; Z. Zhang, G. Zhu, Q. Jiang, D. Xiao, X. Zhang, J. Org. Chem. 1999, 64, 1774-1775; Q. Jiang, Y. Jiang, D. Xiao, P. Cao, X. Zhang, Angew. Chem. 1998, 110, 1100-1103; Angew. Chem., Int. Ed. Engl 1998, 37, 1100-1103; G. Zhu, P. Cao, Q. Jiang, X. Zhang, J. Am. Chem. Soc. 1997, 119, 1799-1800; Z. Chen, Q. Jiang, G. Zhu, D. Xiao, P. Cao, C. Guo, X. Zhang, J. Org. Chem. 1997, 62, 4521-4523; J. Holz, M. Quirmbach, U. Schmidt, D. Heller, R. Stürmer, A. Börner, J. Org. Chem. 1998, 63, 8031-8034; W. Li, Z. Zhang, D. Xiao, X. Zhang, J. Org. Chem. 2000, 65, 3489-3496; W. Li, Z. Zhang, D. Xiao, X. Zhang, Tetrahedron Lett. 1999, 40, 6701-6704; Y.-Y. Yan, T. V. RajanBabu, J. Org. Chem. 2000, 65, 900-906; J. Holz, D. Heller, R. Stürmer, A. Börner, Tetrahedron Lett. 1999, 40, 7059-7062; A. Marinetti, S. Jus, J.-P. Genet, Tetrahedron Lett. 1999, 40, 8365-8368; A. Marinetti, S. Jus, J.-P. Genêt, L. Ricard, Tetrahedron 2000, 56, 95-100; A. Marinetti, S. Jus, J.-P. Genêt, Tetrahedron Lett. 1999, 40, 8365-8368; A. Marinetti, S. Jus, J.-P. Genêt, L. Ricard, Tetrahedron 2000, 56, 95-100.

Although significant efforts have been made to produce transition metal complexes for effecting enantioselective catalytic transformations, one persisting problem associated with chiral phosphine ligands is that they are difficult and expensive to produce, often requiring multi-step syntheses. Both the electron density of the phosphorus atom in phosphines and the size of the phosphine ligand as expressed by cone angles are known to impact the reactivity of metal complexes prepared from them. Therefore, the ability to modify chiral phosphines and determine structure property relationships are important factors in understanding and optimizing catalytic activity. However, the difficulty associated with synthesizing chiral phosphines has prevented the synthesis of libraries of such compounds for use in analyzing structure property relationships.

One specific group of phosphines, 3,4-diazaphospholanes, are five-membered rings containing two nitrogen atoms, two carbon atoms, and a phosphorus atom as ring members. In 3,4-diazaphospholanes, each of the two carbon atom ring members is bonded to one of the ring nitrogen atoms and the ring phosphorus atom. Very few 3,4-diazaphospholanes have thus far been reported.

Märkl et al. have prepared diazaphospholanes by reacting hydrazines with phosphorus compounds having the formula $RP(CH_2OH)_2$. This synthetic methodology is limited and does not provide any simple route to compounds having groups other than H bonded to the diazaphospholane ring carbon atoms. G. Märkl, G. Y. Jin, Tetrahedron Lett. 1980, 21, 3467-3470; and G. Märkl, G. Y. Jin, Tetrahedron Lett. 1981, 22, 229-232. Arbuzov et al. have utilized the same type of methodology to prepare other diazaphosphacycles from $RP(CH_2OH)_2$. B. A. Arbuzov, O. A. Erastov, G. N. Nikonov, R. P. Arshinova, I. P. Romanova, R A. Kadyrov, Izvestia Akad, Nauk SSSR, Seriya Khimicheskaya, 1993, 8, 1846-1850. Landis discloses various 3,4-diazophospholanes in Published U.S. Application 20030055254, Ser. No. 09/911,367, which is incorporated by reference in its entirety and for all purposes as if fully set forth herein.

A need remains for chiral phosphines and methods for making them. A need also remains for transition metal complexes that include chiral phosphines and for transition metal complexes for catalyzing important reactions. A need further remains for libraries of chiral phosphines and transition metal complexes.

SUMMARY OF THE INVENTION

The present invention provides diazaphosphacycles and methods for synthesizing them. The invention also provides transition metal complexes that include diazaphosphacycles and methods for using them in catalytic transformations.

A method of synthesizing a diazaphosphacycle is provided which includes reacting a phosphine with a diimine and optionally one or more equivalents of an acid halide, a sulfonyl halide, a phosphoryl halide, or an acid anhydride in the substantial absence of $O_2$ to form the diazaphosphacycle. The phosphine has the formula I

    I.

where $R^1$ is selected from the group consisting of substituted and unsubstituted aryl groups, substituted and unsubstituted alkyl groups, substituted and unsubstituted alkenyl groups, substituted and unsubstituted cycloalkyl groups, and substituted and unsubstituted ferrocenyl groups.

Methods for synthesizing diazaphosphacycles are also provided in which the diimine has the formula II and the diazaphosphacycle formed has the formula III

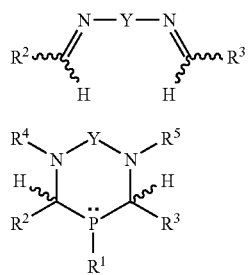

where:
$R^2$ and $R^3$ are independently selected from the group consisting of substituted and unsubstituted aryl groups, substituted and unsubstituted alkyl groups, substituted and unsubstituted cycloalkyl groups, substituted and unsubstituted heterocyclyl groups, and substituted and unsubstituted ferrocenyl groups;
$R^4$ is selected from the group consisting of —H, substituted and unsubstituted alkyl groups, substituted and unsubstituted cycloalkyl groups, substituted and unsubstituted aryl groups, trialkylsilyl groups, triarylsilyl groups, alkyldiarylsilyl groups, dialkylarylsilyl groups, —C(=O)—$R^6$ groups, —S(=O)$_2$—$R^6$ groups, —P(=O)$R^6R^7$ groups, and —C(=N$R^6$)—$R^7$ groups;
$R^5$ is selected from the group consisting of —H, substituted and unsubstituted alkyl groups, substituted and unsubstituted cycloalkyl groups, substituted and unsubstituted aryl groups, trialkylsilyl groups, triarylsilyl groups, alkyldiarylsilyl groups, dialkylarylsilyl groups, —C(=O)—$R^7$ groups, —S(=O)$_2$—$R^6$ groups, —P(=O)$R^6R^7$ groups, and —C(=N$R^6$)—$R^7$ groups;
$R^6$ is selected from the group consisting of substituted and unsubstituted alkyl groups, substituted and unsubstituted alkenyl groups, substituted and unsubstituted cycloalkyl groups, substituted and unsubstituted aryl groups, —OH groups, substituted and unsubstituted alkoxy groups, substituted and unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, and S-aryl groups;
$R^7$ is selected from the group consisting of substituted and unsubstituted alkyl groups, substituted and unsubstituted alkenyl groups, substituted and unsubstituted cycloalkyl groups, substituted and unsubstituted aryl groups, —OH groups, substituted and unsubstituted alkoxy groups, substituted and unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, and S-aryl groups;
$R^6$ and $R^7$ may be part of the same alkyl group, alkenyl group, or aryl group such that $R^4$ and $R^5$ together with the two nitrogen atoms of the diazaphosphacycle form a ring; and
Y is a linking group selected from the group consisting of substituted and unsubstituted cycloalkyl groups, substituted and unsubstituted aryl groups, substituted and unsubstituted alkenyl groups, silyl groups, substituted alkyl groups, and groups having the formula —(CH$_2$)$_n$— wherein n is selected from the group consisting of 0, 1, 2, and 3.

Some methods are provided in which n is 0. Other methods are provided in which $R^2$ and $R^3$ are identical, but are not part of the same group. Still other methods are provided in which Y is a cycloalkyl group, wherein one of the N atoms of the diimine is bonded to a first ring member C atom of the cycloalkyl group and the other N atom of the diimine is bonded to a second ring member C atom that is bonded to the first ring member C atom. Yet other methods are provided in which Y has the formula

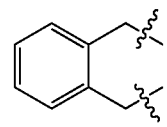

and the benzene ring of Y may be additionally substituted.

Methods are also provided in which the diazaphosphacycle is selected from compounds having the formula IIIA or IIIB or mixtures thereof

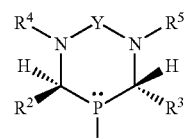    IIIA

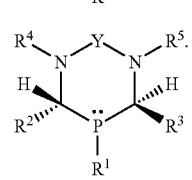    IIIB

Still other methods are provided in which the diazaphosphacycle has the formula IIIC

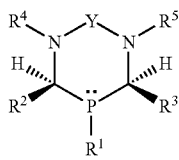

IIIC

Still other methods for synthesizing a diazaphosphacycle are provided in which the phosphine and the diimine are reacted in the presence of an acid such as hydrochloric acid or hydrobromic acid.

In still other provided methods for synthesizing a diazaphosphacycle, the phosphine and the diimine are reacted in the presence of the acid halide, the sulfonyl halide, the phosphoryl halide, or the acid anhydride, and at least one of $R^4$ and $R^5$ is not H. In still other such methods $R^4$ is a —C(=O)—$R^6$ group and $R^5$ is a —C(=O)—$R^7$ group. In still other methods in which the phosphine and the diimine are reacted in the presence of an acid halide, the acid halide is phthaloyl dichloride or phthaloyl dibromide.

Other methods for synthesizing a diazaphosphacycle are provided in which $R^1$ includes one or more —$PH_2$ group such that the phosphine is a polyphosphine. In still other such methods, the polyphosphine is selected from 1,2-diphosphinoethane, 1,2-diphosphinoethylene, 1,3-diphosphinopropane, substituted or unsubstituted 1,2-diphosphinobenzene groups, substituted or unsubstituted 1,8-diphosphinoanthracene groups, substituted or unsubstituted 1,8-diphosphino-9,10-dihydroanthracene groups, substituted or unsubstituted 1,8-diphosphinoxanthene groups, or 1,1'-diphosphinoferrocene groups.

Still other method for synthesizing diazaphosphacycles are provided in which the phosphine, the diimine, and optionally the acid halide are reacted in a substantially deoxygenated solvent such as ether, an alcohol, water, dichloroethane, or combinations of these.

Still further methods for synthesizing diazaphosphacycles are provided. These methods further include reacting an acid halide, an acid anhydride, a phosphoryl halide, or a sulfonyl halide with the diazaphosphacycle to produce a second diazaphosphacycle where $R^4$ and $R^5$ are both —H in the diazaphosphacycle and at least one of $R^4$ and $R^5$ is not —H in the second diazaphosphacycle.

In yet another provided method, the method is used to generate a library of different diazaphosphacycles such as by using a combinatorial method.

Another method for synthesizing a diazaphosphacycle is provided. The method includes reacting a diimine with an acid halide, a diacid dihalide, a sulfonyl halide, a disulfonyl dihalide, a phosphoryl halide, or a diphosphoryl dihalide to form a dihalo intermediate compound. The method further includes reacting the dihalo intermediate compound with a phosphine of formula $R^1$—$PH_2$ in the substantial absence of $O_2$ to form the diazaphosphacycle. In the method, $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups; and the diimine has the formula IV

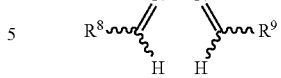

IV where $R^8$ and $R^9$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups.

Still other such methods are provided in which the diimine is reacted with a diacyl dihalide, and the diacyl dihalide has the formula V or the formula VI and the diazaphosphacycle has the formula VII or the formula VIII

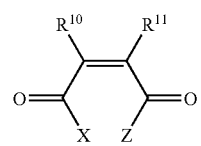

V

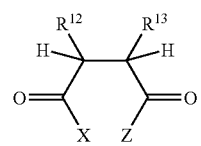

VI

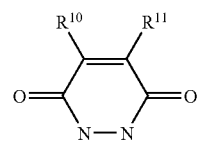

VII

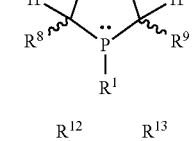

VIII

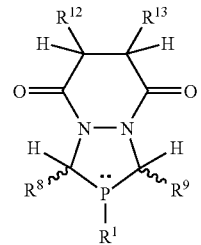

where:
$R^{10}$, $R^{11}$, $R^{12}$, and $R^{13}$ are independently selected from —H, substituted or unsubstituted alkyl groups, substituted or unsubstituted cycloalkyl groups, or substituted or unsubstituted aryl groups;

$R^{10}$ and $R^{11}$ may join together to form a substituted or unsubstituted aryl group or a substituted or unsubstituted cycloalkenyl group;

$R^{12}$ and $R^{13}$ may join together to form a substituted or unsubstituted cycloalkenyl group or a substituted or unsubstituted cycloalkyl group; and X and Z are independently selected from the group consisting of —Cl and —Br.

Other methods are provided in which $R^8$ and $R^9$ are identical but are not part of the same group and in which $R^8$ and $R^9$ are substituted or unsubstituted aryl groups.

Still other methods for synthesizing diazaphosphacycles are provided in which the diacyl dihalide is phthaloyl dichloride.

The invention further provides diazaphosphacycles having the formula III and salts of the diazaphosphacycles.

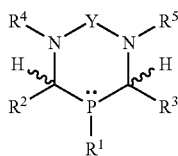

In formula III, $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups;

$R^2$ and $R^3$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups;

$R^4$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(=O)—$R^6$ groups, —S(=O)$_2$—$R^6$ groups, —P(=O)$R^6R^7$ groups, or —C(=$NR^6$)—$R^7$ groups;

$R^5$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(=O)—$R^7$ groups, —S(=O)$_2$—$R^6$ groups, —P(=O)$R^6R^7$ groups, or —C(=$NR^6$)—$R^7$ groups;

$R^6$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups;

$R^7$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups;

$R^6$ and $R^7$ may be part of the same alkyl group, alkenyl group, or aryl group such that $R^4$ and $R^5$ together with the two nitrogen atoms of the diazaphosphacycle form a ring; and Y is a linking group selected from the group consisting of substituted and unsubstituted cycloalkyl groups, substituted and unsubstituted aryl groups, substituted and unsubstituted alkenyl groups, silyl groups, substituted alkyl groups, and groups having the formula —(CH$_2$)$_n$— where n is selected from 0, 1, 2, or 3.

Still further diazaphosphacycles are provided in which n is 0. Yet other diazaphosphacycles are provided in which $R^4$ and $R^5$ are both —H. Still other diazaphosphacycles are provided in which $R^4$ is a —C(=O)—$R^6$ group and $R^5$ is a —C(=O)—$R^7$ group.

Still further diazaphosphacycles are provided which have the formula IX where $R^1$, $R^2$, and $R^3$ have any of the values set forth above and in which the benzene ring of formula IX may be substituted or unsubstituted

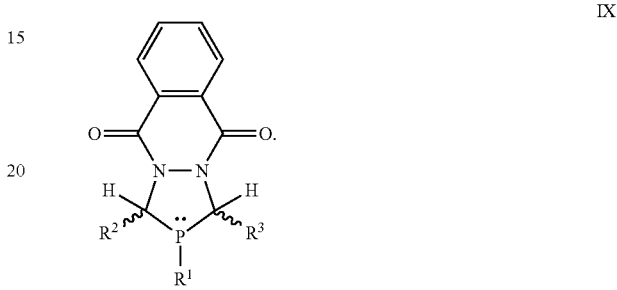

Still further diazaphosphacycles are provided that have the formula IIIA, IIIB, or IIIC as set forth above.

Still further diazaphosphacycles are provided in which the diazaphosphacycle is present as a mixture of enantiomers.

Still further diazaphosphacycles are provided in which Y is a cycloalkyl group. In some diazaphosphacycles where Y is a cycloalkyl group, one of the N atoms is bonded to a first ring member C atom of the cycloalkyl group and the other N atom is bonded to a second ring member C atom that is bonded to the first ring member C atom.

Still other diazaphosphacycles are provided in which Y has the formula

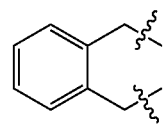

and the benzene ring of Y may be additionally substituted.

The invention further provides diazaphosphacycles having the formula X

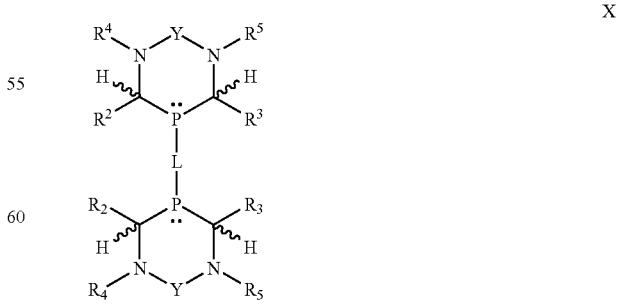

where L is a linking group selected from substituted or unsubstituted alkyl groups, substituted or unsubstituted alkenyl groups, substituted or unsubstituted aryl groups, or substituted and unsubstituted ferrocenyl groups, and the other variables have the values set forth with respect to the diazaphosphacycles of formula III set forth above. Still other such diazaphosphacycles are provided in which L is selected from ethane, ethylene, propane, benzene, anthracene, 9,10-dihydroanthracene, xanthene, or ferrocene. Transition metal complexes including these diazaphosphacycles are also provided in which at least one of the phosphorus atoms of the diazaphosphacycle is bonded to the transition metal. In other such transition metal complexes two of the phosphorus atoms of the diazaphosphacycle are bonded to the transition metal.

The invention still further provides diazaphosphacycles comprising a compound having the formula XI and salts of the compound:

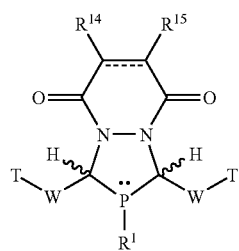

XI wherein

W, at each occurrence, is independently selected from the group consisting of aryl, cycloalkyl, and heterocyclyl groups wherein W optionally comprises one or more substituents in addition to T;

T, at each occurrence is independently selected from the group consisting of —C(O)—OR$^{16}$, —C(O)—NR$^{17}$R$^{18}$, —C(O)—N(R$^{17}$)OR$^{18}$, substituted and unsubstituted oxazole, substituted and unsubstituted oxazoline, and substituted and unsubstituted oxazolidine groups;

R$^1$ is selected from the group consisting of substituted and unsubstituted aryl, substituted and unsubstituted alkyl, substituted and unsubstituted alkenyl, substituted and unsubstituted cycloalkyl, and substituted and unsubstituted ferrocenyl groups;

R$^{14}$ and R$^{15}$ are independently selected from the group consisting of —H, substituted and unsubstituted alkyl, substituted and unsubstituted cycloalkyl, and substituted and unsubstituted aryl; or R$^{14}$ and R$^{15}$ may join together to form a substituted or unsubstituted aryl, a substituted or unsubstituted cycloalkyl, or a substituted or unsubstituted cycloalkenyl group;

R$^{16}$, R$^{17}$ and R$^{18}$ are each independently selected from the group consisting of —H, and substituted and unsubstituted alkyl, substituted and unsubstituted aryl, substituted and unsubstituted aralkyl, substituted and unsubstituted heterocyclyl, substituted and unsubstituted heterocyclylalkyl groups; or R$^{17}$ and R$^{18}$ may join together to form a non-aromatic heterocyclyl group; and the dashed line represents a single or double carbon-carbon bond.

In certain embodiments of diazaphosphacycles having formula XI, the invention provides compounds of formula XII

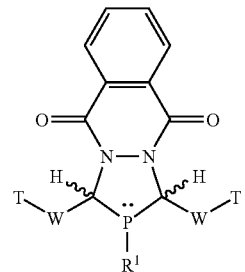

XII wherein the variables W, T, and R$^1$ are as defined above.

Particularly preferred are embodiments where diazaphosphacycles of formula XI have the formula XIII:

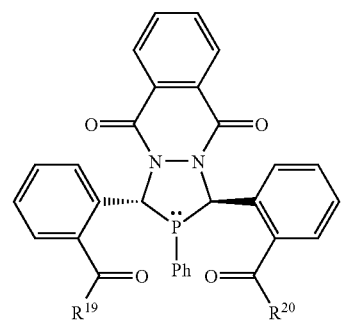

XIII wherein R$^{19}$ and R$^{20}$ are independently selected from the group consisting of substituted and unsubstituted alkyl amine, substituted and unsubstituted aralkyl amine, substituted or unsubstituted N-containing heterocyclyl, protected and unprotected amino acids, protected and unprotected amino acid esters, and protected and unprotected dipeptides; and wherein R$^{19}$ and R$^{20}$ are attached to the rest of the compound of Formula XIII through a nitrogen atom.

Still further diazaphosphacycles of formula XI are provided having the formula XIA or XIB or mixtures thereof:

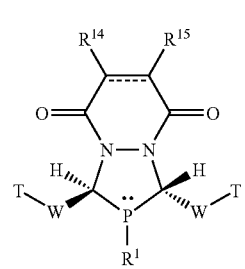

XIA

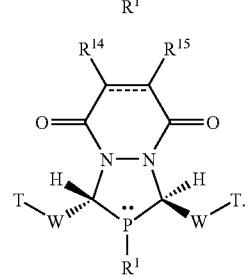

XIB

Still other diazaphosphacycles are provided that have the formula XIC:

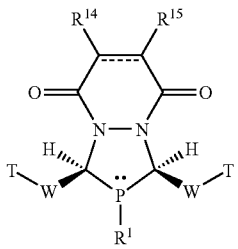

XIC

The invention further provides diazaphosphacycles of formula XI having formula XV:

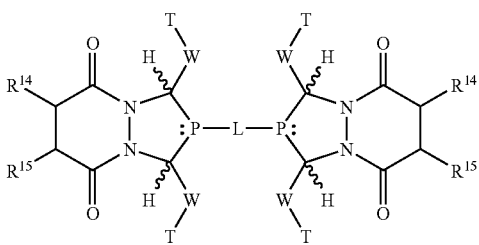

XV wherein L is a linking group selected from the group consisting of substituted and unsubstituted alkyl groups, substituted and unsubstituted alkenyl groups, substituted and unsubstituted aryl groups, and substituted and unsubstituted ferrocenyl groups.

The invention also provides a method of resolving the diazaphosphacycle of formula XI wherein T at each occurrence is —COOH, the method comprising selectively crystallizing a mixture of the diazaphosphacycle of formula XI, wherein T at each occurrence is —COOH, with either (S)- or (R)-methylbenzylamine. In some embodiments of the method of resolving the diazaphosphacycle of formula XI wherein T at each occurrence is —COOH, W at each occurrence is phenyl.

The invention further provides combinatorial libraries that include a collection of different diazaphosphacycles of the present invention. Particularly preferred are libraries that include at least one diazaphosphacycle having formula XI, XIA, XIB, XIC, XII, XIII, XIV, XIVA, XIVB, or XV. Such libraries may be made in solution or on solid phase according to procedures described herein.

The invention further provides transition metal complexes that include a diazaphosphacycle according to the invention and a transition metal where the phosphorus atom of the diazaphosphacycle is bonded to the transition metal. Transition metal complexes are further provided in which the transition metal is selected from Rh, Ru, Pd, Pt, Ir, Ni, Co, or Fe. Still other transition metal complexes are provided in which the transition metal complex has catalytic activity. A method for catalyzing a chemical reaction using a transition metal complex of the present invention as a catalyst is further provided. Furthermore, the invention provides libraries of transition metal complexes that include a collection of different transition metal complexes that include the diazaphosphacycles of the present invention.

Methods for synthesizing diazaphosphacycle transition metal complexes are further provided. The methods include reacting a diazaphosphacycle of the present invention with a starting transition metal complex to produce the diazaphosphacycle transition metal complex. The starting transition metal complex includes at least one ligand that is replaced by the diazaphosphacycle.

Other methods for synthesizing a diazaphosphacycle transition metal complex are provided in which the ligand replaced by the diazaphosphacycle is selected from phosphines; amines; diamines; CO; Cl; Br; nitriles; 1,5-cyclooctadiene, norbornadiene, and other dienes; alkenes; arenes; ketones; alcohols; ethers; thiols; or sulfoxides.

Further objects, features and advantages of the invention will be apparent from the following detailed description when taken in conjunction with the accompanying drawings.

BRIEF DESCRIPTION OF THE DRAWINGS

FIG. 9 is a $^{1}$H NMR spectrum of a Rh(NBD)(Cl) complex with compound rac-6a.

FIG. 10 is a $^{31}$P NMR spectrum ($^{1}$H coupled) of a Rh(NBD)(Cl) complex with compound rac-6a.

FIG. 15 is an X-ray crystal structure ORTEP diagram of a Rh(NBD)(Cl) complex with compound rac-6a.

DETAILED DESCRIPTION OF THE INVENTION

Figure 1:
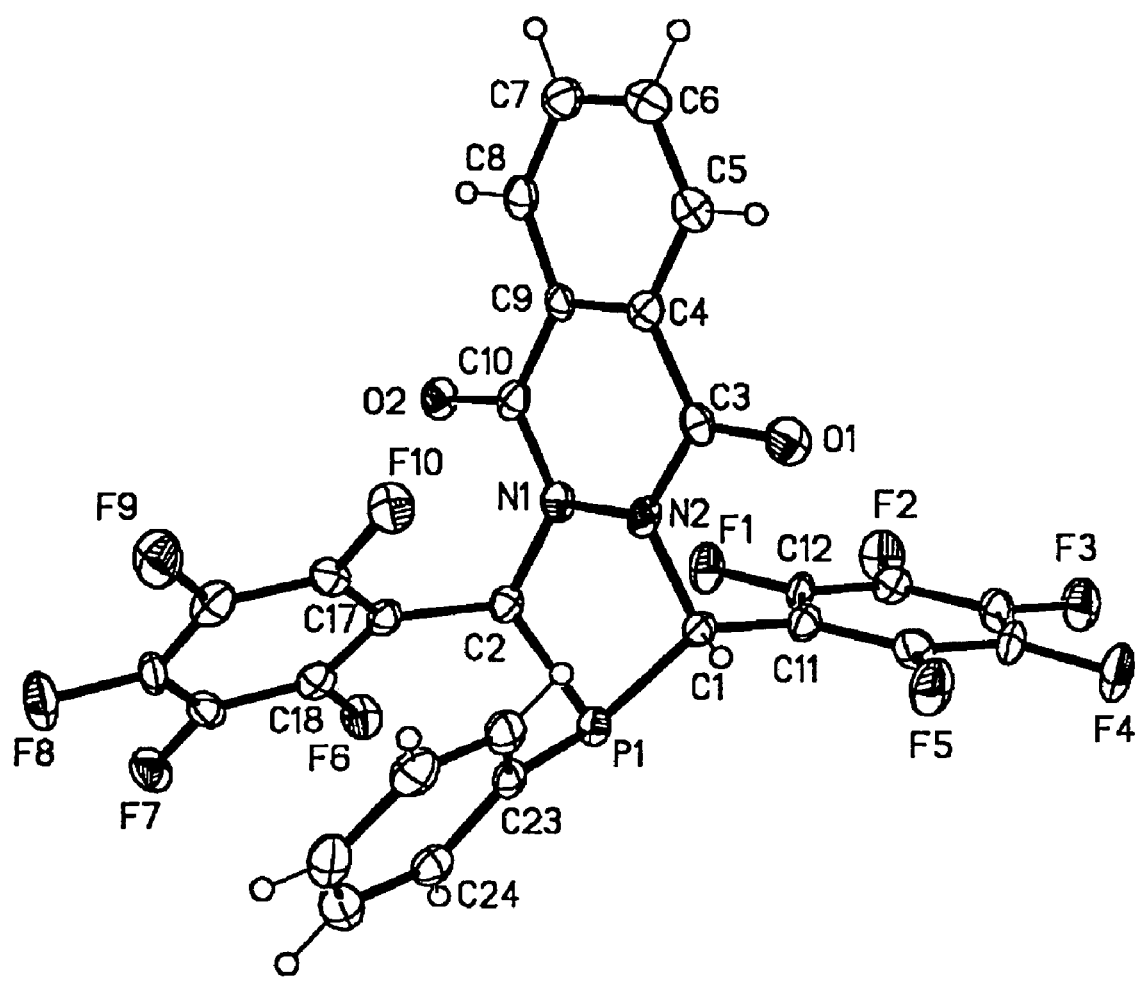
FIG. 1 is an X-ray crystal structure ORTEP diagram of rac-6e with the displacement ellipsoids drawn at the 50% probability level.
Figure 2:
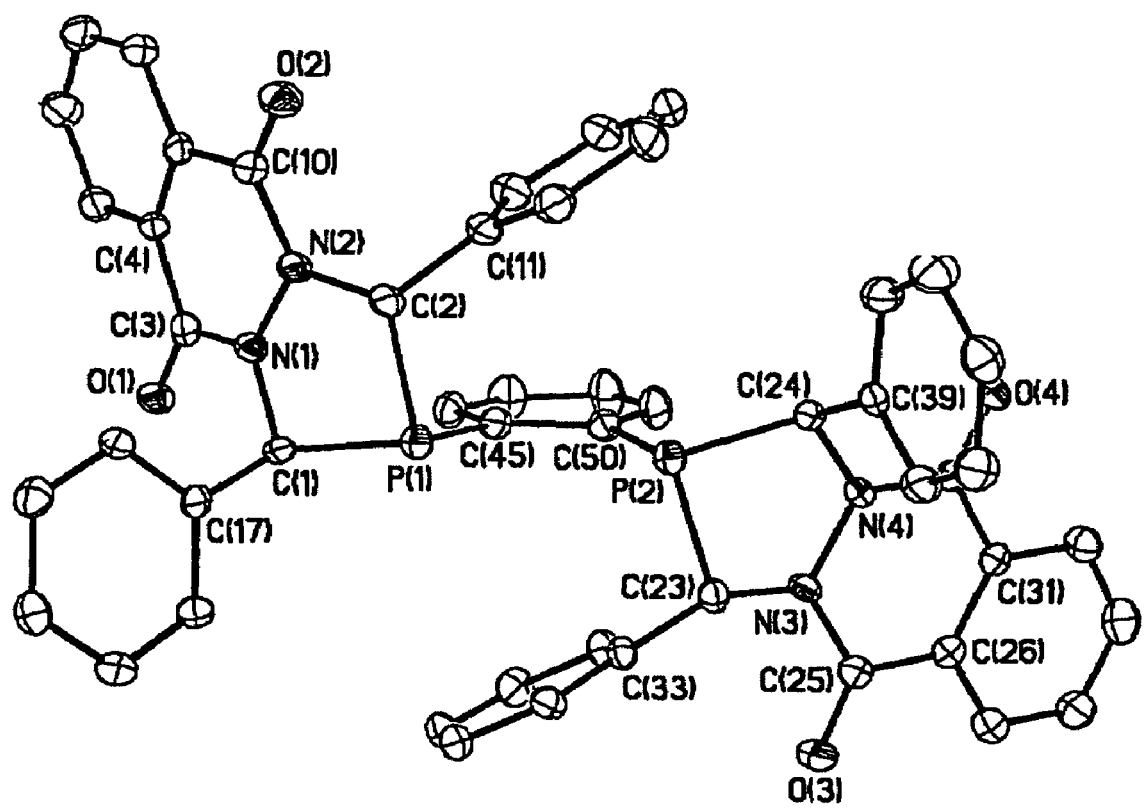
FIG. 2 is an X-ray crystal structure of rac-8. The ORTEP diagram is drawn with 30% probability ellipsoids. Solvent molecules and hydrogens have been removed for clarity.

Generally, the invention provides diazaphosphacycles such as, but not limited to, 3,4-diazaphospholanes, and methods for preparing them. The invention also generally provides transition metal complexes and methods for preparing them from diazaphosphacycles. The metal complexes have catalytic activity and are suitable for use in a wide variety of catalytic transformations such, as, but not limited to, hydrogenation and allylic alkylation reactions. The invention also provides libraries of diazaphosphacycles and transition metal complexes including diazaphosphacycles.

Variables used in the chemical formulas are understood to be used consistently throughout. For example, $R^1$ is used to refer to the same groups unless otherwise specifically noted.

The phrase "diazaphosphacycles" refers to a cyclic compound that includes one phosphorus atom and two nitrogen atoms as ring members. The phrase "diazaphospholane" refers to a five membered ring that includes one phosphorus atom and two nitrogen atom ring members. A diazaphospholane is a type of a diazaphosphacycle.

A reaction or method run in the "substantial absence of oxygen" means that the reaction is carried out using standard methodology known to those skilled in the art of working with air-sensitive compounds. This does not require the complete absence of O$_2$ only the absence of enough oxygen so that oxygen does not interfere with the desired reaction. Common procedures for performing a reaction or method in the substantial absence of oxygen include, but are not limited to the use of Schlenk techniques, the use of glove bags or glove boxes, and the use of solvents from which most, if not all, of the oxygen has been removed using standard techniques such as by bubbling an inert gas through the solvent or by freeze-pump-thaw techniques known to those skilled in the art. A reaction performed in the substantial absence of oxygen is generally conducted under an inert atmosphere such as under a N$_2$ or argon atmosphere.

Generally, a reference to a certain element such as hydrogen or H is meant to include all isotopes of that element. For example, a compound having the structure R—PH$_2$ is defined to include those compounds where one or both of the H atoms bonded to the P atom is replaced by a deuterium atom, a tritium atom, or both. An exception to the general definition that reference to a certain element is meant to include all isotopes of that element is when the element is referred to with respect to NMR spectroscopy or a deuterated solvent used in conjunction with NMR spectroscopy.

A wavy line drawn through a line in a structural formula indicates point of attachment of a group.

A wavy line drawn between an atom and a group in a structural formula indicates that a bond exists between the atom and the group, but that the position of the group is not specified. For example a wavy bond between an alkene carbon atom and a group may be used to represent cis and trans isomers, and a wavy bond from an alkyl carbon to a group indicates that no stereochemistry is assigned and the wavy bond may thus be used to represent both S and R configurations at the alkyl carbon.

The acronym "COD" refers to 1,5-cyclooctadiene.

The acronym "NBD" refers to 2,5-norbornadiene also known as bicyclo[2.2.1]hepta-2,5-diene and norbornadiene.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus, the phrase unsubstituted alkyl groups includes primary alkyl groups, secondary alkyl groups, and tertiary alkyl groups. Preferred unsubstituted alkyl groups include straight and branched chain alkyl groups having 1 to 20 carbon atoms. More preferred such unsubstituted alkyl groups have from 1 to 10 carbon atoms while even more preferred such groups have from 1 to 6 carbon atoms. Most preferred unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; a phosphorus atom in groups such as phosphines, and phosphoryls; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. Other alkyl groups include those in which one or more bonds to a carbon or hydrogen atom is replaced by a bond to an oxygen atom such that the substituted alkyl group contains a hydroxyl, alkoxy, aryloxy, or heterocyclyloxy group. Still other substituted alkyl groups include alkyl groups that have an amine group.

The phrase "unsubstituted alkenyl" refers to an "unsubstituted alkyl" group as defined above where at least one single C—C bond of the unsubstituted alkyl group is replaced by a double bond.

The phrase "substituted alkenyl" has the same meaning with respect to unsubstituted aryl groups that substituted alkyl groups has with respect to unsubstituted alkyl groups.

The phrase "unsubstituted cycloalkyl" refers to a cycloalkyl group where none of the carbon atoms of the cycloalkyl ring is bonded to an element other than H except for the carbon atom(s) bonded as the point of attachment. Examples of unsubstituted cycloalkyl groups include cyclopropyl, cyclobutyl, cyclopentyl, cyclohexyl, cycloheptyl, and cyclooctyl groups. Cyclohexyl and cyclopentyl groups are preferred cycloalkyl groups.

The phrase "substituted cycloalkyl" has the same meaning with respect to unsubstituted cycloalkyl groups that substituted alkyl groups have with respect to unsubstituted alkyl groups. However, a substituted cycloalkyl group also includes cycloalkyl groups in which one or more ring carbon atoms of the cycloalkyl group is bonded to a substituted and/or unsubstituted alkyl group. Thus, the phrase "substituted cycloalkyl" includes, but is not limited to methylcyclohexyl, and chlorocyclopentyl groups among others.

The phrase "unsubstituted aryl" refers to aryl groups that are not substituted. Thus the phrase includes, but is not limited to, groups such as phenyl, biphenyl, anthracenyl, naphthenyl, and xanthenyl by way of example. Although the phrase "unsubstituted aryl" includes groups containing condensed rings such as naphthalene, it does not include aryl groups that have other groups such as alkyl or halo groups bonded to one of the ring members as aryl groups such as tolyl are substituted aryl groups. A preferred unsubstituted aryl group is phenyl. Unsubstituted aryl groups may be bonded to one or more atom in the parent structural formula.

The phrase "substituted aryl group" has the same meaning with respect to unsubstituted aryl groups that substituted alkyl groups have with respect to unsubstituted alkyl groups. However, a substituted aryl group also includes aryl groups in which one or more aromatic carbons of the aryl group is bonded to a substituted and/or unsubstituted alkyl group. Thus, the phrase "substituted aryl" includes, but is not limited to tolyl, and hydroxyphenyl among others.

All ranges recited herein include all combinations and subcombinations included within that range's limits. For example, a temperature range of from about 20° C. to about 65° C. includes ranges of from 20° C. to 60° C., of from 25° C. to 30° C., of from 25° C. to 28° C., and of from 20° C. to 30° C., etc. Furthermore, one skilled in the art will recognize that any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third.

An acid chloride refers to a compound having at least one carboxylic acid group where the —OH group of the carboxylic acid moiety is replaced with a halogen group such as, but not limited to, —Cl or —Br. A diacid dichloride is a type of acid chloride and refers to a compound having at least two carboxylic acid groups where the —OH groups have been replaced with halogen groups. Examples of diacid dichlorides include, but are not limited to, oxalyl chloride, phthaloyl dichloride, and phthaloyl dibromide.

The term "protected" with respect to hydroxyl groups, amine groups, carboxyl groups, sulfhydryl groups, guanidino groups, and the like refers to forms of these functionalities which are protected from undesirable reaction with a protecting group known to those skilled in the art such as those set forth in *Protective Groups in Organic Synthesis*, Greene, T. W.; Wuts, P. G. M., John Wiley & Sons, New York, N.Y., (3rd Edition, 1999) and *The Practice of Peptide Synthesis*, Bodanszky, M. and Bodanszky, A., Springer-Verlag, New York, (1984), which can be added or removed using the procedures set forth therein. Examples of protected hydroxyl groups include, but are not limited to, silyl ethers such as those obtained by reaction of a hydroxyl group with a reagent such as, but not limited to, t-butyldimethylchlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; carbamates such as t-butyl carbamate (Boc), fluorenylmethyl carbamate (Fmoc), and benzyl carbamate (Cbz); and others. Examples of protected sulfhydryl groups include, but are not limited to, thioethers such as S-t-butyl thioether, S-benzyl thioether, and S-4-picolyl thioether; substituted S-methyl derivatives such as hemithio, dithio and aminothio acetals; and others. Examples of protected carboxyl groups include but are not limited to esters such as methyl, ethyl, t-butyl, trimethylsilylethyl, benzyl, and the like.

The phrase "unprotected amino acid" refers to a substituted alkyl, substituted aralkyl, or a substituted heterocyclylalkyl bearing at least an amino group and at least a carboxylic acid group wherein the amino group and carboxylic acid group are not further protected as defined above. The phrase further includes nitrogen-containing heterocyclyl groups such as pyrrolidinyl, piperidinyl, piperazinyl, and the like, that also bear at least one carboxylic acid group. Thus, the phrase includes both naturally occurring and synthetic amino acids. Unprotected amino acids include, but are not limited to, alpha-amino acids, beta-amino acids, and gamma-amino acids. More specifically, the phrase includes, but is not limited to, glycine, alanine, valine, leucine, isoleucine, apartic acid, glutamic acid, gamma-carboxyglutamic acid, asparagine, glutamine, serine, threonine, cysteine, methionine, phenylalanine, histidine, tryptophan, tyrosine, 3,5-dibromotyrosine, 3,5-diiodotyrosine, proline, arginine, lysine, ornithine, beta-alanine, and gamma-aminobutyric acid.

The phrase "protected amino acid" refers to an unprotected amino acid which includes one or more protecting groups as defined above. Protecting groups may be attached to the amino group, the carboxylic acid group, or another functional group on the amino acid such as a hydroxy, thiol, another amine, another carboxyl, guanidino, and the like.

The phrase "unprotected dipeptide" refers to the group formed from two unprotected amino acids as defined above which are bound to each other through an amide bond. The amide bond is formed from the nitrogen from an amino group of one unprotected amino acid and a carbonyl from the other unprotected amino acid. Similarly, the phrase "protected dipeptide" refers to a dipeptide formed from at least one protected amino acid with another protected or unprotected amino acid.

A method of synthesizing a diazaphosphacycle includes reacting a phosphine with a diimine and optionally one or more equivalents of an acid halide, a sulfonyl halide, a phosphoryl halide, or an acid anhydride in the substantial absence of $O_2$ to form the diazaphosphacycle. The phosphine has the formula I

$R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups. Preferred $R^1$ groups include substituted and unsubstituted phenyl groups and substituted and unsubstituted cycloalkyl groups such as, but not limited to substituted and unsubstituted cyclopentyl groups and cyclohexyl groups. Other preferred $R^1$ groups include one or more —$PH_2$ group such that the phosphine is a polyphosphine. Employing a polyphosphine in the method provides for the production of bidentate ligands. Examples of suitable polyphosphines for use in the methods of the invention include, but are not limited to, 1,2-diphosphinoethane, 1,2-diphosphinoethylene, 1,3-diphosphinopropane, substituted or unsubstituted 1,2-diphosphinobenzene groups, substituted or unsubstituted 1,8-diphosphinoanthracene groups, substituted or unsubstituted 1,8-diphosphino-9,10-dihydroanthracene groups, substituted or unsubstituted 1,8-diphosphinoxanthene groups, or 1,1'-diphosphinoferrocene groups.

The reaction of a diimine with a phosphine of formula I is preferably conducted in a solvent such as, but not limited to, a substantially deoxygenated ether such as diethyl ether or tetrahydrofuran; a substantially deoxygenated alcohol such as ethanol or methanol; substantially deoxygenated water; or substantially deoxygenated dichloroethane. An acid is preferably present when the diimine reacts with the phosphine of formula I. Examples of suitable acids include, but are not limited to hydrochloric acid and hydrobromic acid.

Although not required, in certain preferred methods according the invention, the diimine and the phosphine are reacted in the presence of the optional acid halide, the sulfonyl halide, the phosphoryl halide, or the acid anhydride. The presence of one of the optional halides or anhydride provides for carboxylation, phosphorylation, or sulfonylation of one or both of the N atoms in diazaphosphacycle ring. In some preferred embodiments, the method is conducted in the presence of an acid halide such as, but not limited to acetyl chloride, acetyl bromide, phthaloyl dichloride, or phthaloyl dibromide. In other preferred embodiments, the reaction is conducted in the presence of a diacid dihalide such as phthaloyl dichloride or phthaloyl dibromide. In still other preferred embodiments, the reaction of the diimine with the phosphine is conducted in the presence of an acid anhydride.

The reaction between the diimine and the phosphine is typically conducted at temperatures ranging from less than 0° C. to about 50° C. More preferably, the reaction is conducted at temperatures ranging from at or about 0° C. to at or about 25° C.

In preferred methods of synthesizing diazaphosphacycles, the diimine reacted with the phosphine of formula I has the formula II. In such methods, the diazaphosphacycle formed has the formula III

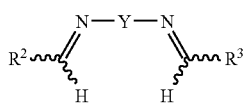

-continued

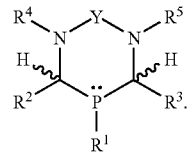

$R^2$ and $R^3$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups. In some preferred methods and diazaphosphacycles of the invention, $R^2$ and $R^3$ are identical, but are not part of the same group. In other words, if $R^2$ is a phenyl group, then $R^3$ is another phenyl group. Preferred $R^2$ and $R^3$ groups include phenyl, 2-furanyl, protected pyrrolyl, n-propyl, i-propyl, t-butyl, ferrocenyl, o-hydroxyphenyl, o-tolyl, 2-naphthyl, and pentafluorophenyl groups.

$R^4$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(=O)—$R^6$ groups, —S(=O)$_2$—$R^6$ groups, —P(=O)$R^6R^7$ groups, or —C(=N$R^6$)—$R^7$ groups. Preferred $R^4$ groups include —H, and —C(=O)—$R^6$ groups.

$R^5$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(=O)—$R^7$ groups, —S(=O)$_2$—$R^7$ groups, —P(=O)$R^6R^7$ groups, or —C(=N$R^6$)—$R^7$ groups. Preferred $R^5$ groups include —H and —C(=O)—$R^7$ groups. In some preferred methods and diazaphosphacycles, $R^4$ is a —C(=O)—$R^6$ group and $R^5$ is a —C(=O)—$R^7$ group.

$R^6$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups. Preferred $R^6$ groups include alkyl groups such as methyl, ethyl, propyl, butyl, pentyl, and hexyl groups and groups where $R^6$ and $R^7$ join together with the two ring nitrogen atoms of the diazaphosphacycle to form a ring.

$R^7$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups. Preferred $R^7$ groups include alkyl groups such as methyl, ethyl, propyl, butyl, pentyl, and hexyl groups and groups where, as indicated above, $R^6$ and $R^7$ join together with the two ring nitrogen atoms of the diazaphosphacycle to form a ring.

$R^6$ and $R^7$ may be part of the same alkyl group, alkenyl group, or aryl group such that $R^4$ and $R^5$ together with the two nitrogen atoms of the diazaphosphacycle form a ring. Preferred such compounds include those where the ring formed has 6 ring members.

Y is a linking group selected from substituted or unsubstituted cycloalkyl groups, substituted or unsubstituted aryl groups, substituted or unsubstituted alkenyl groups, silyl groups, substituted alkyl groups, or groups having the formula —$(CH_2)_n$— wherein n is selected from the group consisting of 0, 1, 2, and 3. In some preferred methods and diazaphosphacycles, Y is a —$(CH_2)_n$— group where n is 0. In such compounds the nitrogen atoms of the diazaphosphacycle are directly bonded to one another and the compound is a 3,4-diazaphospholane. In other preferred methods and diazaphosphacycles, Y is a cycloalkyl group and one of the nitrogen atoms of the diimine is bonded to a first ring member carbon atom of the cycloalkyl group and the other nitrogen atom of the diimine is bonded to a second ring member carbon atom. Furthermore, in such preferred compounds, the second ring member carbon atom of the cycloalkyl group is directly bonded to the first ring member carbon atom of the cycloalkyl group such that the cycloalkyl group is a 1,2-disubstituted cycloalkyl group such as a 1,2-disubstituted cyclohexyl group. Both cis and trans 1,2-disubstituted alkyl groups are preferred. Other preferred Y groups have the following formula where the benzene ring of the group may be further substituted:

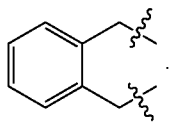

In other preferred methods and diazaphosphacycles, the diazaphosphacycle has the formula IIIA, the formula IIIB, or is a mixture of diazaphosphacycles of formulas IIIA and IIIB. Such diazaphosphacycles are generally referred to as rac compounds. In more preferred such diazaphosphacycles, Y is a —$(CH_2)_n$— group where n is 0.

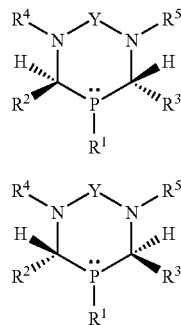

IIIA

IIIB

In other preferred methods and diazaphosphacycles, the diazaphosphacycle has the formula IIIC. Such compounds are generally referred to as meso compounds. In more preferred such compounds, Y is a —$(CH_2)_n$— group where n is 0 so that the ring nitrogen atoms of the diazaphosphacycle are directly bonded to one another.

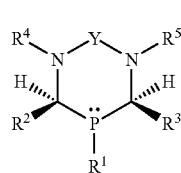

IIIC

The methods disclosed herein may be used to produce diazaphosphacycles where both $R^4$ and $R^5$ are —H. Such a method typically involves reaction of the phosphine of formula I with the diimine of formula II in the absence of acid halide, acid anhydride, sulfonyl halide, and/or phosphoryl halide. When such a method is used, the method may include the later addition of an acid halide, an acid anhydride, a sulfonyl halide, or a phosphoryl halide. Preferably an acid halide or an acid anhydride is used in such a method. The later addition of one of the above-specified reagents forms a second diazaphosphacycle in which at least one of $R^4$ and $R^5$ is not —H. In other preferred such methods, neither $R^4$ nor $R^5$ is an —H in the second diazaphosphacycle.

The widely different groups that may be used for $R^1$-$R^6$ and Y in the method of the invention allows a library of different diazaphosphacycles to be produced from readily available starting materials. Such a library may be produced using standard combinatorial methods allowing for the production of large numbers of diazaphosphacycles both in solution or on solid phase.

A first alternative method of synthesizing a diazaphosphacycle includes reacting a diimine with an acid halide, a diacid dihalide, a sulfonyl halide, a disulfonyl dihalide, a phosphoryl halide, or a diphosphoryl dihalide to form a dihalo intermediate compound. The method further includes reacting the dihalo intermediate compound with a phosphine of formula $R^1$—$PH_2$ in the substantial absence of $O_2$ to form the diazaphosphacycle. In the method, $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups; and the diimine has the formula IV

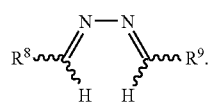

IV $R^8$ and $R^9$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups. Any of the reaction conditions suitable for the previously described method may be used in conjunction with this first alternative method. In some preferred such methods and diazaphosphacycles produced therefrom, $R^8$ and $R^9$ are identical, but are not part of the same group. In other words, if $R^8$ is a phenyl group, then $R^9$ is another phenyl group. Preferred $R^8$ and $R^9$ groups include phenyl, 2-furanyl, protected pyrrolyl, n-propyl, i-propyl, t-butyl, ferrocenyl, o-hydroxyphenyl, o-tolyl, 2-naphthyl, and pentafluorophenyl groups. Substituted and unsubstituted aryl groups are particularly suitable as $R^8$ and $R^9$ groups.

Still other such methods are provided in which the diimine is reacted with a diacyl dihalide, and the diacyl dihalide has the formula V or the formula VI and the diazaphosphacycle has the formula VII or the formula VIII

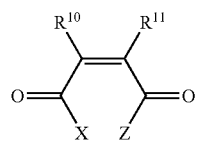

V

-continued

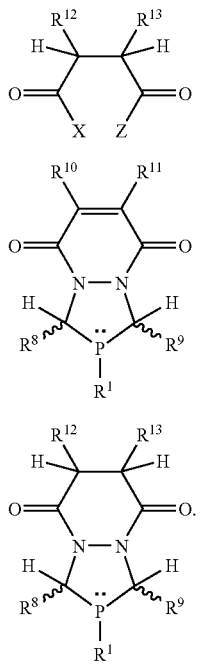

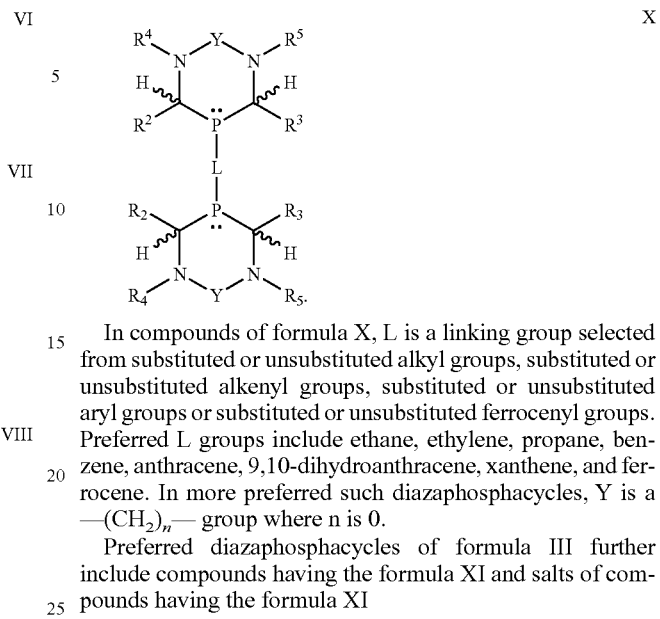

In compounds of formula X, L is a linking group selected from substituted or unsubstituted alkyl groups, substituted or unsubstituted alkenyl groups, substituted or unsubstituted aryl groups or substituted or unsubstituted ferrocenyl groups. Preferred L groups include ethane, ethylene, propane, benzene, anthracene, 9,10-dihydroanthracene, xanthene, and ferrocene. In more preferred such diazaphosphacycles, Y is a —$(CH_2)_n$— group where n is 0.

Preferred diazaphosphacycles of formula III further include compounds having the formula XI and salts of compounds having the formula XI

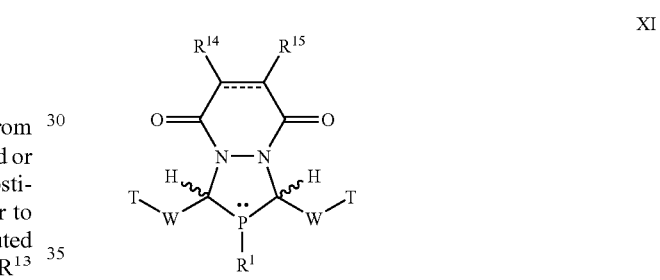

$R^{10}$, $R^{11}$, $R^{12}$, and $R^{13}$ are independently selected from —H, substituted or unsubstituted alkyl groups, substituted or unsubstituted cycloalkyl groups, or substituted or unsubstituted aryl groups. $R^{10}$ and $R^{11}$ may further join together to form a substituted or unsubstituted aryl group or a substituted or unsubstituted cycloalkenyl group. Similarly, $R^{12}$ and $R^{13}$ may join together to form a substituted or unsubstituted cycloalkenyl group or a substituted or unsubstituted cycloalkyl group.

X and Z are independently selected from —Cl or —Br.

In particularly preferred methods for synthesizing diazaphosphacycles according to the alternative method, phthaloyl dichloride is the diacyl dihalide of formula V.

Preferred diazaphosphacycles include any of the compounds having the formulas III, IIIA, IIIB, IIIC, VII, or VIII produced by any of the methods of the present invention. Preferred diazaphosphacycles of the invention further include compounds of the formula IX

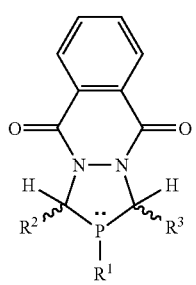

where $R^1$, $R^2$, and $R^3$ have any of the values set forth above with respect to formula III.

Preferred diazaphosphacycles of formula III include those having the formula X wherein W, at each occurrence, is independently selected from the group consisting of aryl, cycloalkyl, and heterocyclyl groups wherein W optionally comprises one or more substituents in addition to T;

T, at each occurrence is independently selected from the group consisting of —C(O)—$OR^{16}$, —C(O)—$NR^{17}R^{18}$, —C(O)—$N(R^{17})OR^{18}$, substituted and unsubstituted oxazole, substituted and unsubstituted oxazoline, and substituted and unsubstituted oxazolidine groups;

$R^1$ is selected from the group consisting of substituted and unsubstituted aryl, substituted and unsubstituted alkyl, substituted and unsubstituted alkenyl, substituted and unsubstituted cycloalkyl, and substituted and unsubstituted ferrocenyl groups;

$R^{14}$ and $R^{15}$ are independently selected from the group consisting of —H, substituted and unsubstituted alkyl, substituted and unsubstituted cycloalkyl, and substituted and unsubstituted aryl; or $R^{14}$ and $R^{15}$ may join together to form a substituted or unsubstituted aryl, a substituted or unsubstituted cycloalkyl, or a substituted or unsubstituted cycloalkenyl group;

$R^{16}$, $R^{17}$ and $R^{18}$ are each independently selected from the group consisting of —H, and substituted and unsubstituted alkyl, substituted and unsubstituted aryl, substituted and unsubstituted aralkyl, substituted and unsubstituted heterocyclyl, substituted and unsubstituted heterocyclylalkyl groups; or $R^{17}$ and $R^{18}$ may join together to form a non-aromatic heterocyclyl group; and the dashed line represents a single or double carbon-carbon bond.

In some embodiments of the diazaphosphacycle of formula XI, $R^{14}$ and $R^{15}$ join together to form a substituted or unsubstituted aryl group. In other embodiments, $R^{14}$ and $R^{15}$ join together to form a substituted or unsubstituted cycloalkyl or a substituted or unsubstituted cycloalkenyl group. In still other embodiments, W at each occurrence is independently an aryl group. In further embodiments, W at each occurrence is independently a phenyl group.

In some embodiments of the diazaphosphacycle of formula XI, T is —C(O)—OR$^{16}$, and in others T is —C(O)—OH. In further embodiments, T is —C(O)—NR$^{17}$R$^{18}$, and in some such embodiments, R$^{17}$ is —H. In still other embodiments, T is —C(O)—N(R$^{17}$)OR$^{18}$, and in other embodiments, T is 2,5-dihydrooxazole. In some embodiments, T at each occurrence is the same.

In certain embodiments of diazaphosphacycles having formula XI, the invention provides compounds of formula XII

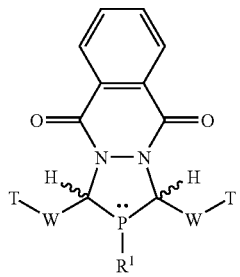

XII wherein the variables W, T, and $R^1$ are as defined above.

Particularly preferred are embodiments where diazaphosphacycles of formula XI have the formula XIII:

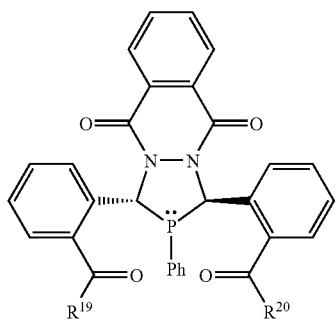

XIII wherein $R^{19}$ and $R^{20}$ are independently selected from the group consisting of substituted and unsubstituted alkyl amine, substituted and unsubstituted aralkyl amine, substituted and unsubstituted N-containing heterocyclyl groups, protected and unprotected amino acids, protected and unprotected amino acid esters, and protected and unprotected dipeptides; and wherein $R^{19}$ and $R^{20}$ are attached to the rest of the compound of Formula XIII through a nitrogen atom. In some such embodiments, $R^{19}$ and $R^{20}$ are independently selected from the group consisting of

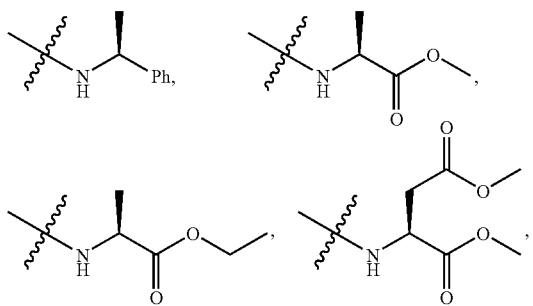

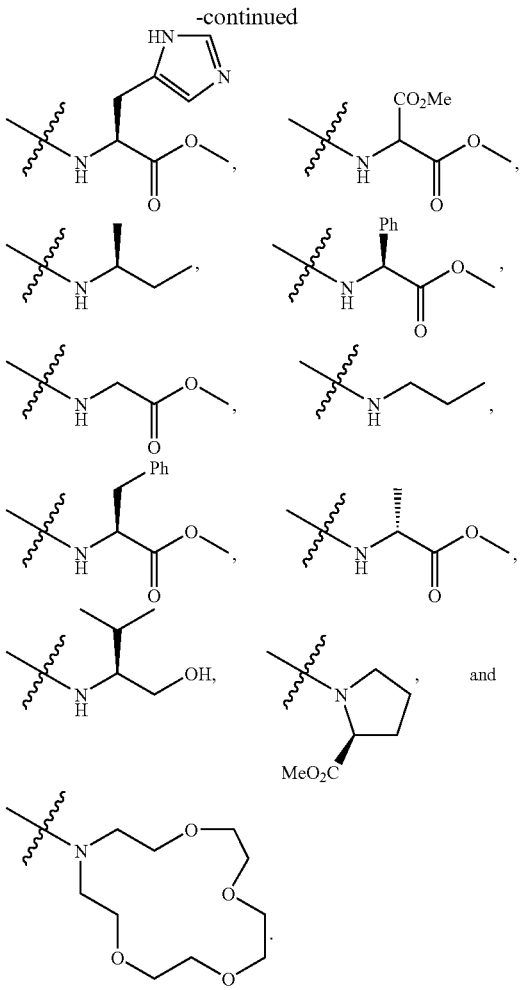

In other such embodiments, $R^{19}$ and $R^{20}$ are independently selected from the group consisting of

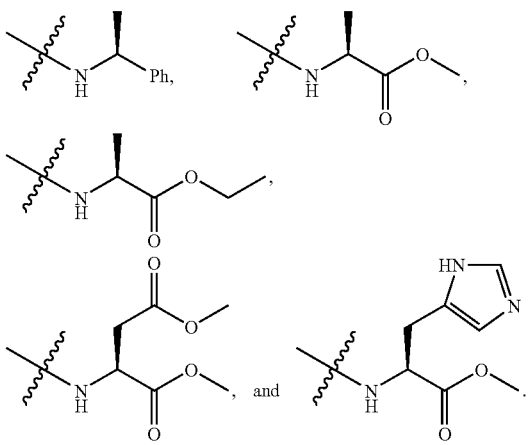

In still other such embodiments, $R^{19}$ and $R^{20}$ are the same. In yet other embodiments, $R^{19}$ and $R^{20}$ are protected or unprotected dipeptides such as Ala-Ala, Ala-Val, Ala-Met and the like.

Still further diazaphosphacycles are provided that having the formula XIA or XIB or mixtures thereof:

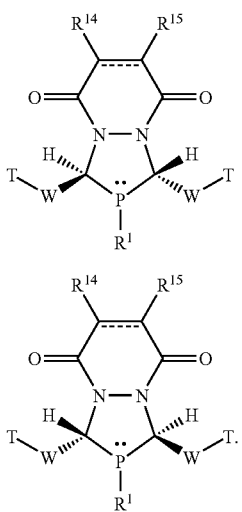

XIA

XIB

Typically, mixtures of XIA and XIB contain XIA and XIB in a proportion of at least 80% XIA and 20% XIB or contain XIB and XIA in a proportion of at least 80% XIB and 20% XIA. Preferably such mixtures contain XIA and XIB in a proportion of at least 90% XIA and 10% XIB or contain XIB and XIA in a proportion of at least 90% XIB and 10% XIA. Even more preferably, such mixtures contain XIA and XIB in a proportion of at least 95% XIA and 5% XIB or contain XIB and XIA in a proportion of at least 95% XIB and 5% XIA.

Still other diazaphosphacycles are provided that have the formula XIC:

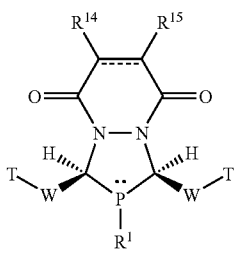

XIC

In a particularly preferred embodiment, the invention provides the diazaphosphacycle of formula XIV.

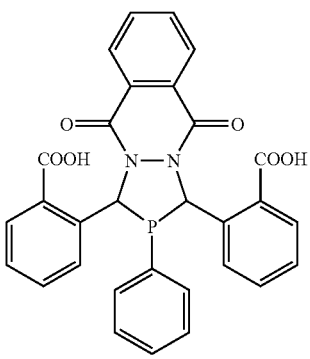

XIV

The compound of formula XIV is an air-stable diazaphosphacycle readily synthesized from inexpensive starting materials. Both enantiomers are available by resolution of the racemic compound according to the selective crystallization methods described herein. For example, compounds of formula XIA and XIB are available as compounds of formula XIVA and XIVB respectively.

XIVA

XIVB

Thus, the diazaphosphacycles of formulas XIV, XIVA, and XIVB are particularly advantageous for use in producing libraries by the herein disclosed methods.

The invention further provides diazaphosphacycles of formula XI having the formula XV

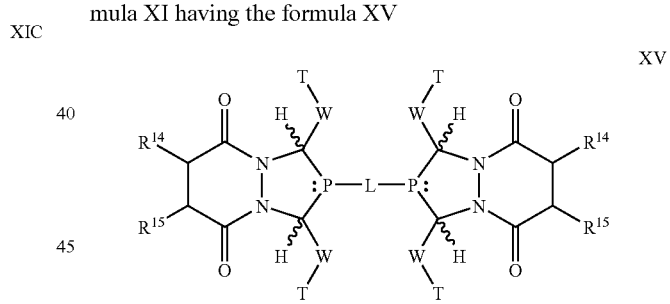

XV wherein L is a linking group selected from the group consisting of substituted and unsubstituted alkyl groups, substituted and unsubstituted alkenyl groups, substituted and unsubstituted aryl groups, and substituted and unsubstituted ferrocenyl groups. In some such embodiments, L is selected from the group consisting of ethane, ethylene, propane, benzene, anthracene, 9,10-dihydroanthracene, xanthene, and ferrocene groups.

Figure 17:
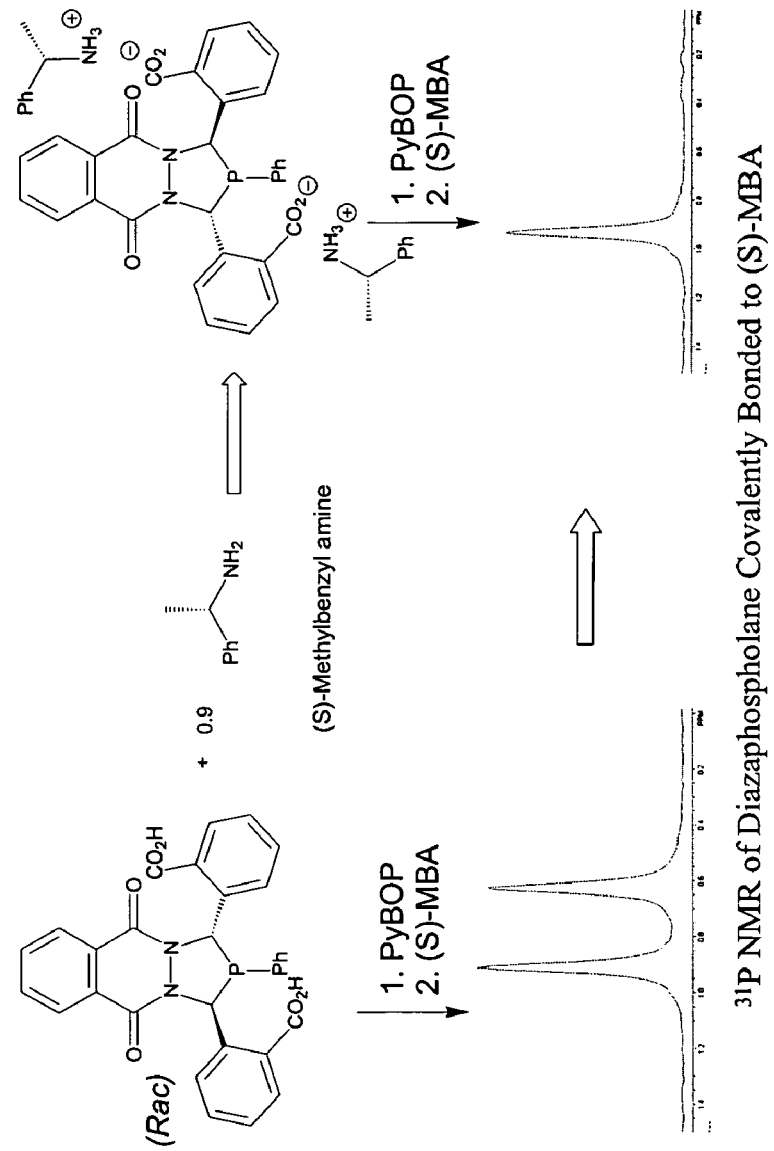
FIG. 17 is a side-by-side NMR spectrum comparing the $^{31}$P NMR spectrum of the diasteromeric mixture of formula XIV coupled to (S)-methylbenzylamine (left) with the chirally pure (R,R)-diastereomer of the same compound.
Figure 18:
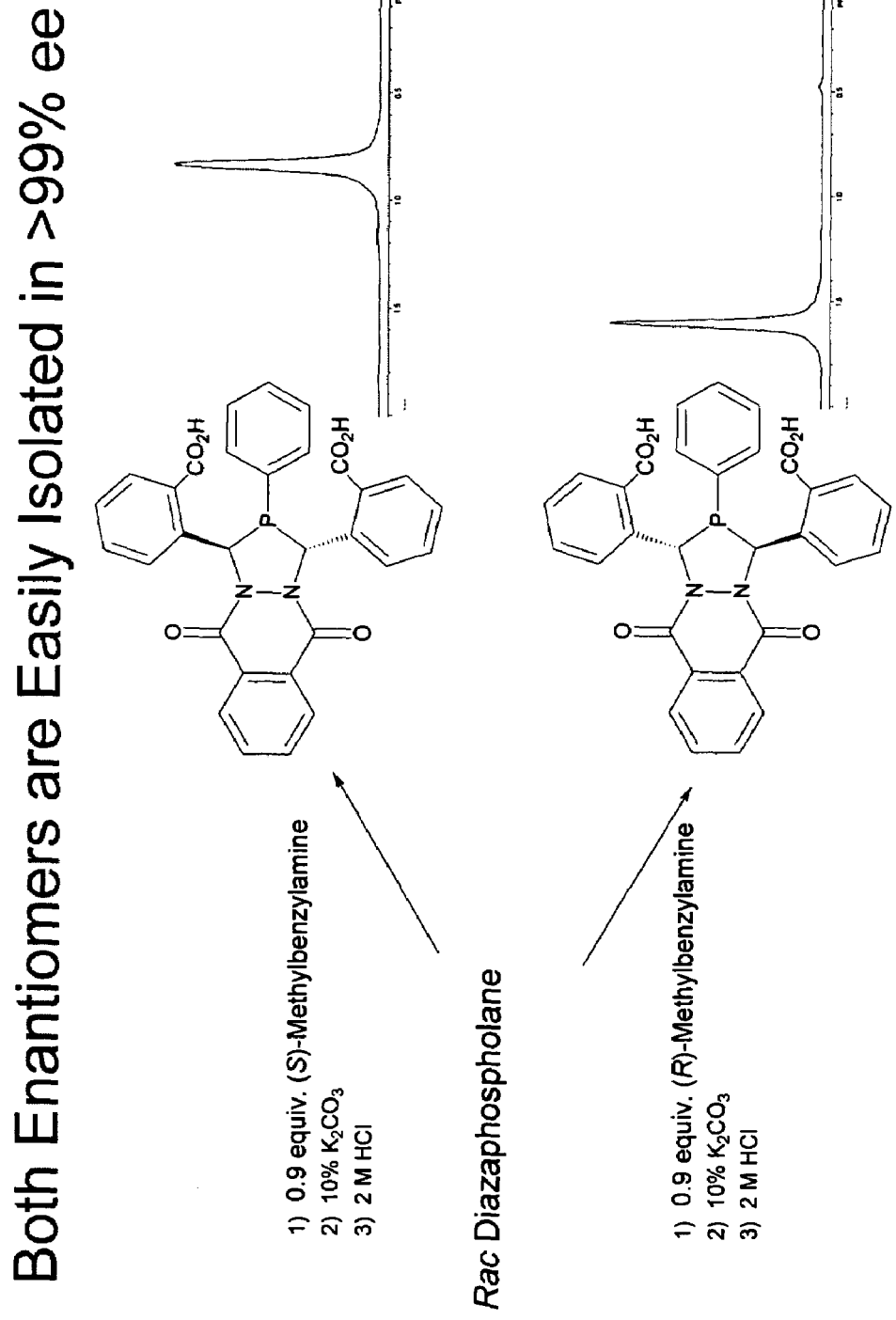
FIG. 18 illustrates the resolution method of the present invention and shows the $^{31}$P NMR spectra of the resolved enantiomers of diazaphosphacycle XIV, each enantiomer having greater than 99% ee.
Figure 19:
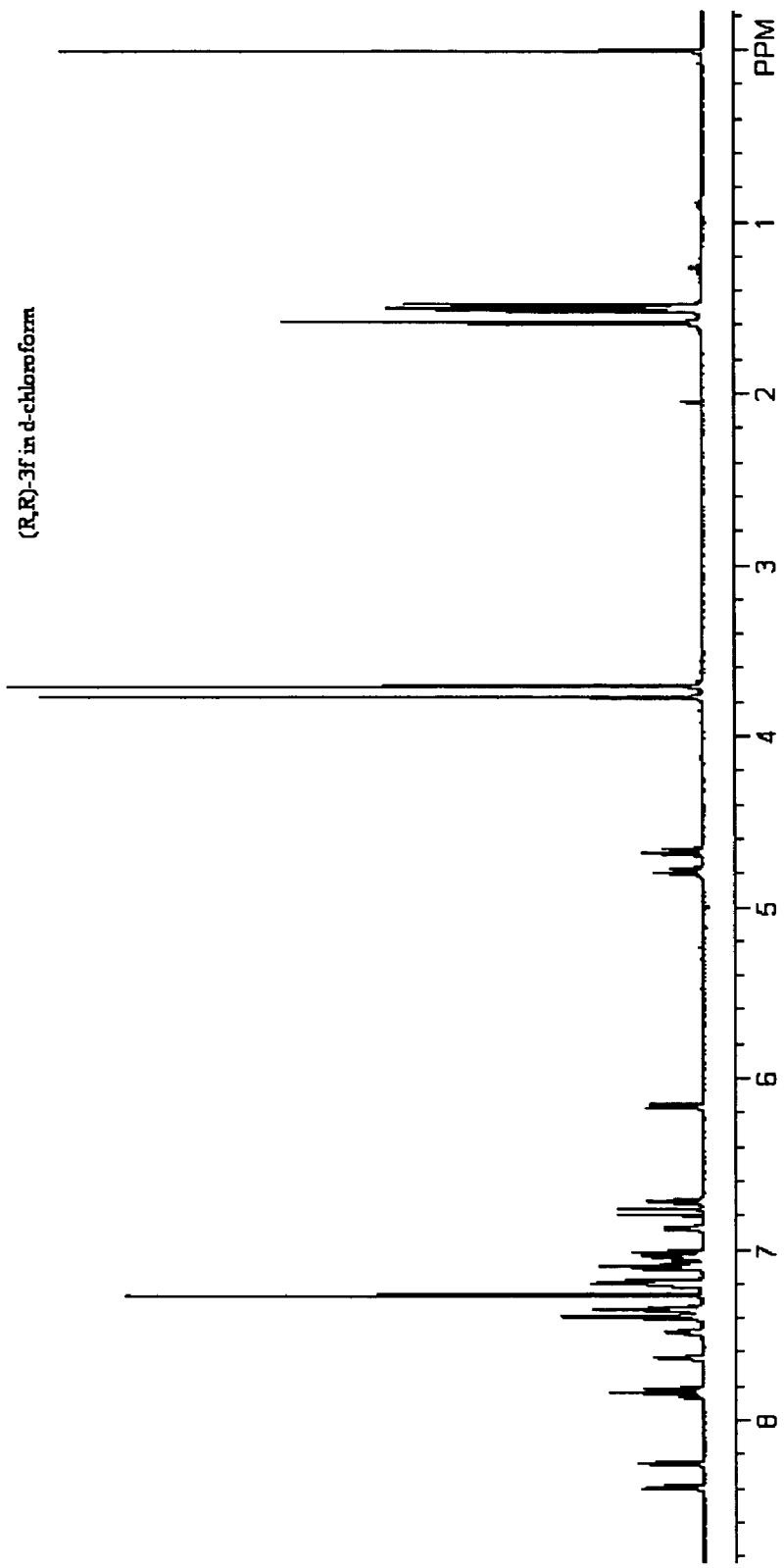
FIG. 19 is a $^1$H NMR spectrum of 3f' in chloroform-d$_3$.
Figure 20:
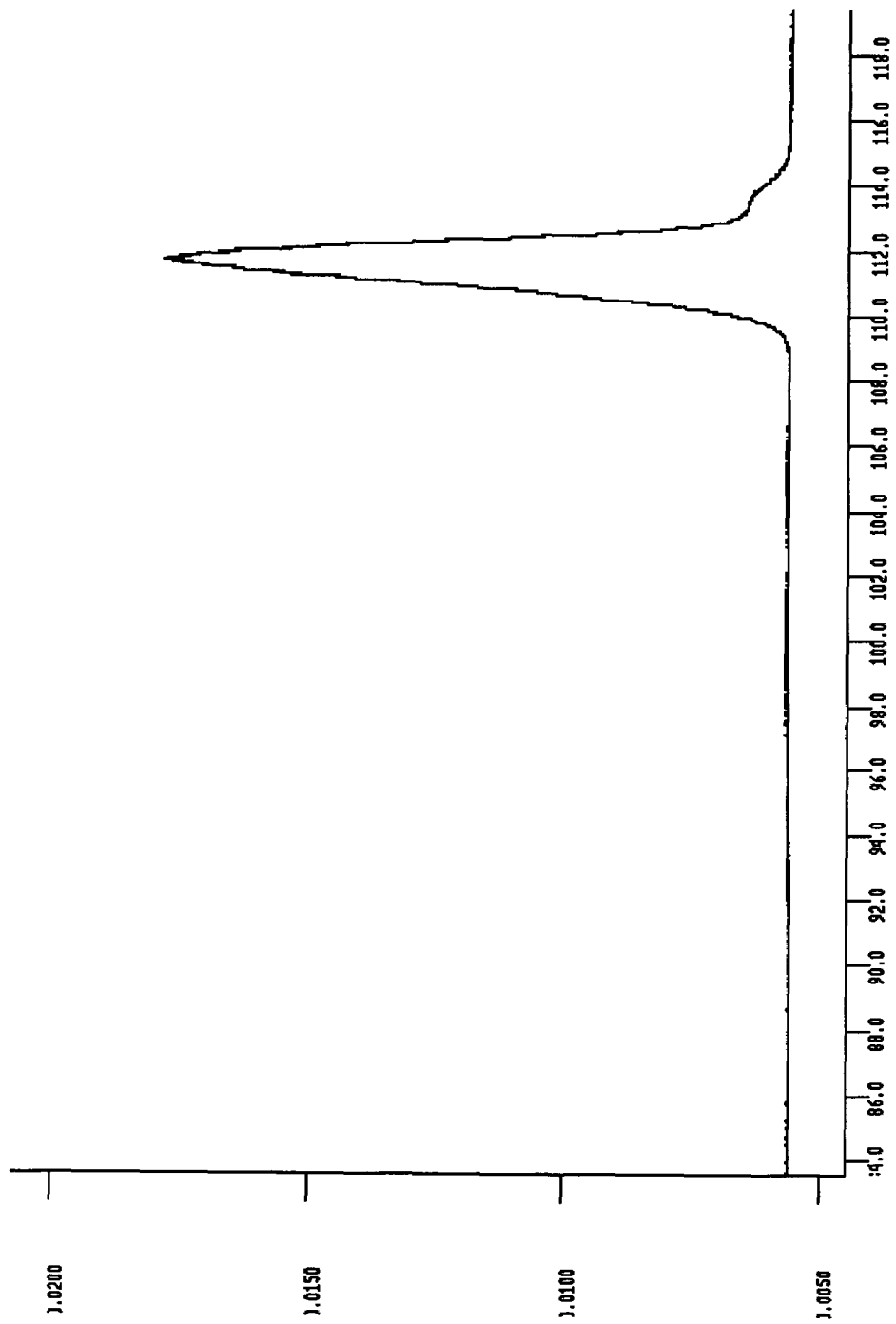
FIG. 20 is a GC trace of the allylic alkylation product 5a' from substrate 4a', ligand (R,R)-3f' and AgPF$_6$. Conditions: Column Temp: 70° C., Flow Rate: 1.8 mL/min.
Figure 21:
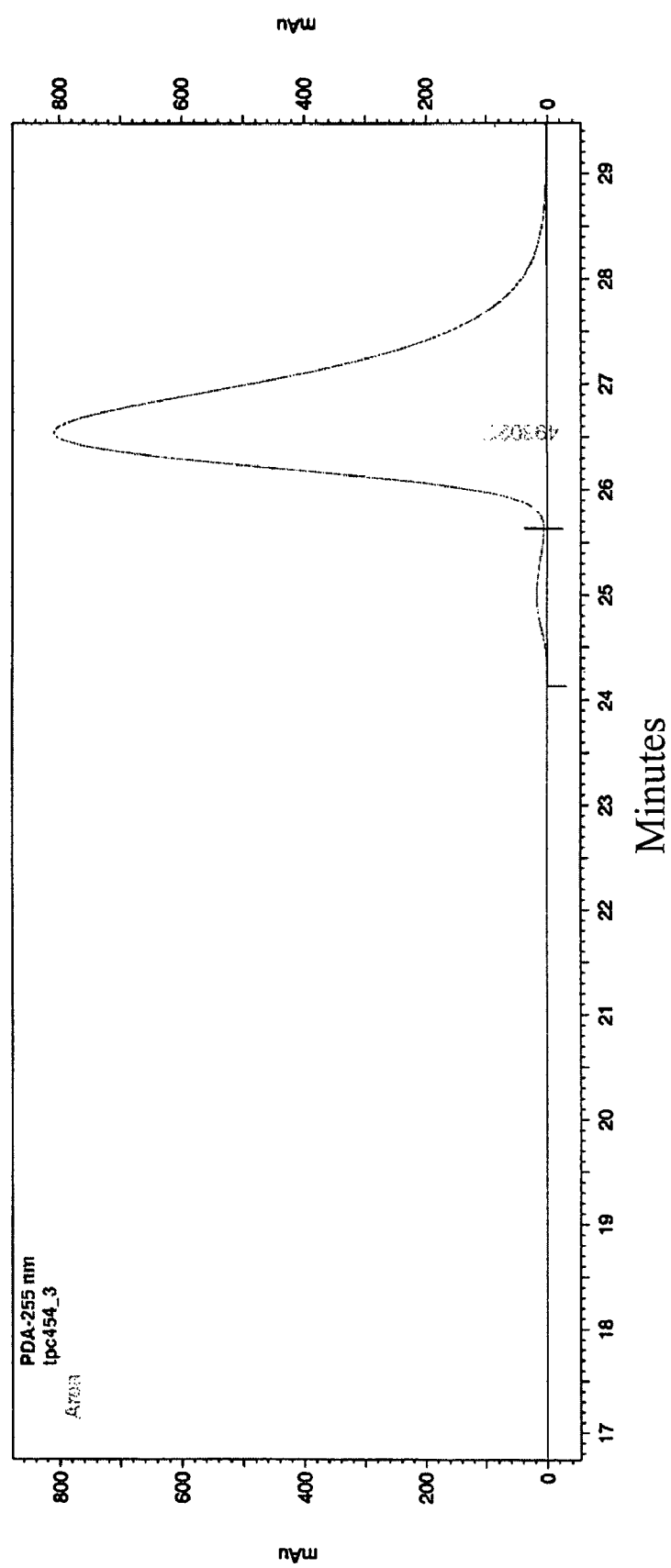
FIG. 21 is an HPLC chromatogram of the allylic alkylation product 5 b from substrate 4b', ligand (R,R)-3f', and without AgPF$_6$. Conditions: 99:1 hexanes/2-propanol; 0.5 mL/min flow rate; 255 nm detection.

The invention provides a simple and cost-effective method of resolving the diazaphosphacycle of formula XI wherein T at each occurrence is —COOH to give either enantiomer. The method includes selectively crystallizing a mixture of the diazaphosphacycle with either (S)- or (R)-methylbenzylamine. Typically, about 0.9 equivalents of the alpha-methylbenzylamine is used compared to the diazaphosphacycle. The stereochemical purity of the resulting diazaphosphacycle is conveniently determined by $^{31}$P NMR after formation of the diamide derivative with (S)-alpha-methylbenzylamine ((S)-MBA). The diamide derivative may be formed by reacting the resolved diazaphosphacycle with (S)-MBA in the presence of a coupling reagent such as benzotriazol-1-yloxy)tripyrrolidinophosphonium hexafluorophosphate (PyBOP) or by reacting the diacid chloride of the diazaphosphacycle with (S)-MBA. FIG. 17 shows the $^{31}$P NMR of such a derivative before and after resolution; only a single diastereomer (and thus enantiomer) of the resolved diazaphosphacycle is detectable. In some embodiments of the method of resolving the diazaphosphacycle of formula XI wherein T at each occurrence is —COOH, W at each occurrence is phenyl. FIG. 18 shows the $^{31}$P NMR of the resolved enantiomers of such a compound wherein each enantiomer exhibits >99% ee. Where diazaphosphacycles of formula XI or XIII lack carboxyl groups, the compounds may be resolved using preparative HPLC using a chiral column, e.g. a Chiracel OD column.

The invention provides libraries that include diazaphosphacycles of the present invention. Particularly preferred are combinatorial libraries that include at least one diazaphosphacycle having formula XI, XIA, XIB, XIC, XII, XIII, XIV, XIVA, XIVB, or XV. The libraries may be constructed in solution or on solid-phase and therefore include compounds of the invention covalently attached to a solid support resin. In some embodiments, libraries of compounds of formulas XI, XII, or XIII may readily be prepared when T is —COOH. For example, the carboxyl groups may be converted to acid halides using known reagents, such as thionyl chloride or phosphorous oxychloride, and reacted with an amine, such as a carboxyl protected amino acid, an alkyl amine, a hydroxylamine, or a nitrogen-containing saturated heterocyclyl, to yield diamide derivatives. Alternatively, a coupling agent such as PyBOP may be used to form an amide bond between the carboxyl groups and amines. Similarly, esters may be prepared by coupling alcohols to the carboxyl groups. Further, coupling of amino alcohols to the carboxyl followed by activation of the hydroxyl as a leaving group (e.g. as tosylate, mesylate, or triflate) provides oxazoline derivatives. Thus, as will be understood by one of skill in the art, any standard amide and ester bond forming procedures may be used to prepare libraries of compounds of the present invention. These include but are not limited to the procedures found in: Jones, John *Amino Acid and Peptide Synthesis* Ed. Steven G. Davies, Oxford Science (1992) (general coupling procedures); Coste, J.; Le-Nguyen, D.; Castro, B. *Tet. Lett.* 1990, 31, 205-208 (PyBOP coupling procedure); Copeland, G. T.; Miller, S. J. *J. Am. Chem. Soc.* 2001, 123, 6496-6502, and Gilbertson, S. R.; Collibee, S. E.; Agarkov, A. *J. Am. Chem. Soc.* 2000, 122, 6522-6523 (library synthesis procedures).

Scheme 1 shows how various 3,4-diazaphosphacycles may be synthesized from simple starting materials to provide a large number of chiral phosphine ligands.

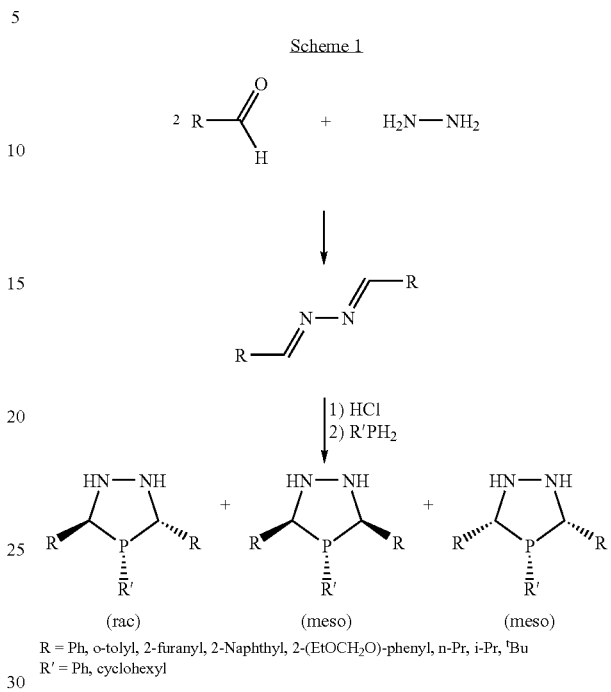

As shown in Scheme 1, the reaction of 2 equivalents of an aldehyde such as aldehydes where R is an alkyl group or aryl group with a diamine such as hydrazine readily affords the diimines for use in the method for producing the diazaphosphacycles. An excess of aldehyde may be used to produce the diimine. The reaction shown in Scheme 1 may be carried out in a rac selective manner. The reaction typically provides high yields in excess of 80 percent of the 3,4-diazaphospholanes.

Scheme 2 shows the synthesis of numerous different diazaphosphacycles from simple and readily available diimines and phosphines. The diimine is formed from hydrazine and the appropriate aldehyde. Thus, the diimine is a compound of formula II as described above, where Y is a —$(CH_2)_n$— group where n is 0.

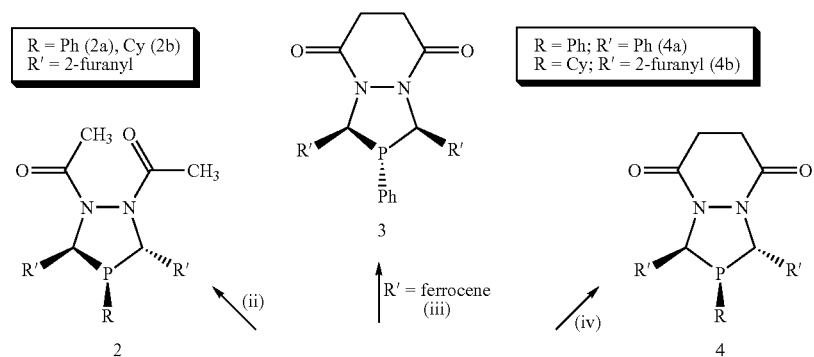

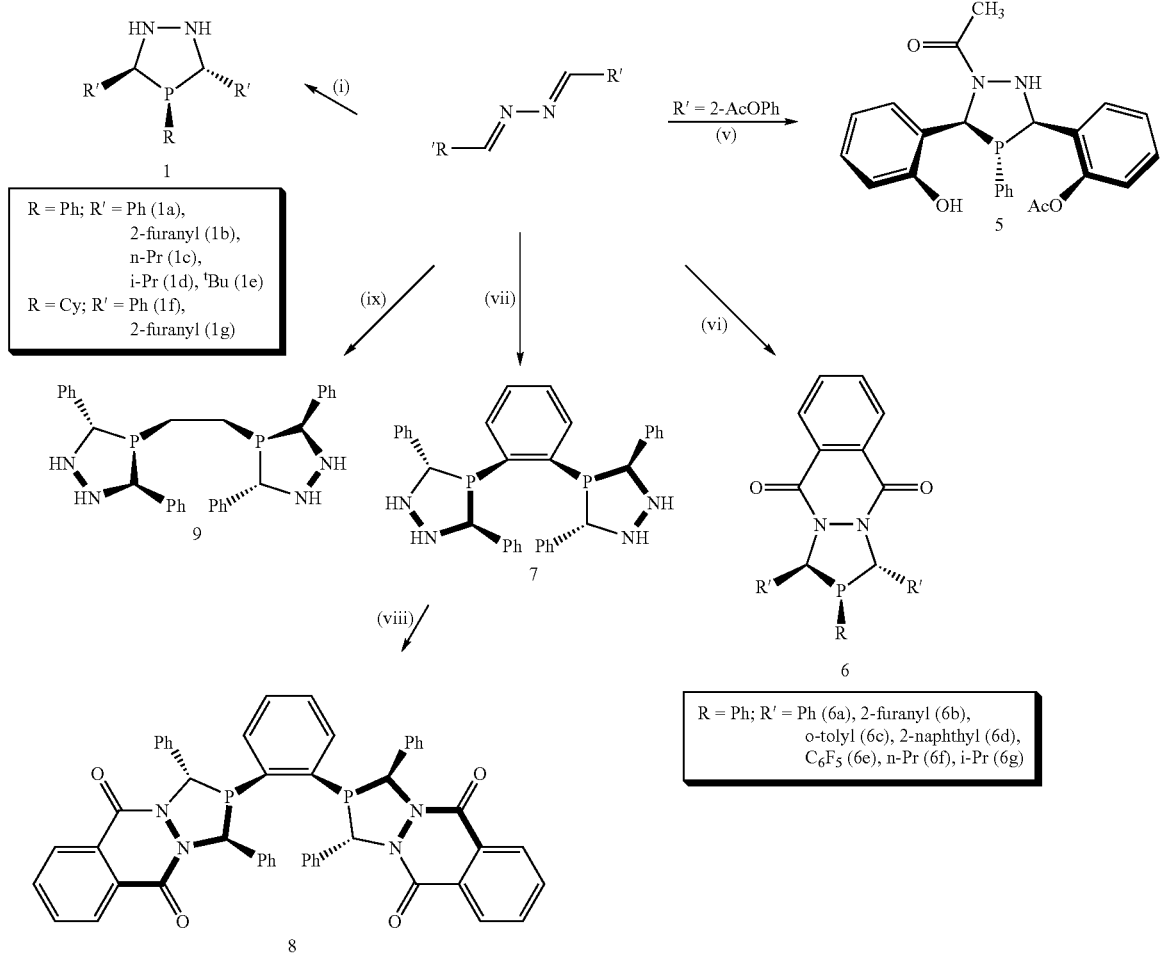

a(i) HCl, RPH$_2$, (ii) CH$_3$COCl, RPH$_2$ (iii) succinyl chloride, PhPH$_2$ (iv) succinyl chloride, RPH$_2$ (v) HCl, PhPH$_2$ (vi) phthaloyl chloride, PhPH$_2$ (vii) HCl, 1,2-(PH$_2$)$_2$C$_6$H$_4$ (viii) phthaloyl chloride in THF (ix) HCl, PH$_2$CH$_2$CH$_2$PH$_2$. All the reaction products were worked up with 10% K$_2$CO$_3$.

The condensation of diimines (R$^2$—CH=N—N=CH—R$^3$), shown generically as formula II, prepared by the reaction of hydrazine with 2 equivalents of the corresponding aldehyde, as shown in Scheme 1, and primary phosphines yields diazaphosphacycles such as compound 1. As set forth in Scheme 2, this procedure surprisingly and unexpectedly provides a variety of 3,4-diazaphospholanes in good yields (25-95%) and rac selectivity under mild reaction conditions.

Condensation of a diimine and a primary phosphine preferably with 1 equivalent of dry HCl as an acid promoter affords simple 3,4-diazaphospholanes (1, 7, 9). In preferred embodiments, acid chlorides are employed and function as both promoters and N-functionalization reagents to provide N,N'-dicarboxyl-3,4-diazaphospholanes (2, 3, 4, 6) directly in a one-step synthesis as illustrated in Scheme 2. Reaction of the diimine derived from acetyl salicylaldehyde with phenylphosphine yielded 5, a product in which one of the salicyl acetyl groups was transferred to the hydrazine moiety. As exemplified by the transformation of compound 7 to compound 8, 3,4-diazaphospholanes and acid chlorides react cleanly to provide a wide variety of N,N'-dicarboxyl-3,4-diazaphospholanes. The N,N'-dicarboxyl-3,4-diazaphospholanes exhibit higher thermal and chemical stability than simple 3,4-diazaphospholanes, although both are suitable for forming transition metal complexes.

Acid-promoted addition of primary phosphines to diimines are generally rac selective, but the reaction is sensitive to the selection of the R$^1$ group of the phosphine and to the selection of the R$^2$, R$^3$, R$^8$, and R$^9$ groups of the diimine used. For example, where R$^1$ is phenyl, rac/meso ratios (0.6-30:1) are dependent on the choice of R$^2$ and R$^3$ or R$^8$ and R$^9$. However, when R$^1$ is a cyclohexyl group, then formation of the rac isomers are highly preferred and in some cases are the only isomers observed. Diimines derived from bulky, electron withdrawing substituents such as pentafluorophenyl and ferrocenyl generally yield low rac/meso ratios (6e, 2:1; 3, 0.6:1). For most diazaphospholanes, simple recrystallization provides separation of diastereomers (e.g., rac/meso ratios 30:1 for 1a). The diazaphosphacycles were characterized by X-ray crystallography and $^1$H and $^{31}$P NMR spectroscopy as shown in FIGS. 1, 2, and 4-6.

Resolution of enantiomeric mixtures may be accomplished by various methods known to those skilled in the art. Resolution of racemic diazaphospholanes 1a, 1e, and 9 was accomplished by N-functionalization with di-O-methyl-L-tartaric acid dichloride to form bicyclic diastereomers followed by chromatographic separation on silica gel.

Scheme 3 shows how various functionalized 3,4-diazaphospholanes may be prepared from a diimine such as a diimine of formula II where Y is a —(CH$_2$)$_n$— group and n is 0.

Scheme 3

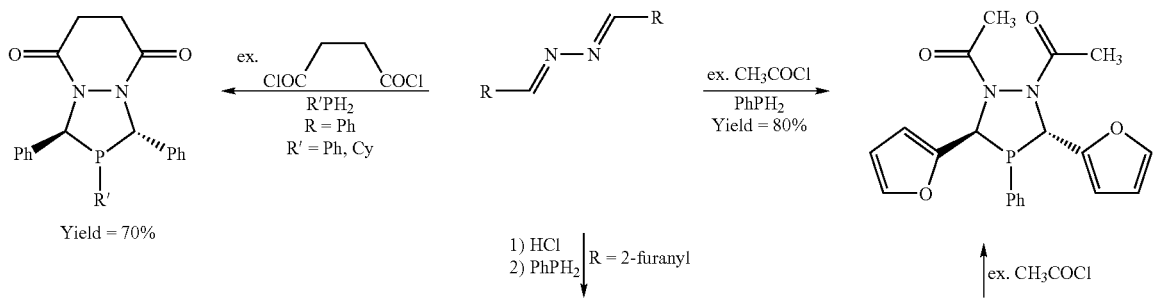

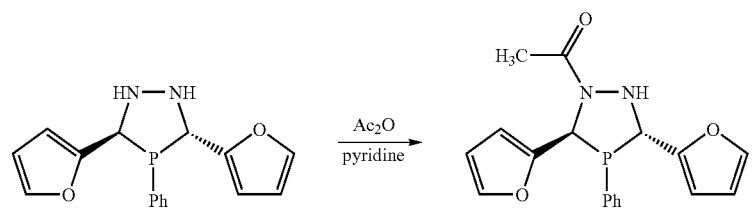

Scheme 4 shows a synthetic route for obtaining rigid bicyclic 3,4-diazaphospholanes from a diimine of formula II where Y is a —$(CH_2)_n$— group and n is 0.

Scheme 4

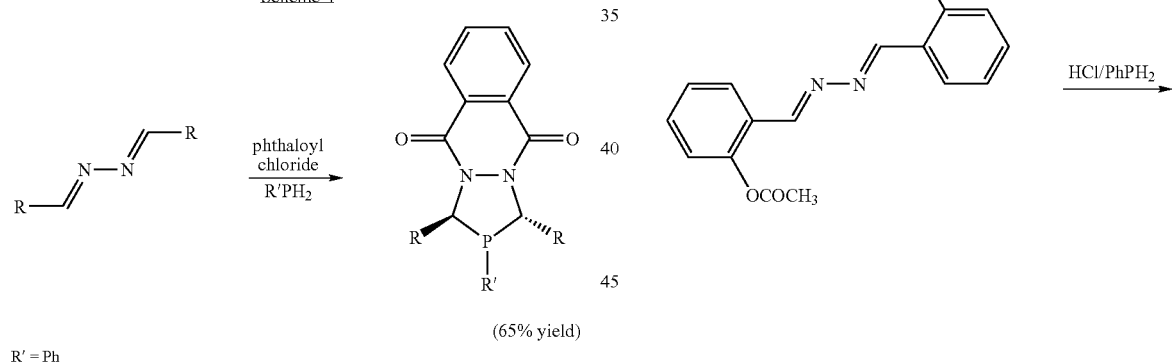

R' = Ph
R = Ph, 2-Naphthyl, o-tolyl, 2-furanyl, —$C_6F_5$, n-Pr, i-Pr

Scheme 5 shows a synthetic method that may be used for preparing a diazaphosphacycle that includes a hydroxyphenyl group.

Scheme 5

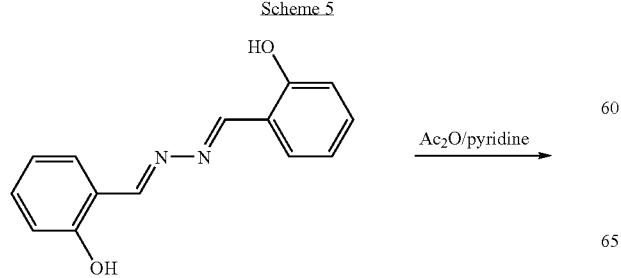

-continued

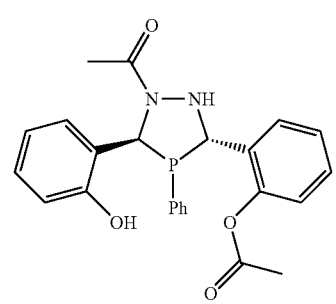

Scheme 6 shows a synthetic method for preparing a sterically demanding diazaphosphacycle that includes two ferrocenyl groups. As can be seen in Scheme 6, one of the products is thermally unstable and can be degraded.

Scheme 6

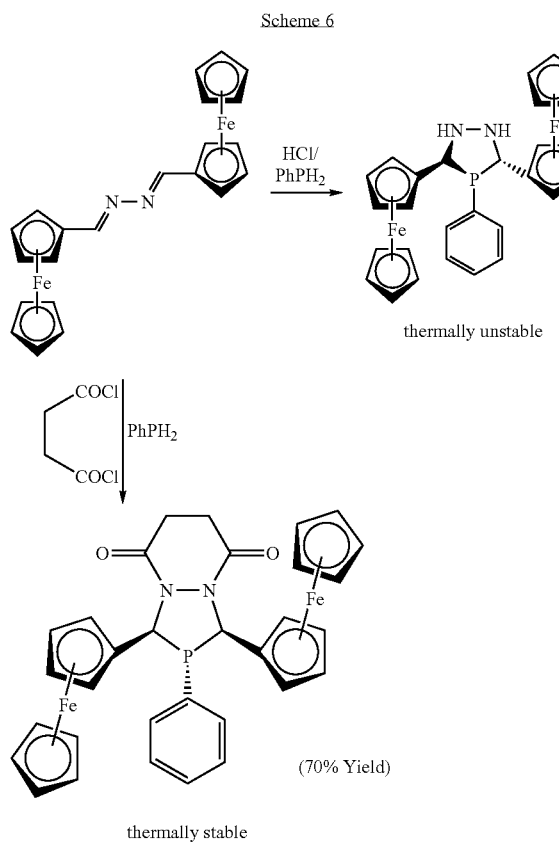

Figure 3:
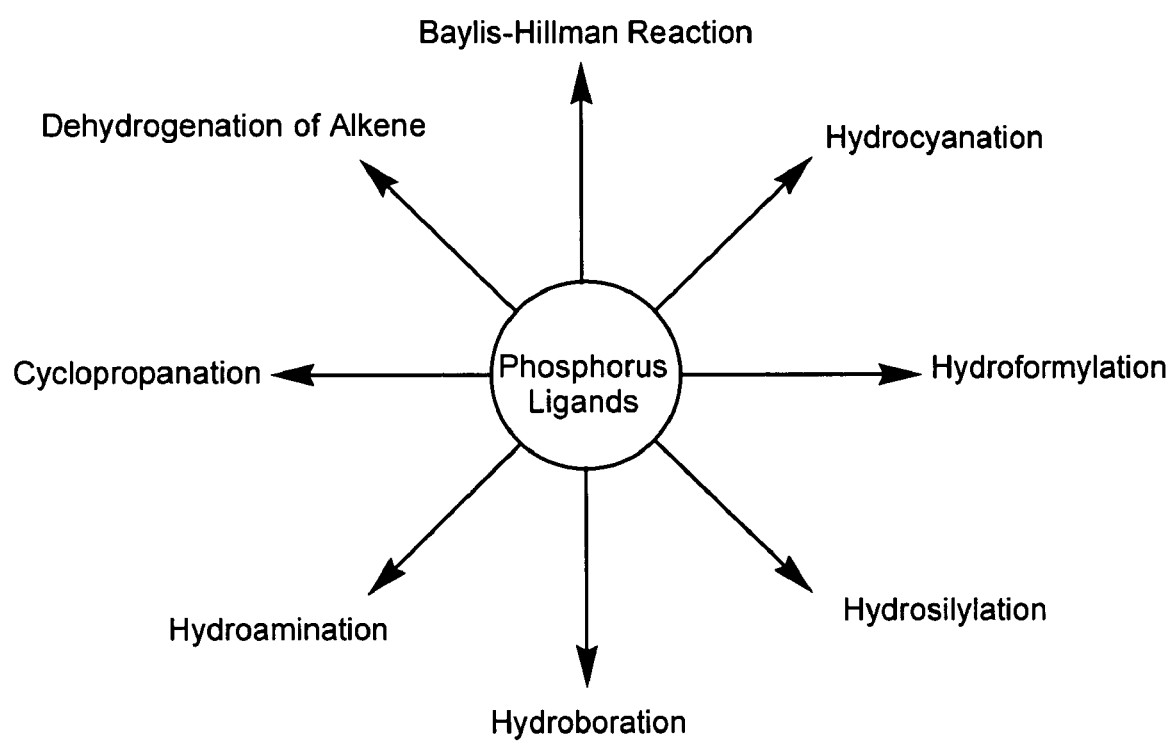
FIG. 3 is a diagram showing a few of the catalytic reactions that metal complexes with phosphorus ligands catalyze.
Figure 4:
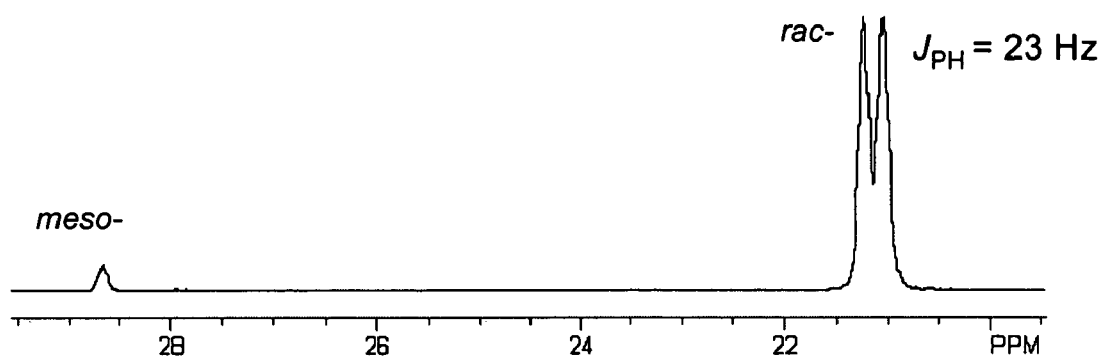
FIG. 4 is a $^{31}$P NMR spectrum ($^{1}$H coupled) of compound 1a with a rac:meso ratio of about 30:1.
Figure 5:
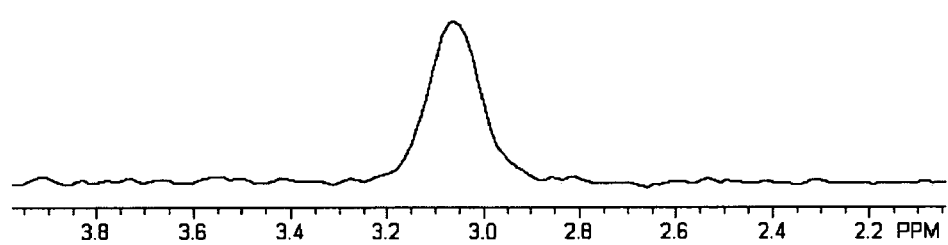
FIG. 5 is a $^{31}$P NMR spectrum ($^{1}$H coupled) of meso-3.
Figure 6:
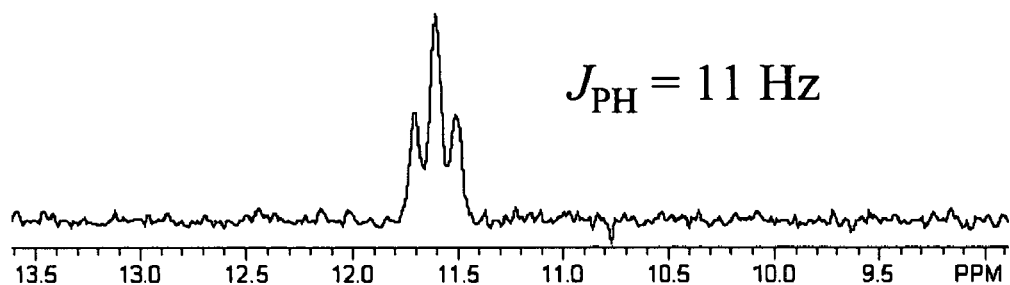
FIG. 6 is a $^{31}$P NMR spectrum ($^{1}$H coupled) of compound 7.
Figure 7:
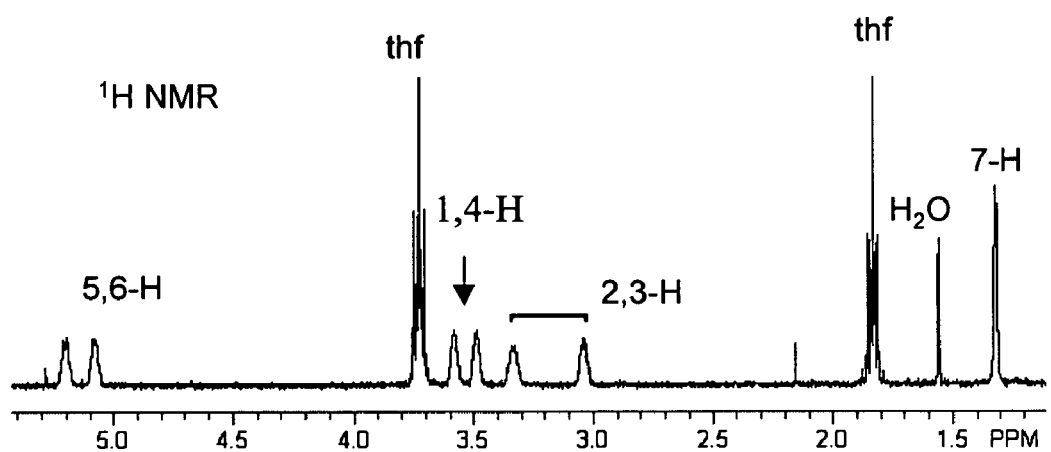
FIG. 7 is a $^{1}$H NMR spectrum of a Rh(NBD)(Cl) complex with compound rac-6b.

The diazaphosphacycles of the present invention may be combined with a transition metal to form a transition metal complex. Suitable diazaphosphacycles include those of formulas XI, XIA, XIB, XIC, XII, XIII, XIV, XIVA, XIVB, or XV. The transition metal complexes of the invention include a transition metal and a diazaphosphacycle where at least one phosphorus atom in the diazaphosphacycle is bonded to the transition metal. Preferred metal complexes are prepared using 3,4-diazaphospholanes. In certain transition metal complexes including a diazaphosphacycle of formula X or formula XV, two of the phosphorus atoms are bonded to the transition metal. Preferred transition metals in transition metal complexes include Rh, Ru, Pd, Pt, Ir, Ni, Co, and Fe. Pd and Rh are particularly preferred. Other preferred transition metal complexes have catalytic activity and can be used to catalyze transformations such as those carried out with known transition metal complexes as understood by those skilled in the art. Just a few of the catalytic transformations possible with the transition metal complexes of the present invention are shown in FIG. 3.

Inventive compounds may also be made on solid phase as well as in solution. Hence, in another aspect the invention provides compositions comprising a diazaphosphacycle as described herein (e.g., a compound of formula XI, XIA, XIB, XIC, XII, XIII, XIV, XIVA, XIVB, or XV.) and a solid support wherein the diazaphosphacycle is covalently attached to the solid support. It is to be understood that any solid support suitable for solid phase peptide or organic synthesis may be used in inventive compositions, including but not limited to a polymeric support resin, controlled pore glass, silica, alumina, or zeolite. Thus, it is well within the skill of the ordinary artisan to select a suitable solid support for the application at hand. Polymeric support resins are particularly suitable for inventive compositions and include any resins known to be stable to peptide and/or organic synthetic reactions such as, for example, polystyrene, polyethylene glycol, or polysaccharide. Typically, the resin-supported diazaphosphacycle is covalently attached at T and can include, e.g., a linker such as one comprising 2,2'-(ethylenedioxy)bis(ethylamino)-monosuccinamide, and the like. As with solid supports, such linkers are well known for use in solid phase peptide and organic synthesis and it is well within the skill of the ordinary artisan to select an appropriate linker for the application at hand based on the disclosure herein. Such linkers allow for easier characterization by $^1$H NMR and permit catalysis of reactions that approach or match solution phase selectives. Libraries of the invention therefore include those having at least one resin-supported diazaphosphacycle as described herein.

Figure 14:
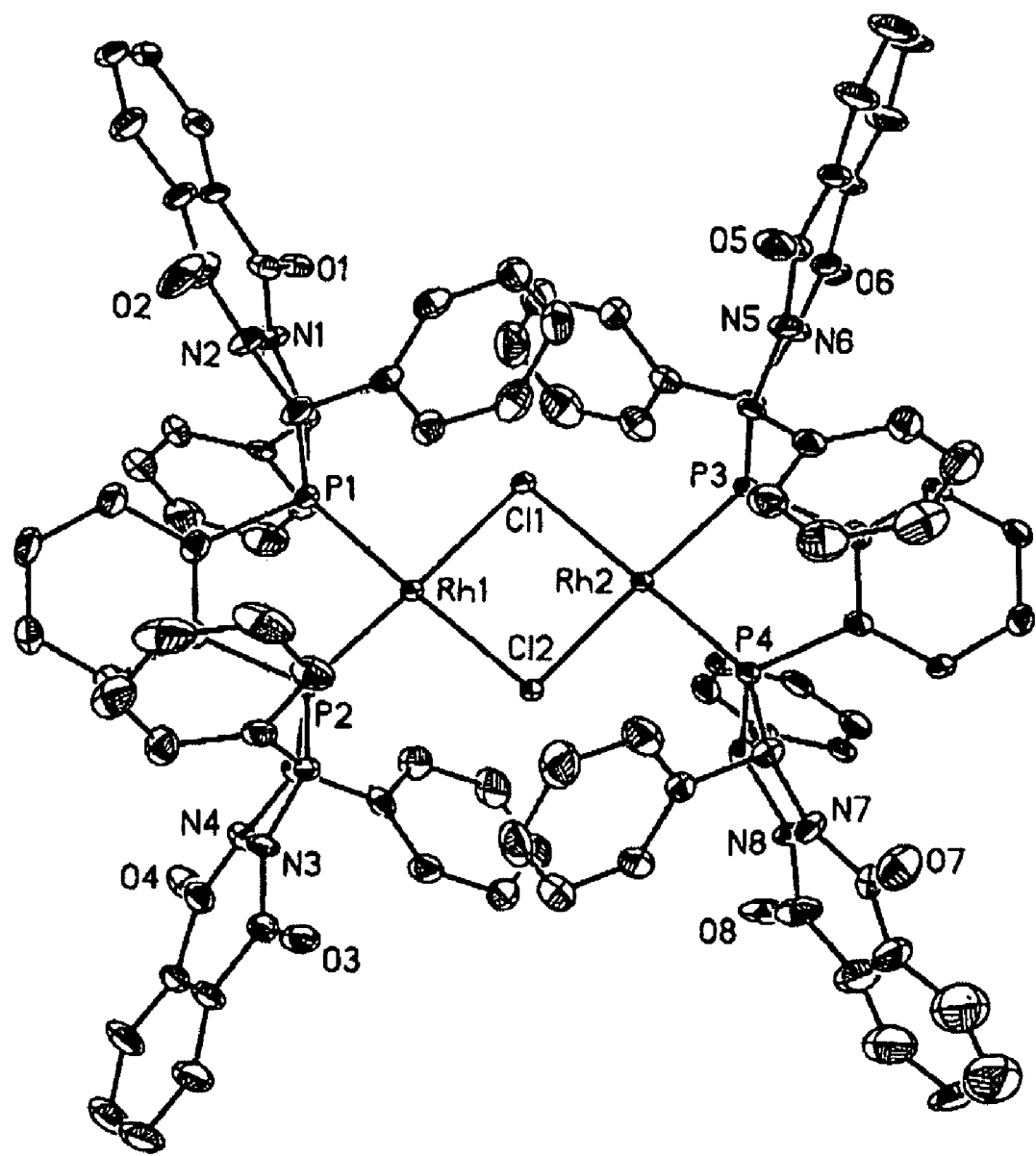
FIG. 14 is an X-ray crystal structure ORTEP diagram of [{1,2-bis(diazaphospholanes)benzene}RhCl]$_{2}$ where the 1,2-bis(diazaphospholane)benzene is compound 8.
Figure 15:
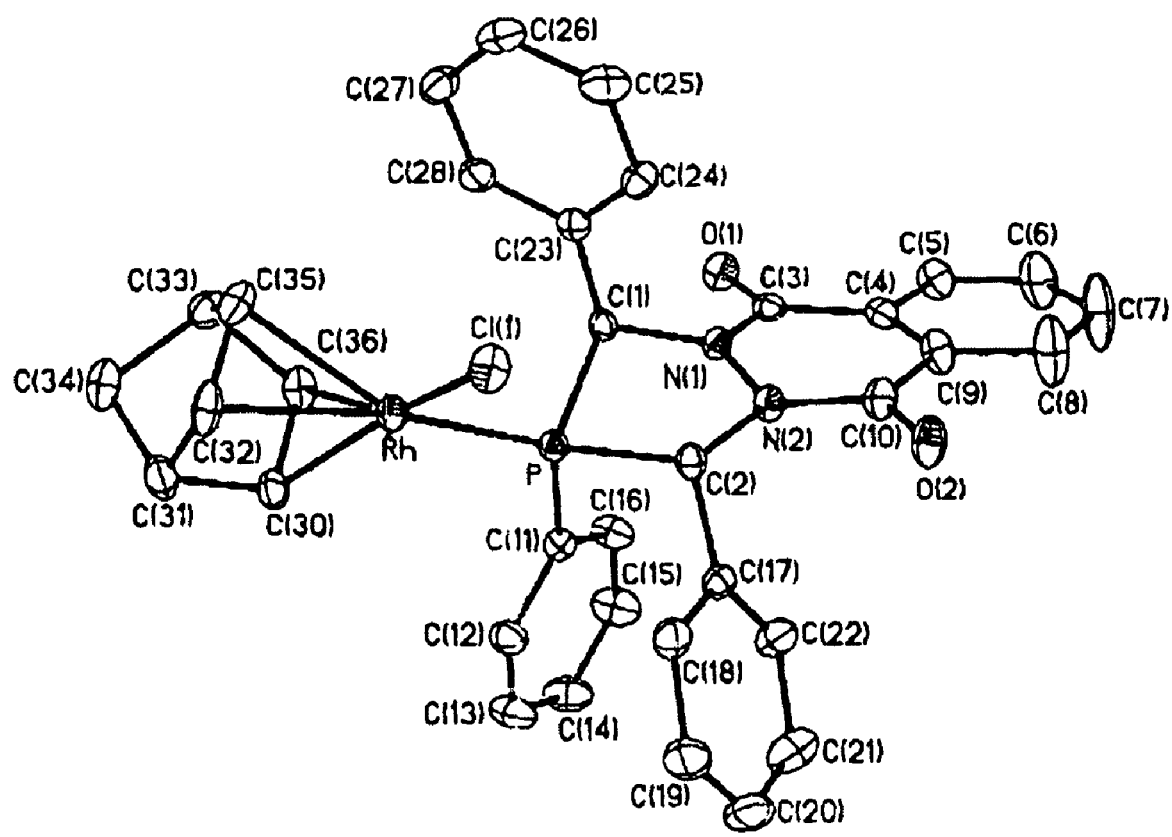
Figure 16:
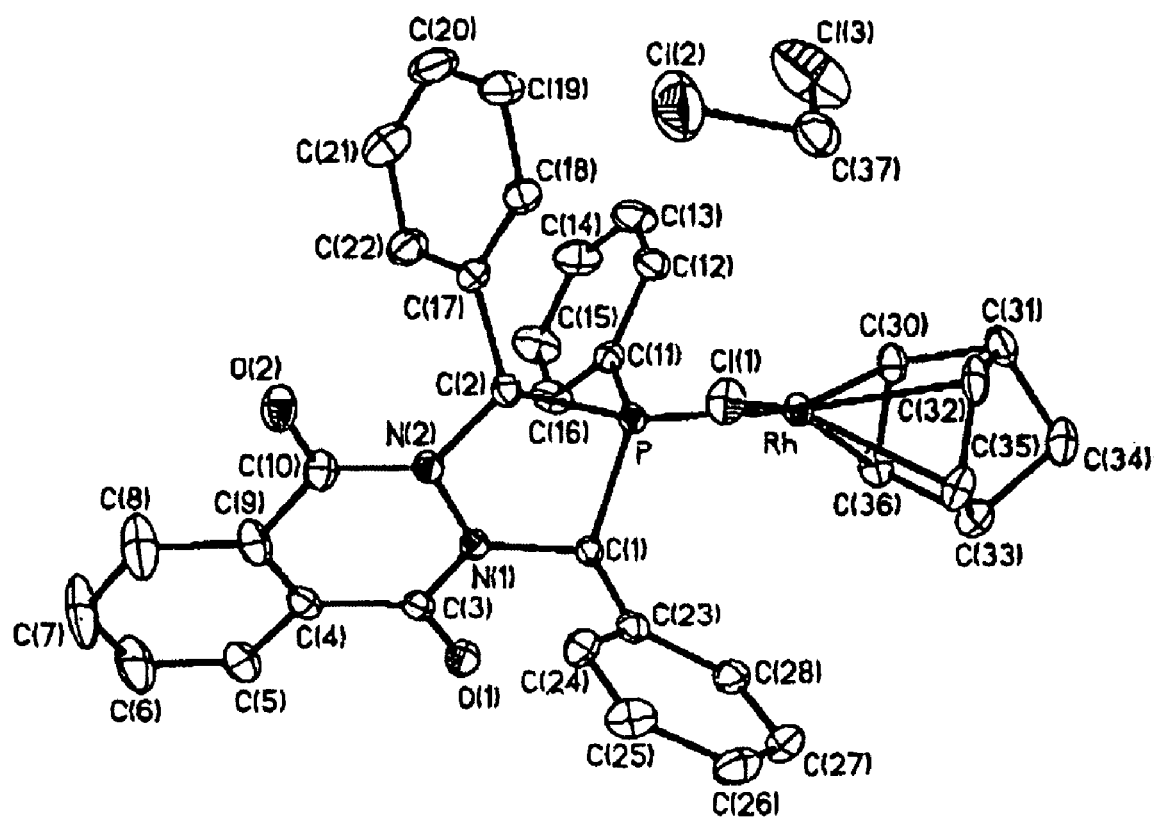
FIG. 16 is an X-ray crystal structure ORTEP diagram of a methylene chloride solvated Rh(NBD)(Cl) complex with a diazaphospholane (6).

Various methods may be used to prepare transition metal complexes from the diazaphosphacycles of the present invention. Such methods include reacting a diazaphosphacycle with a starting transition metal complex to produce the diazaphosphacycle transition metal complex. In such reactions, the starting transition metal complex typically includes at least one ligand that is replaced by the diazaphosphacycle during the reaction. Examples of ligands include phosphines; amines; diamines; CO; Cl, Br; nitriles such as, but not limited to acetonitrile and benzonitrile; 1,5-cyclooctadiene, norbornadiene, and other dienes; alkenes; ketones; alcohols; ethers; thiols; and sulfoxides. For example, excess diazaphospholanes 6a and 6b react with ½[{Rh(NBD)Cl}$_2$] affording adducts with the formula [(6)Rh(NBD)Cl] in quantitative yields. Similarly, reaction of the N,N'-phthaloyl derivative of 9 with [(COD)Pt(CH$_3$)$_2$] in solution yields [(9-phthaloyl)Pt(CH$_3$)$_2$] in quantitative yield as judged by NMR spectroscopy and X-ray crystallography. X-ray crystallography was used to generate ORTEP diagrams of various metal complexes as seen in FIGS. 14, 15, and 16. $^1$H and $^{31}$P NMR spectra of various metal complexes are shown in FIGS. 7, and 9-13.

Standard reaction conditions known to those skilled in the art may be used to promote formation of the transition metal complex. For example, CO displacement may be promoted through the use of ultraviolet irradiation or by reaction with trimethylamine N-oxide as known by those skilled in the art.

Scheme 7 shows methods for preparing Rh(norbornadiene) complexes that include one or two diazaphosphacycles of the present invention.

Scheme 7

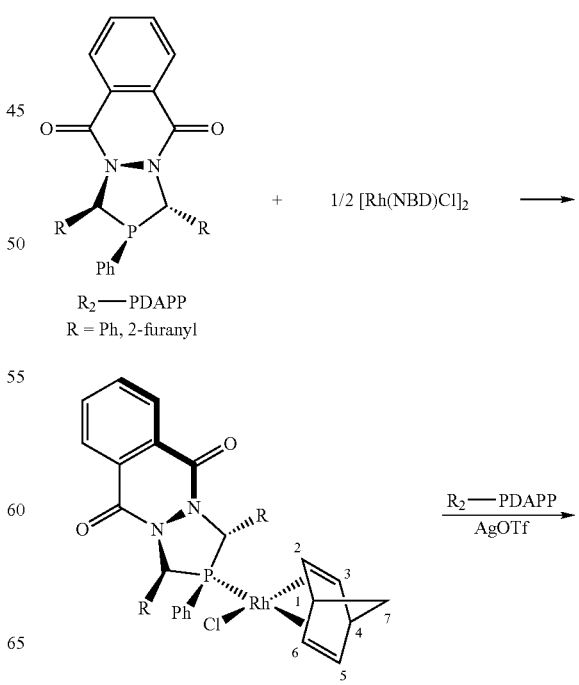

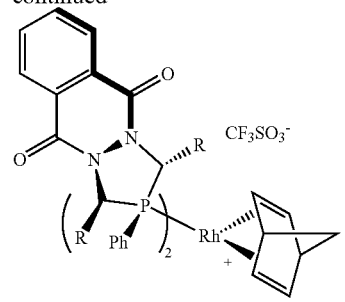
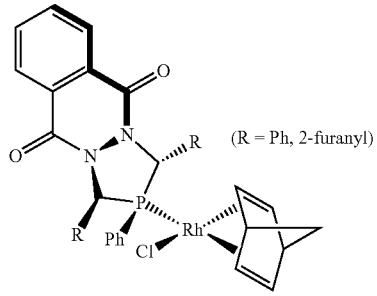
Scheme 8 shows various platinum complexes that have been synthesized using various diazaphosphacycles of the present invention
Scheme 8
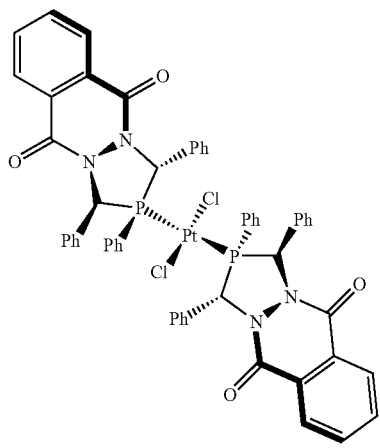
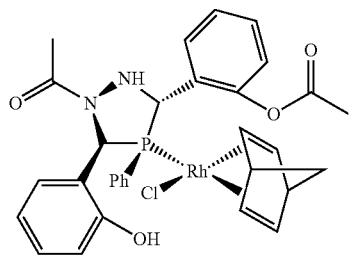
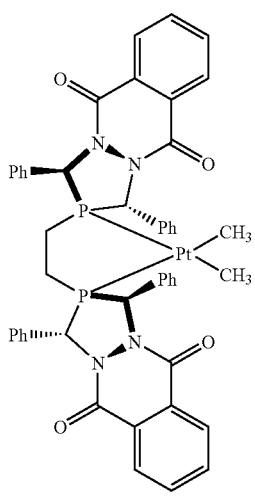
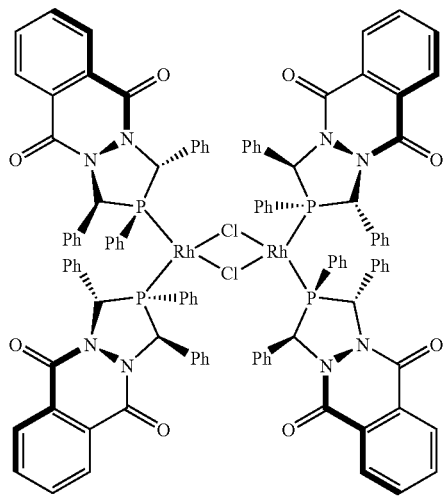
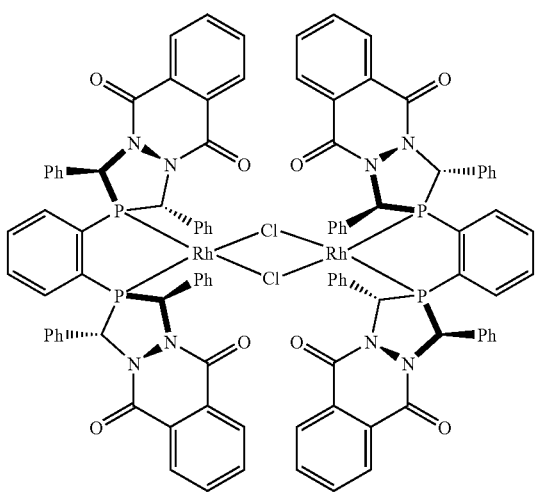
Scheme 9 shows various synthesized rhodium complexes that include the diazaphosphacycles of the present invention.

-continued

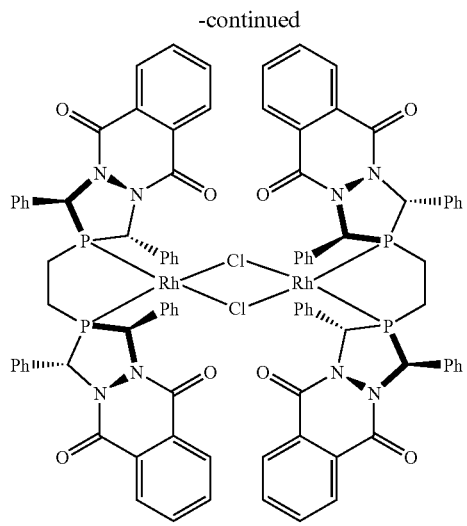

Scheme 10 shows a number of palladium complexes that have been synthesized using various diazaphosphacycles of the present invention.

Scheme 10

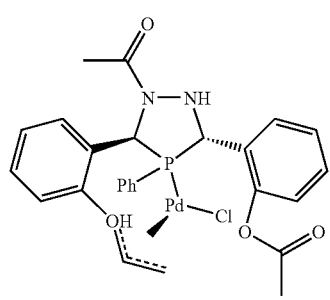

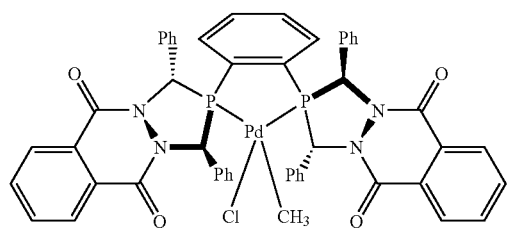

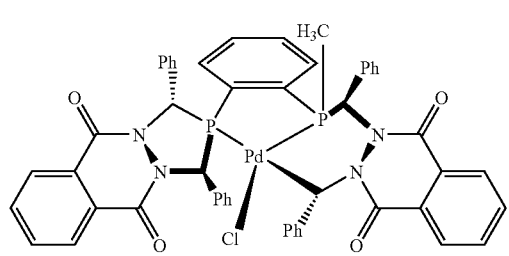

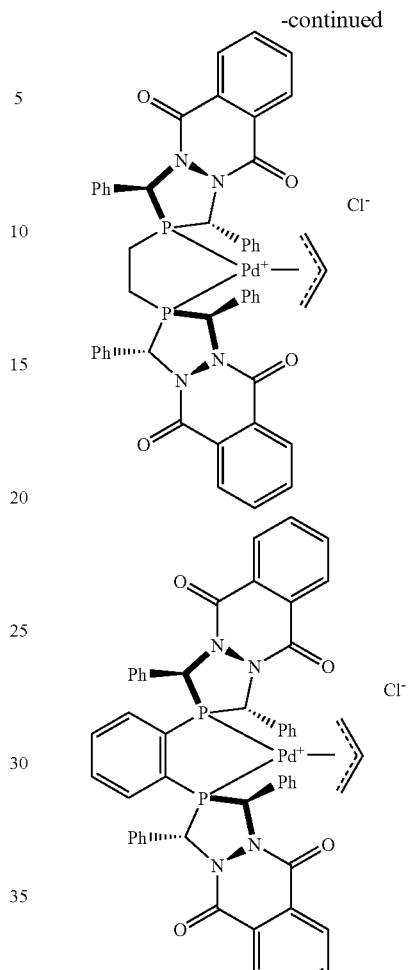

As noted above, there are many different types of reaction catalyzed by transition metal complexes. Examples of such reactions that may be catalyzed by the transition metal complexes of the present invention include, but are not limited to, alkene, alkyne, ketone, imine, oxime, aldehyde, nitrile, arene, carboxylic acid, ester, acid anhydride, and nitro group hydrogenations; hydrogenolysis reactions of alkyl halides, alkenyl halides, and acyl halides; hydrosilylation of alkenes, alkynes, ketones, and oximes; hydroboration of alkenes, alkynes, ketones, and oximes; hydroamination of alkenes and alkynes; hydroformylation of alkenes; hydroacylation of alkenes; hydrocarboxylation, hydroesterification, and hydrocarboxamidation of alkenes; carbonylation and double carbonylation of alkyl, aryl, and alkenyl halides; hydrocyanation of alkenes, dienes, and alkynes; alkene metathesis; cycloaddition of alkenes, dienes, and alkynes; cyclopropanation of alkenes; alkene and alkyne isomerization; Tischenko disproportionation of aldehydes; aziridination of alkenes; cross-coupling reactions; diborylation of alkanes; dehydrogenation of alkanes; allylic alkylation; allylic amination; allylic esterification; and amination and etherification of alkenyl and aryl halides. While each of the catalytic reactions is separately preferred, hydrogenation and allylic alkylation reactions are particularly preferred transformations where transition metal complexes prepared from the diazaphosphacycles of the present invention may be utilized. Especially preferred catalytic transformations include those where enantioselectivity is desired.

For example, as shown in Scheme 11, asymmetric hydrogenation of an acrylate derivative to give optically active N-acetyl-alanyl-methyl ester may be catalyzed by Rh and diazaphosphacycles having, e.g., formula XI. Typically, 0.01 to 5 mol % catalyst is used. The reaction may be performed at room temperature and atmospheric pressure or, for shorter reaction times, at elevated temperature (e.g. 35° C.) and under high pressure conditions (e.g. 150 pounds per square inch (psi) of hydrogen). Typical solvents for the reaction include methanol, tetrahydrofuran, methylene chloride, or other common organic solvents. One skilled in the art will readily appreciate that asymmetric hydrogenation as described herein may be practiced on a wide variety of acrylate derivatives including various alkyl, aryl, aralkyl esters, and the like as well as various 2- and 3-substituted derivatives.

Scheme 11

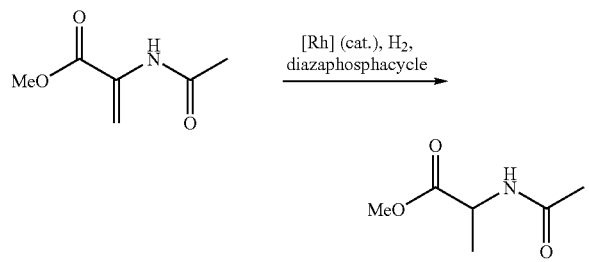

Cross-coupling reactions using Pd and invention diazaphosphacycles are also particularly preferred. As shown in Scheme 12, diazaphosphacycles of the present invention may be used in the Heck reaction with acrylates such as t-butyl acrylate to give predominately or exclusively the trans olefinic isomer. Standard conditions may be used such as those found in Hartwig et al. *J. Am. Chem. Soc.*, (1999) 121, 2123; Herrmann et al., *Chem. Eur. J.*, (1997), 3, 1357; and Fu et al., *J. Am. Chem. Soc.*, (2001), 123, 6989.

Scheme 12

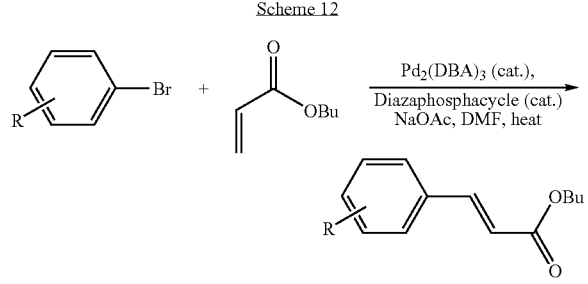

Further preferred are asymmetric allylic alkylation reactions catalyzed by a complex of a diazaphosphacycle of the present invention with Pd under the conditions shown in Scheme 13. The reactions are typically carried out at room temperature in the substantial absence of oxygen and in an organic solvent such as dichloromethane. Other possible reaction conditions may include temperatures from –50° C. to 65° C. although lower temperatures generally yield higher enantioselectivities. Water or common organic solvents such as tetrahydrofuran, toluene, N,N-dimethylformamide, and the like may be used as solvents. Other transition metals (Mo, Ir, Pt) may be used as catalysts in place of Pd. Typically, a base such as an alkali metal salt of acetate and a silylating agent such as N,O-bistrimethylsilylacetamide (BSA) are present. Other bases that may be used in the allylic alkylation include NaH, $Cs_2CO_3$, $K_2CO_3$, and $Rb_2CO_3$, or combinations such as BSA/[n-$Bu_4$N]Cl, BSA/[$(C_6H_{13})_4$N]Cl, and the like. In many instances, hexafluorophosphate salts such as $AgPF_6$ or $NaPF_6$ salt may be added to improve the yields and selectivities of this reaction.

Scheme 13

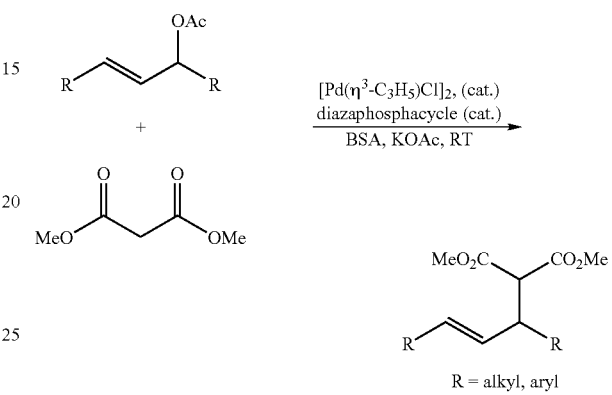

R = alkyl, aryl

As a general rule, 3,4-diazaphospholanes are bulky ligands. For example, the cone angle of 1a (172°) is comparable to that of tricyclohexylphosphine (170°). The bulkiness of the 3,4-diazaphosphacycles allows for the formation of transition metal complexes with crowded metal centers which may be associated with improved selectivity and/or activity during catalysis. Accordingly, diazaphosphacycles having cone angles greater than 170° are preferred.

EXAMPLES

General Considerations

Routine NMR characterization experiments, $^1$H NMR (300 and 500 MHz), $^{13}$C NMR (75.462 and 125.7 MHz), $^{19}$F NMR (282 MHz), and $^{31}$P NMR (121.49 and 202.4 MHz) were carried out on a Bruker AC-300 or a Varian 500 NMR spectrometer. $^1$H NMR data are reported as follows: chemical shift (multiplicity (b=broad, s=singlet, d=doublet, t=triplet, q=quartet, and m=multiplet), and integration). Chemical shifts for $^1$H NMR spectra are reported in ppm downfield from internal tetramethylsilane (TMS, δ scale) using residual protons in the deuterated solvents ($C_6D_6$, 7.15 ppm; $CDCl_3$, 7.25 ppm; and $CD_2Cl_2$, 5.31 ppm) as references. $^{13}$C and $^{31}$P NMR spectra were obtained using $^1$H decoupling, and the chemical shifts are reported in ppm vs. $Me_4Si$ ($CDCl_3$ at 77 ppm and $C_6D_6$ at 128 ppm) and 85% $H_3PO_4$ standard (external), respectively. Elemental analyses were provided by Desert Analysis (Phoenix, Ariz.).

$CDCl_3$ solvents were purchased from Aldrich Chemical (Milwaukee, Wis.), distilled over calcium hydride, and vacuum transferred into an air-tight solvent bulb prior to transfer into an inert-atmosphere glove bag. All reactions were carried out under a dry nitrogen atmosphere using standard Schlenk techniques unless otherwise noted.

Cyclohexyl phosphine and 1,2-bis(phosphino)ethane were purchased from Strem Chemicals, Inc. (Newburyport, Mass.) HCl (1.0 M in $Et_2O$ solution), succinyl chloride, phthaloyl chloride, and diethyl L-tartrate were purchased from Aldrich Chemical of Milwaukee, Wis. Acetyl chloride was purchased from J. T. Baker (Phillipsburg, N.J.).

The aryl azine derivatives (aryl-CH=N—N=CH-aryl) were prepared by reaction of the corresponding aldehyde (2 equiv.) with hydrazine under refluxing alcohol conditions. F. E. Hencoch, G. Hampton, C. R. Hauser, *J. Am. Chem. Soc.* 1969, 91, 676-681. The alkyl azine derivatives (alkyl-CH=N—N=CH-alkyl) (A. U. Blackham, N. L. Eatough, *J. Am. Chem. Soc.* 1962, 84, 2922-2930), phenylphosphine (R. C. Taylor, R. Kolodny, D. B. Walters, *Synthesis in Inorganic and Metal-Organic Chemistry* 1973, 3, 175-179), and o-bis (phosphino)benzene (E. P. Kyba, S.-T. Liu, R. L. Harris, *Organometallics* 1983, 2, 1877-1879) were prepared according to known literature methods. Phenylphosphine is commercially available from Aldrich Chemical (Milwaukee, Wis.).

General Synthesis for Compounds 1a-g and 5

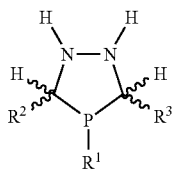

1a: $R^1$ = Ph; $R^2$ = $R^3$ = Ph
1b: $R^1$ = Ph; $R^2$ = $R^3$ = 2-furanyl
1c: $R^1$ = Ph; $R^2$ = $R^3$ = n-propyl
1d: $R^1$ = Ph; $R^2$ = $R^3$ = i-propyl
1e: $R^1$ = Ph; $R^2$ = $R^3$ = t-butyl
1f: $R^1$ = Cyclohexyl; $R^2$ = $R^3$ = Ph
1g: $R^1$ = Cyclohexyl; $R^2$ = $R^3$ = 2-furanyl

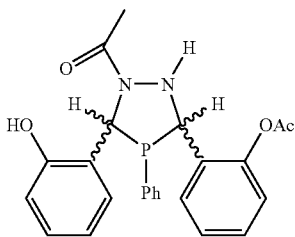

5

A diethyl ether (20 mL) solution of the appropriate azine derivative (4.55 mmol) was treated with HCl (ca. 4.75 mL, 4.75 mmol, 1.0 M in $Et_2O$ solution) at 0° C. Immediately, a white solid precipitated from solution. Phenyl (or cyclohexyl for compounds 1f and 1g) phosphine (4.55 mmol) was added to this suspension at 0° C. and the reaction mixture was stirred for 4 hours (or overnight) at room temperature. Into the resultant white slurry was added a degassed 10% aqueous $K_2CO_3$ (ca 30 mL) solution at 0° C. The ether layer was separated via cannula, dried over $MgSO_4$, and filtered via cannula to obtain a colorless solution. The ether was evaporated under vacuum to yield the corresponding diazaphospholanes.

rac-1a: Yield=67% of a white solid (rac/meso=13). $^1$H NMR ($CDCl_3$): δ 4.53 (b, 2H, NH), 5.11 (d, $J_{H-P}$=22.1 Hz, 1H, PCHN), 5.54 (s, 1H, PCHN), 6.77 (m, 2H, Ph), 6.98 (m, 3H, Ph), 7.10-7.39 (m, 10H, Ph); $^{13}$C{$^1$H} NMR ($CDCl_3$): δ 71.51 (d, $J_{C-P}$=1.2 Hz, PCHN), 71.81 (d, $J_{C-P}$=5.7 Hz, PCHN), 126.29 (d, $J_{C-P}$=4.4 Hz, Ph), 126.37 (d, $J_{C-P}$=1.3 Hz), 127.30 (s), 127.41 (s), 127.86 (s), 128.15 (d, $J_{C-P}$=6.3 Hz), 128.94 (s), 128.98 (s), 133.34 (d, $J_{C-P}$=18 Hz), 134.53 (s), 141.10 (d, $J_{C-P}$=15.3 Hz), one quaternary carbon hasn't been assigned due to the overlap; $^{31}$P NMR ($CDCl_3$): δ 21.4 (d, $J_{P-H}$=23 Hz). Analysis calculated for $C_{20}H_{19}N_2P$: C, 75.46; H, 6.02; N, 8.8. Found: C, 74.85; H, 6.09; N, 8.8.

rac-1b: Yield=90% of a colorless oil (rac/meso=10). $^1$H NMR ($CDCl_3$): δ 4.0 (b, 1H, NH), 4.25 (b, 1H, NH), 4.84 (d, $J_{H-P}$=22.8 Hz, 1H, PCHN), 5.24 (d, $J_{H-P}$=2.2 Hz, 1H, PCHN), 5.63 (m, 1H, furan), 6.1 (dd, J=1.8, 3.3 Hz, 1H, furan), 6.31 (m, 1H, furan), 6.36 (m, 1H, furan), 7.12 (m, 1H, furan), 7.33 (m, 5H, Ph), 7.42 (m, 1H, furan); $^{13}$C{$^1$H} NMR ($CDCl_3$): δ 64.46 (d, J=20.3 Hz, PCHN), 65.55 (d, J=24.8 Hz, PCHN), 106.28 (d, J=3.2 Hz, furan), 107.13 (d, J=7 Hz, furan), 110.04 (s, furan), 110.55 (s, furan), 128.33 (d, J=7 Hz, Ph), 129.43 (s, Ph), 133.17 (d, J=18.5 Hz, Ph), 141.23 (s, furan), 142.62 (s, furan), 148 01 (furan), 150.09 (s, furan), 153.26 (d, J=14 Hz, Ph); $^{31}$P NMR ($CDCl_3$): δ 9.9 (d, $J_{P-H}$=23 Hz). Analysis calculated for $C_{16}H_{15}O_2N_2P$: C, 64.43; H, 5.07; N, 9.39. Found: C, 64.59; H, 5.14; N, 8.70.

rac-1c: Yield=>90% of a white solid (rac/meso=5). $^1$H NMR ($CDCl_3$): δ 0.82 (t, $J_{H-H}$=7.3 Hz, 3H, $CH_3$), 0.94 (t, $J_{H-H}$=7.3 Hz, 3H, $CH_3$), 1.3-1.7 (m, 8H, $CH_2$), 3.15 (doublet of triplets, $J_{H-H}$=7.0 Hz, $J_{P-H}$=16.2 Hz, 1H, CH), 3.94 (t, $J_{H-H}$=6.5 Hz, 1H, CH), 3.3-3.6 (b, 2H, NH) 7.34-7.41, (m, 3H, Ph), 7.47-7.55 (m, 2H, Ph); $^{13}$C{$^1$H} NMR ($CDCl_3$): δ 13.9 (s, $CH_3$), 21.5 (d, $J_{P-C}$=12.0 Hz), 22.0 (d, $J_{P-C}$=6.6 Hz), 37.0 (d, $J_{P-C}$=22.8 Hz), 67.0 (d, $J_{P-C}$=21.1 Hz, PCHN), CH (δ67.3 (d, $J_{P-C}$=17.0 Hz, PCHN), 126.2 (d, $J_{P-C}$=6 Hz, $C_{meta}$), 127.0 (s, $C_{para}$), 133.8 (d, $J_{P-C}$=12 Hz, $C_{ortho}$), 136.8 (d, $J_{P-C}$=30 Hz, $C_{ipso}$); $^{31}$P NMR ($CDCl_3$): δ 1.1 (b). Analysis calculated for $C_{14}H_{23}N_2P$(hexane)$_{0.1}$: C, 67.72; H, 9.5; N, 10.82. Found: C, 68.12; H, 8.94; N, 10.72.

rac-1d: Yield=70% of a white solid with mainly a rac isomer. $^1$H NMR ($CDCl_3$): δ 0.9-1.13 (m, 13H, CH and $CH_3$), 1.94 (m, 1H, CH), 2.81 (dd, $J_{H-H}$=9.0 Hz, $J_{P-H}$=26.4 Hz, 1H, PCHN), 3.82 (dd, $J_{H-H}$=6.3 Hz, $J_{P-H}$=1.9 Hz, 1H, PCHN), 3.2-3.6, (b, 2H, NH), 7.34-7.41, (m, 3H, Ph), 7.47-7.55, (m, 2H, Ph); $^{13}$C{$^1$H} NMR ($C_6D_6$): δ 20.7, (d, $J_{C-P}$=13.7 Hz, $CH_3$), 21.4, (d, $J_{C-P}$=8.5 Hz, $CH_3$), 22.5 (d, $J_{C-P}$=4.8 Hz, $CH_3$), 23.5, (d, $J_{C-P}$=21.4 Hz, $CH_3$), 28.4 (s), 31.9 (d, $J_{C-P}$=20 Hz), 65.4 (d, $J_{C-P}$=18 Hz), 67.5 (d, $J_{C-P}$=32 Hz), 77.1 (d, $J_{C-P}$=18.1 Hz, PCHN), 128.6 (d, $J_{C-P}$=7 Hz, $C_{meta}$), 129.1 (s, $C_{para}$), 134.9 (d, $J_{C-P}$=19 Hz, $C_{ortho}$), 135.9 (d, $J_{C-P}$=26 Hz, $C_{ipso}$); $^{31}$P NMR ($CDCl_3$): δ −5.7 (d, $J_{P-H}$=2.4 Hz). Analysis calculated for $C_{14}H_{23}N_2P(CH_2Cl_2)_0$.0.1: C, 65.43; H, 9.04; N, 10.89. Found: C, 65.34; H, 8.61; N, 10.33.

rac-1e: Yield=61% of a white solid (rac/meso=6). $^1$H NMR ($CDCl_3$): δ 0.75 (d, $J_{H-P}$=1.1 Hz, 9H, $CH_3$), 1.04 (s, 9H, $CH_3$), 2.74 (d, $J_{H-P}$=21.3 Hz, PCHN), 3.81 (d, $J_{H-P}$=2.6 Hz, 1H, PCHN), 7.34 (m, 3H, Ph), 7.58 (m, 2H, Ph); $^{13}$C{$^1$H} NMR ($CDCl_3$): δ 28.11 (d, $J_{C-P}$=8.6 Hz, $CH_3$), 29.27 (d, $J_{C-P}$=4.9 Hz, $CH_3$), 33.05 (s, $CCH_3$), 33.78 (d, $J_{C-P}$=15.9 Hz, $CCH_3$), 79.54 (d, $J_{C-P}$=26.5 Hz, PCHN), 81.10 (d, $J_{C-P}$=19 Hz, PCHN), 128.55 (d, $J_{C-P}$=7.6 Hz, $C_{ortho}$), 129.31 (s, $C_{para}$), 135.13 (d, $J_{C-P}$=19.7 Hz, $C_{meta}$), 136.49 (d, $J_{C-P}$=25.4 Hz, $C_{ipso}$); $^{31}$P NMR ($CDCl_3$): δ −13.1 (d, $J_{P-H}$=19.8 Hz). Analysis calculated for $C_{16}H_{27}N_2P$: C, 69.03; H, 9.78; N, 10.06. Found: C, 69.3; H, 9.77; N, 9.91.

rac-1f: Yield=58% of a white solid with mainly a rac isomer. $^1$H NMR ($CDCl_3$): δ 0.47 (m, 1H), 0.80 (m, 2H), 1.16-1.7 (m, 8H), 3.78 (b, 1H, NH), 4.14 (b, 1H, NH), 4.78 (s, 1H, PCHN), 4.85 (d, $J_{H-P}$=19.1 Hz, 1H, PCHN), 7.22-7.40 (m, 8H, Ph), 7.47-7.50 (m, 2H, Ph); $^{13}$C{$^1$H} NMR ($CDCl_3$): 26.2 (s), 26.3 (d, $J_{C-P}$=12.8 Hz), 26.9 (d, $J_{C-P}$=7.7 Hz), 29.0 (d, $J_{C-P}$=8.3 Hz), 30.7 (d, $J_{C-P}$=19.5 Hz), 32.2 (d, $J_{C-P}$=21.6 Hz), 70.62 (d, $J_{C-P}$=3.2 Hz, PCHN), 71.0 (s, PCHN), 126.4 (d, $J_{C-P}$=3.2 Hz, Ph), 126.8 (s, Ph), 127.4 (d, $J_{C-P}$=1.3 Hz, Ph), 127.7 (d, $J_{C-P}$=9.5 Hz, Ph), 128.4 (s, Ph), 128.8 (s, Ph), 136.4 (s, CCH), 140.4 (d, $J_{C-P}$=15.9 Hz, CCH); $^{31}$P NMR ($CDCl_3$):

δ 11.68 (m). Analysis calculated for $C_{20}H_{25}N_2P$: C, 74.05; H, 7.77; N, 8.64. Found: C, 74.4; H, 8.11; N, 9.67.

rac-1g: Yield=61% of a white solid with mainly a rac isomer. $^1$H NMR (CDCl$_3$): δ 0.59 (m, 1H), 0.97 (m, 2H), 1.14-1.24 (m, 3H), 1.51-1.73 (m, 5H), 3.95 (b, 2H, NH), 4.74 (d, $J_{H\text{-}P}$=3.3 Hz, 1H, PCHN), 4.82 (d, $J_{H\text{-}P}$=22.8 Hz, PCHN), 6.23 (m, 1H), 6.29-6.35 (m, 3H), 7.37-7.39 (m, 2H); $^{13}$C{$^1$H} NMR (CDCl$_3$): δ 26.21 (s, CH$_2$), 26.47 (d, $J_{C\text{-}P}$=12.1 Hz), 26.75 (d, $J_{C\text{-}P}$=8.3 Hz), 29.25 (d, $J_{C\text{-}P}$=10.2 Hz), 30.35 (d, $J_{C\text{-}P}$=19.1 Hz), 33.07 (d, $J_{C\text{-}P}$=30.0 Hz), 64.29 (d, $J_{C\text{-}P}$=28.6 Hz, PCHN), 65.0 (d, $J_{C\text{-}P}$=23.5 Hz, PCHN), 106.54 (d, $J_{C\text{-}P}$=2.6 Hz, furan), 107.25 (d, $J_{C\text{-}P}$=7.0 Hz, furan), 110.36 (s, furan), 110.63 (s, furan), 141.56 (s, furan), 142.52 (s, furan), 149.65 (s, PCCH), 153.11 (d, $J_{C\text{-}P}$=20.4 Hz, PCCH), $^{31}$P NMR (CDCl$_3$): δ 15.6 (d, $J_{P\text{-}H}$=21.3 Hz). Analysis calculated for $C_{16}H_{21}N_2O_2P$: C, 63.15; H, 6.96; N, 9.2. Found: C, 63.26; H, 7.11; N, 9.25.

rac-5: Yield=79% of the crude product. X-ray quality crystals were grown from CH$_2$Cl$_2$/hexanes at room temperature. $^1$H NMR (CDCl$_3$): δ 2.50 (s, 3H, CH$_3$), 2.51 (s, 3H, CH$_3$), 5.04 (d, J=8.8 Hz, 1H, NH), 5.53 (dd, J=17.3, 8.8, Hz, 1H, PCHN), 6.32 (d, J=2.6 Hz, 1H, PCHN), 6.85-7.20 (m, 11H, Ph), 7.28 (m, 1H, Ph), 7.43 (m, 1H, Ph), 9.50 (b, 1H, OH); $^{13}$C{$^1$H} NMR (CDCl$_3$): δ 21.45 (s, CH$_3$), 21.77 (s, CH$_3$), 58.07 (d, $J_{C\text{-}P}$=19.7 Hz, PCHN), 61.40 (d, $J_{C\text{-}P}$=28.61 Hz, PCHN), 146.34 (s, Ph), 156.67 (d, $J_{C\text{-}P}$=5.5 Hz, Ph), 168.96 (s, CO), 171.17 (s, CO); Peaks at 118-135 ppm have not been assigned due to the complexity. $^{31}$P NMR (CDCl$_3$): δ 14.6 (m). Analysis calculated for $C_{24}H_{23}N_2O_4P(CH_2Cl_2)_{0.25}$: C, 63.92; H, 5.2; N, 6.15. Found: C, 64.27; H, 4.96; N, 6.41.

Synthesis of Compounds 2a and 2b

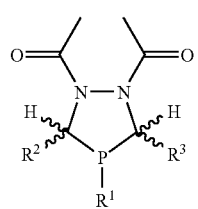

2a: $R^1$ = Ph; $R^2$ = $R^3$ = 2-furanyl
2b: $R^1$ = Cyclohexyl; $R^2$ = $R^3$ = 2-furanyl The appropriate azine (1.55 mmol) in Et$_2$O (50 mL) was treated with acetyl chloride (15.5 mmol, 10 equiv.) at 0° C. The appropriate phosphine (phenylphosphine (2a); cyclohexylphosphine (2b)) (1.55 mmol) was then slowly added at 0° C., and the mixture stirred at room temperature overnight. To the resultant white slurry was added 10% aqueous K$_2$CO$_3$ (ca. 20 mL) at 0° C. For 2a, the aqueous and organic layers were filtered off via cannula to obtain a white solid which was then washed with distilled water and Et$_2$O. X-Ray quality crystals were obtained from CH$_2$Cl$_2$ and hexane at room temperature. For 2b, the ether layer was separated, dried over MgSO$_4$, and filtered off via cannula to obtain a colorless solution. The ether was then removed under reduced pressure to yield the corresponding diazaphospholane.

rac-2a: Yield=80% with a white solid with a mainly rac isomer. $^1$H NMR (CDCl$_3$): δ 1.71 (s, 3H, CH$_3$), 2.21 (s, 3H, CH$_3$), 5.9 (dd, J=3.3, 1.8 Hz, 1H, furan), 6.03 (d, J=3.3 Hz, 1H, furan), 6.30 (dd, J=3.3, 1.8 Hz, 1H, furan), 6.44 (d, J=3.3 Hz, 1H, furan), 6.55 (d, $J_{H\text{-}P}$=23.2 Hz, 1H, NCHP), 6.72 (d, $J_{H\text{-}P}$=3.3 Hz, NCHP), 6.74 (m, 1H, furan), 7.11-7.22 (m, 5H, Ph), 7.39 (m, 1H, furan); $^{13}$C{$^1$H} NMR (CDCl$_3$): δ 19.08 (s, CH$_3$), 20.68 (s, CH$_3$), 52.72 (d, $J_{C\text{-}P}$=19.7 Hz, NCHP), 56.75 (d, $J_{C\text{-}P}$=31.2 Hz, NCHP), 108.24 (d, $J_{C\text{-}P}$=2.5 Hz, furan), 109.91 (s, furan), 110.53 (d, $J_{C\text{-}P}$=10.2 Hz, furan), 110.83 (s, furan), 128.03 (d, $J_{C\text{-}P}$=7.0 Hz, $C_{meta}$), 129.38 (s, $C_{para}$), 132.51 (d, $J_{C\text{-}P}$=20.3 Hz, $C_{ortho}$), 141.86 (s, furan), 143.51 (s, furan), 150.21 (d, $J_{C\text{-}P}$=32.4 Hz, $C_{ipso}$), 171.80 (s, CO), 174.75 (s, CO), two carbons are not assigned probably due to the overlap; $^{31}$P NMR (CDCl$_3$): δ 23.5 (d, $J_{P\text{-}H}$=22.9 Hz). Analysis calculated for $C_{20}H_{19}N_2O_4P$: C, 62.83; H, 5.01; N, 7.33. Found: C, 62.91; H, 4.65; N, 7.21.

rac-2b: Yield=25% a white solid with mainly a rac isomer. $^1$H NMR (CDCl$_3$): δ 0.43 (m, 1H), 0.75-1.0 (m, 2H), 1.1-1.3 (m, 3H), 1.5-1.8 (m, 5H), 1.68 (s, 3H, CH$_3$), 2.22 (s, 3H, CH$_3$), 6.2-6.4 (m, 6H, furan and PCHN), 7.3-7.4 (m, 2H, furan); $^{13}$C{$^1$H} NMR (CDCl$_3$): δ 19.42 (s, CH$_3$), 20.50 (s, CH$_3$), 26.00 (s), 26.29 (d, $J_{C\text{-}P}$=2.6 Hz), 26.44 (d, $J_{C\text{-}P}$=5.1 Hz), 29.13 (d, $J_{C\text{-}P}$=19.1 Hz), 29.88 (d, $J_{C\text{-}P}$=12.8 Hz), 32.39 (d, $J_{C\text{-}P}$=19.1 Hz), 52.83 (d, $J_{C\text{-}P}$=22.9 Hz, PCHN), 54.29 (d, $J_{C\text{-}P}$=33.1 Hz, PCHN), 108.80 (s, furan), 110.27 (d, $J_{C\text{-}P}$=9.5 Hz, furan), 110.72 (s, furan), 110.88 (s, furan), 142.15 (s, furan), 143.14 (s, furan), 149.56 (d, $J_{C\text{-}P}$=3.2 Hz, furan), 150.75 (d, $J_{C\text{-}P}$=26.71 Hz, furan), 173.15 (s, CO), 174.77 (s, CO); $^{31}$P NMR (CDCl$_3$): δ 27.0 (m). Analysis calculated for $C_{20}H_{25}N_2O_4P$: C, 61.85; H, 6.49; N, 7.21. Found: C, 62.18; H, 6.79; N, 7.30.

Synthesis of Compounds 3, 4, and 6

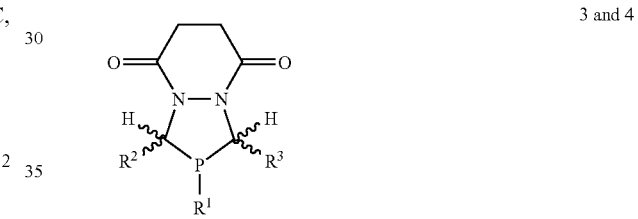

3: $R^1$ = Ph; $R^2$ = $R^3$ = ferrocene
4a: $R^1$ = $R^2$ = $R^3$ = Ph
4b: $R^1$ = cyclohexyl; $R^2$ = $R^3$ = 2-furanyl

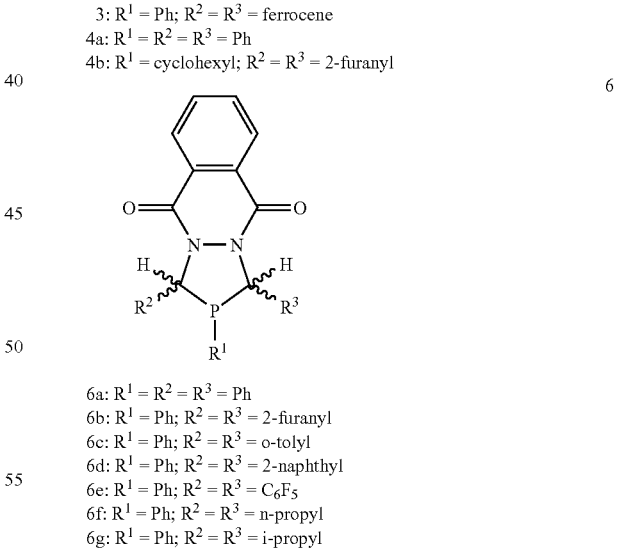

6a: $R^1$ = $R^2$ = $R^3$ = Ph
6b: $R^1$ = Ph; $R^2$ = $R^3$ = 2-furanyl
6c: $R^1$ = Ph; $R^2$ = $R^3$ = o-tolyl
6d: $R^1$ = Ph; $R^2$ = $R^3$ = 2-naphthyl
6e: $R^1$ = Ph; $R^2$ = $R^3$ = $C_6F_5$
6f: $R^1$ = Ph; $R^2$ = $R^3$ = n-propyl
6g: $R^1$ = Ph; $R^2$ = $R^3$ = i-propyl The appropriate azine (1.55 mmol) in Et$_2$O (50 mL) was treated with the diacid dichloride (4.65 mmol, 3 equiv.) at 0° C. The phosphine (1.55 mmol) was then slowly added at 0° C., and the mixture was stirred at room temperature overnight. To the resultant white slurry was added a 10% aqueous K$_2$CO$_3$ solution (ca. 20 mL) at ice-bath temperature. For 3, 4, 6a, 6b, and 6d, the aqueous and organic layers were filtered off via cannula to obtain a white solid. Subsequently, the product was washed with distilled water and Et$_2$O, and the residue was dried in vacuo to obtain an analytically pure product. For 6c, 6e, 6f and 6g, the ether layer was separated, dried over MgSO$_4$, and filtered off by cannula yielding the corresponding ether solution. The ether was removed in vacuo to obtain the desired product. Compounds 6 can also be made from the addition of corresponding compound 1 into a THF solution of phthaloyl chloride (3 equivalents) at ice-bath temperature. The mixture was stirred overnight at room temperature, placed under reduced pressure, washed with Et$_2$O and degassed water, and dried overnight to yield the corresponding compound 6.

meso-3: Yield=69% of a reddish brown solid (rac/meso=0.6). X-ray quality crystals of meso-3 were grown from CH$_2$Cl$_2$/hexane at room temperature. $^1$H NMR (CDCl$_3$): δ 2.50-2.6 (m, 2H, CH$_2$), 2.65-2.77 (m, 2H, CH$_2$), 3.88 (m, 2H, Cp), 4.0 (m, 2H, Cp), 4.04 (m, 2H), 4.14 (s, Cp, 10H) 4.30 (m, 2H, Cp), 6.04 (s, 2H, CHN), 7.45 (m, 5H, Ph); $^{13}$C{$^1$H} NMR (CDCl$_3$): δ 29.3 (s, CH$_2$), 59.4 (d, $J_{C-P}$=24.2 Hz, PCHN), 67.73 (s, CH), 68.12 (s CH), 68.62 (d, $J_{C-P}$=10.8 Hz, PCHN), 69.1 (s, Cp), 70.4 (d, $J_{C-P}$=3.8 Hz, CH), 85.05 (d, $J_{C-P}$=19.7 Hz, CCH), 129.2 (d, $J_{C-P}$=6.4 Hz, C$_{meta}$), 129.94 (s, C$_{para}$), 130.8 (d, $J_{C-P}$=15.8 Hz, C$_{ortho}$), 134.2 (d, $J_{C-P}$=23.5 Hz, C$_{ipso}$), 165.2 (s, CO); $^{31}$P NMR (CDCl$_3$): δ 3.0 (s). Analysis calculated for C$_{32}$H$_{29}$N$_2$O$_2$Fe$_2$P(CH$_2$Cl$_2$)$_{0.5}$ C, 59.63; H, 4.55; N, 4.21. Found: C, 60.19 (61.10); H, 4.60 (4.37); N, 4.36 (4.36).

rac-4a: Yield=95% of the crude product with mainly a rac isomer. X-ray quality crystals were grown from CH$_2$Cl$_2$/hexanes at room temperature. $^1$H NMR (CDCl$_3$): δ 2.83 (m, 4H, CH$_2$) 5.82 (d, $J_{H-P}$=19.1 Hz, 1H, PCHN), 6.51 (s, 1H, PCHN), 6.71-6.75 (m, 2H, Ph), 6.9-7.05 (m, 5H, Ph), 7.1-7.2 (m, 2H, Ph), 7.25-7.30 (m, 1H, Ph), 7.30-7.38 (m, 3H, Ph), 7.42-7.46 (m, 2H, Ph); $^{13}$C NMR (CDCl$_3$): δ 29.46 (s, CH$_3$), 30.38 (s, CH$_3$), 57.14 (d, $J_{C-P}$=21.0 Hz, PCHN), 61.72 (d, $J_{C-P}$=31.8 Hz, PCHN), 124.79 (d, $J_{C-P}$=1.9 Hz, Ph), 125.41 (d, $J_{C-P}$=8.3 Hz, Ph), 126.57 (s,Ph), 127.85 (s, Ph), 128.10 (d, $J_{C-P}$=6.4 Hz, Ph), 129.07 (s, Ph), 129.72 (s, Ph), 130.15 (d, $J_{C-P}$=24.2 Hz, Ph), 132.20 (d, $J_{C-P}$=19.0 Hz, Ph), 133.53 (s, Ph), 137.10 (d, $J_{C-P}$=15.3 Hz, Ph), 165.24 (s, CO), 167.71 (s, CO), one peak is not assigned due to the overlap; $^{31}$P NMR (CDCl$_3$): δ 11.6 (m). Analysis calculated for C$_{24}$H$_{21}$N$_2$O$_2$P: C, 71.99; H, 5.29; N, 7.0. Found: C, 71.21; H, 5.29; N, 6.96.

rac-4b: Yield=59% of the crude product with mainly a rac isomer. X-ray quality crystals were grown from CH$_2$Cl$_2$/hexanes at room temperature. $^1$H NMR (CDCl$_3$): δ 0.75 (m, 1H), 1.0 (m, 2H), 1.25 (m, 3H), 1.6 (m, 3H), 1.8 (m, 2H), 2.6-2.7 (m, 4H), 5.86 (d, $J_{H-P}$=14.8 Hz, 1H, PCHN), 5.96 (s, PCHN), 6.26 (m, 1H, furan), 6.33 (d, $J_{H-P}$=1.5 Hz, 1H, furan), 6.36 (dd, $J_{H-P}$=1.9, 3.3 Hz, 1H, furan), 7.35 (m, 2H, furan); $^{13}$C{$^1$H} NMR (CDCl$_3$): δ 25.80 (d, $J_{C-P}$=1.3 Hz), 26.51 (s), 26.47 (d, $J_{C-P}$=20.3 Hz), 28.49 (d, $J_{C-P}$=7 Hz), 29.47 (s), 29.76 (d, $J_{C-P}$=22.9 Hz), 30.33 (s), 32.47 (d, $J_{C-P}$=21. Hz), 50.25 (d, $J_{C-P}$=24.2 Hz), 54.65 (d, $J_{C-P}$=31.2 Hz), 107.16 (d, $J_{C-P}$=2.5 Hz), 107.76 (d, $J_{C-P}$=7 Hz), 110.62 (s), 110.94 (s), 141.73 (d, $J_{C-P}$=1.3 Hz), 142.97 (s), 147.45 (d, $J_{C-P}$=2.5 Hz), 150.21 (d, $J_{C-P}$=17.2 Hz), 165.55 (s, CO), 167.59 (s, CO); $^{31}$P NMR (CDCl$_3$): δ 12.9 (m). Analysis calculated for C$_{20}$H$_{23}$N$_2$O$_4$P: C, 62.17; H, 6.0; N, 7.25. Found: C, 62.04; H, 5.52; N, 7.16.

rac-6a: Yield=65% of a white solid with a rac isomer. X-ray quality crystals from grown from CH$_2$Cl$_2$/hexanes at room temperature. $^1$H NMR (CDCl$_3$): δ 6.25 (d, 1H, J(H,P)=19.5 Hz, PCHN), 6.95 (s, 1H, PCHN), 7.05 (m, 3H, Ph), 7.13-7.19 (m, 5H, Ph), 7.3-7.4 (m, 7H, Ph), 7.3-7.8 (m, 2H, CH), 8.44 (m, 1H, CH), 8.48 (m, 1H, CH), $^{13}$C{$^1$H} NMR (CDCl$_3$): δ 60.3 (d, $J_{C-P}$=19.7 Hz, PCHN), 64.9 (d, $J_{C-P}$=31.8 Hz, PCHN), 125.10 (d, $J_{C-P}$=3.2 Hz), 125.42 (d, $J_{C-P}$=6.3 Hz), 126.88 (d, $J_{C-P}$=1.9 Hz), 127.83 (s), 127.94 (s), 128.06(d, $J_{C-P}$=2.6 Hz), 128.55 (d, $J_{C-P}$=7.0 Hz), 129.33 (d, $J_{C-P}$=1.3 Hz), 129.43 (s), 130.03 (s), 130.22 (s), 130.35 (s), 130.46 (s), 132.85 (d, $J_{C-P}$=1.2 Hz), 132.93 9s), 133.188(s), 133.55 (d, $J_{C-P}$=8.3 Hz), 137.2 (d, $J_{C-P}$=14.6 Hz), 156.30 (s, CO), 156.50(s, CO); $^{31}$P NMR (CDCl$_3$): δ −1.3 (m). Analysis calculated for C$_{28}$H$_{21}$N$_2$O$_2$P: C, 74.99; H, 4.72; N, 6.25. Found: C, 75.21; H, 4.64; N, 6.32.

rac-6b: Yield=71% of a white solid with mainly a rac isomer. X-ray quality crystals were grown from CH$_2$Cl$_2$/hexanes at room temperature. $^1$H NMR (CDCl$_3$): δ 5.81 (m, 1H, furan), 6.09 (dd, J=3, 2 Hz, 1H, furan), 6.32 (m, 1H, furan), 6.44 (m, 1H, furan), 6.47(d, $J_{H-P}$=28 Hz, 1H, PCHN), 6.73 (d, $J_{H-P}$=2 Hz, 1H, PCHN), 6.92 (m, 1H, furan), 7.3 (m, 5H, Ph), 7.35 (m, 1H, furan), 7.77 (m, 2H, CH), 8.22 (m, 1H, CH), 8.36 (m, 1H, CH); $^{13}$C{$^1$H} NMR (CDCl$_3$): δ 54.7 (d, $J_{C-P}$=18 Hz, PCHN), 60.2 (d, $J_{C-P}$=30 Hz, PCHN), 107.2 (d, $J_{C-P}$=4 Hz, furan), 108.1 (d, $J_{C-P}$=6 Hz, furan), 110.5 (s, furan), 110.8 (s, furan), 127.7 (s, CH), 127.8 (s, CH), 128.6 (d, $J_{C-P}$=8 Hz, Ph), 129.3 (s, CC=O), 130.2 (d, $J_{C-P}$=22 Hz, C$_{ipso}$), 130.5 (s, CC=O), 130.8 (s, Ph), 133.1 (s, CH), 133.3 (d, $J_{C-P}$=10 Hz, Ph), 133.5 (s, CH), 141.6 (s, furan), 143.3 (s, furan), 145.8 (s, furan), 149.2 (d, $J_{C-P}$=13 Hz, furan), 156.3 (s, 2C, C=O); $^{31}$P NMR (CDCl$_3$): δ −14.7 (b). Analysis calculated for C$_{24}$H$_{17}$N$_2$O$_4$P: C, 67.29; H, 4.0; N, 6.54. Found: C, 66.99; H, 3.76; N, 6.39.

rac-6c: Yield=28% of a white solid (rac/meso=11). $^1$H NMR (CDCl$_3$): δ 2.46 (s, 3H, CH$_3$), 2.47 (s, 3H, CH$_3$), 5.98 (d, J=9.3 Hz, 1H), 6.35 (d, $J_{H-P}$=18 Hz, 1H, PCHN), 6.48 (t, J=7 Hz, 1H), 6.79 (d, J=7.5 Hz, 1H), 6.90 (s, 1H, PCHN), 6.85-7.3 (m, 10H), 7.84 (m, 2H, CH), 8.29 (m, 1H, CH), 8.39 (m, 1H, CH), How many H's; $^{13}$C{$^1$H} NMR (CDCl$_3$): δ 20.4 (d, $J_{C-P}$=4 Hz, CH$_3$), 20.6 (d, $J_{C-P}$=7 Hz, CH$_3$), 59.0 (d, $J_{C-P}$=20 Hz, PCHN), 62.8 (d, $J_{C-P}$=32 Hz, PCHN), Peaks at 120-140 ppm have not been assigned due to the complexity; $^{31}$P NMR (CDCl$_3$): δ −13.9 (d, $J_{P-H}$=17 Hz). Analysis calculated for C$_{30}$H$_{25}$N$_2$O$_2$P(CH$_2$Cl$_2$)$_{0.5}$: C, 70.59; H, 5.05; N, 5.40. Found: C, 70.93; H, 4.93; N, 5.42.

rac-6d: Yield (isolated)=24% of a white solid (rac/meso=11). $^1$H NMR (CDCl$_3$): δ 6.41 (d, $J_{H-P}$=19 Hz, 1H, PCHN), 7.07 (s, 1H, PCHN), 8.30 (m, 1H, CH), 8.46 (m, 1H, CH), 7.0-8.0 (m, 22H); $^{13}$C{$^1$H} NMR (CDCl$_3$): δ 61.2 (d, $J_{C-P}$=21 Hz, PCHN), 65.9 (d, $J_{C-P}$=31 Hz, PCHN), Peaks at 120-140 ppm have not been assigned due to the complexity; $^{31}$P NMR (CDCl$_3$): δ −2.6 (d, $J_{P-H}$=19 Hz). Analysis calculated for C$_{36}$H$_{25}$N$_2$O$_2$P: C, 78.82; H, 4.59; N, 5.11. Found: C, 78.21; H, 4.59; N, 5.19.

rac-6e: Yield=90% of a yellow solid (rac/meso=2). Recrystallization from hexane gave the pure rac isomer (38%) and X-ray quality crystals of rac-6e were obtained from slow evaporation of a hexane solution. $^1$H NMR (CDCl$_3$): δ 6.65 (d, $J_{H-P}$=19.1 Hz, 1H, PCHN), 6.91 (d, $J_{H-P}$=4.1 Hz, 1H, PCHN), 7.3=7.4 (m, 5H, Ph), 7.8 (m, 2H), 8.28 (m, 1H), 8.34 (m, 1H); $^{13}$C{$^1$H} NMR (CDCl$_3$): δ 51.89 (d, $J_{C-P}$=22.3 Hz, PCHN), 57.01 (d, $J_{C-P}$=33.7 Hz, PCHN), 156.42 (s, CO), 156.58 (s, CO), peaks at 110-145 ppm have not been assigned due to the complexity. $^{31}$P NMR (CDCl$_3$): δ −2.7 (m). Analysis calculated for C$_{28}$H$_{11}$N$_2$F$_{10}$O$_2$P: C, 53.52; H, 1.76; N, 4.46. Found: C, 53.72; H, 2.01; N, 4.23.

rac-6f: Yield=80% of a yellow oil (rac/meso=4). $^1$H NMR (CDCl$_3$): δ 0.75 (t, $J_{H-H}$=7 Hz, 3H CH$_3$), 0.92 (t, $J_{H-H}$=7 Hz, 3H, CH$_3$), 1.5 (m, 4H, CH$_2$), 1.7 (m, 2H, CH$_2$), 1.9 (m, 2H, CH$_2$), 4.86 (ddd, $J_{H-P}$=21 Hz, $J_{H-H}$=12, 4 Hz, 1H, PCHN), 5.30 (dd, $J_{H-H}$=9, 5 Hz, 1H, PCHN), 7.25-7.6 (m, 5H, aromatics), 7.6-8.1 (m, 2H, aromatics), 8.31 (m, 2H, aromatics); $^{13}$C NMR (CDCl$_3$): δ 14.4 (s, CH$_3$), 20.8 (d, $J_{C-P}$=10 Hz, CH$_2$), 21.4 (d, J$_{C-P}$=8 Hz, CH$_2$), 35.6 (s, CH$_2$), 35.8 (s, CH$_2$), 59.9 (d, J$_{C-P}$=17 Hz, PCHN), 62.9 (d, J$_{C-P}$=27 Hz, PCHN), 128.0 (s), 128.3 (s), 129.6 (d, J$_{C-P}$=8 Hz), 131.6 (s), 134.0 (d, J$_{C-P}$=12 Hz), 134.9 (s), 135.1 (s), A range of 120-140 ppm has not been assigned due to the complexity; $^{31}$P NMR (CDCl$_3$): δ −18.9 (b). Analysis calculated for C$_{22}$H$_{25}$N$_2$O$_2$P: C, 69.46; H, 6.62; N, 7.36. Found: C, 66.13; H, 4.96; N, 3.66.

rac-6g: Yield=49.9% of a white solid, prepared from the treatment of 1d and phthaloyl chloride in THF. $^1$H NMR (CDCl$_3$): δ 0.41, (d, J$_{H-H}$=7.1 Hz, 3H, CH$_3$), 0.95-1.06 (m, 9H, CH$_3$) 2.41, (oct, J$_{H-H}$=6.8 Hz, 1H, CHMe$_2$), 3.13, (oct, J$_{H-H}$=6.9 Hz, 1H, CHMe$_2$), 4.94 (dd, J$_{H-H}$=5.8 Hz, J$_{P-H}$=20.4 Hz, 1H, PCHN), 5.32 (dd, J$_{H-H}$=6.2 Hz, J$_{P-H}$=1.7 Hz, 1H, PCHN), 7.30-7.45, (m, 3H), 7.60-7.68, (m, 2H), 7.79-7.89, (m, 2H), 8.30-8.44, (m, 2H); $^{13}$C{$^1$H} NMR (CDCl$_3$): δ 18.0 (d, J$_{P-C}$=1.0 Hz, CH$_3$), 18.7 (d, J$_{P-C}$=10.0 Hz, CH$_3$), 19.8, (d, J$_{P-C}$=8.86 Hz, CH$_3$), 20.2 (d, J$_{P-C}$=10.0 Hz, CH$_3$), 22.5 (d, J$_{P-C}$=4.8 Hz, CH$_3$), 23.5 (d, J$_{P-C}$=21.4 Hz, CH$_3$), 65.7 (d, J$_{P-C}$=17.6 Hz, PCHN), 67.8 d, J$_{P-C}$=32.0 Hz, PCHN), 157.6 (s, CO), 156.7 (s, CO); peaks at 127.4-135.1 ppm have not been assigned due to the complexity. $^{31}$P NMR (CDCl$_3$): δ −25.7. Analysis calculated for C$_{22}$H$_{25}$N$_2$O$_2$P: C, 69.46; H, 6.62; N, 7.36. Found: C, 69.45; H, 6.31; N, 7.42.

General Synthesis of Compounds 7 and 9

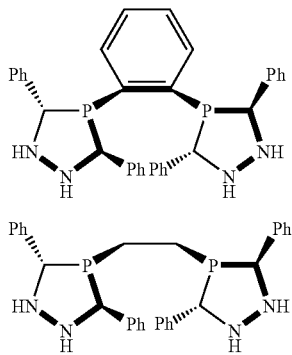

7

9

Phenyl azine (322.4 mg, 1.55 mmol) in Et$_2$O (50 mL) was treated with HCl (0.78 mL, 2M Et2O solution) at 0° C. The corresponding bis-phosphine (1,2-diphosphinobenzene (7); 1,2-diphosphinoethane (9)) (0.775 mmol) was then slowly added at 0° C., and the mixture was stirred at room temperature overnight. To the resultant white slurry was added a 10% aqueous K$_2$CO$_3$ solution (ca. 20 mL) at ice-bath temperature. The aqueous and organic layers were filtered off via cannula to obtain a white solid which was subsequently washed with distilled water and Et$_2$O. The white solid was dried overnight under vacuum to obtain analytically pure compound 7. X-ray quality crystals for rac-7 were grown from CH$_2$Cl$_2$ and hexanes at room temperature.

rac-7: Yield=32% of a white solid. $^1$H NMR (CDCl$_3$): δ 3.75 (dd, J$_{H-H}$=6.6, 10.3 Hz, 2H, NH), 4.34 (t, J$_{H-H}$=11.4 Hz, 2H, NH), 4.55 (d, J$_{H-H}$=6.3 Hz, 2H, PCHN), 4.71 (q, J=11.7, 2H, PCHN), 6.63 (m, 4H), 6.80 (m, 4H), 6.94 (m, 2H), 7.23-7.40 (m, 14H); $^{13}$C{$^1$H} NMR (CDCl$_3$): δ 70.40 (t, J$_{C-P}$=6.4 Hz, PCHN), 71.27 (t, J$_{C-P}$=14.0 Hz, PCHN), 126.40 (t, J$_{C-P}$=2.5 Hz), 126.58 (s), 127.47 (s), 128.75 (s), 129.24 (s), 131.72 (s), 134.98 (s), 141.08 (t, J$_{C-P}$=8.3 Hz), 141.5 (s). Peaks at 127-128 ppm haven't been assigned due to the complexity. $^{31}$P NMR (CDCl$_3$): δ 11.6 (t, J$_{P-H}$=10.7 Hz). Analysis calculated for C$_{34}$H$_{32}$N$_4$P$_2$: C, 73.11; H, 5.77; N, 10.03. Found: C, 73.05; H, 5.74; N, 10.1.

rac-9: Yield=32% of a white solid. $^1$H NMR (CDCl$_3$): δ 0.95 (m, 4H, CH$_2$), 3.76 (dd, J$_{H-H}$=7.0, 11.0 Hz, 2H, NH), 4.11 (t, J=10.3 Hz, 2H, NH), 4.41 (d, J$_{H-H}$=7.0 Hz, 2H, PCHN), 4.82 (q, J=10.3 Hz, 2H, PCHN), 7.28-7.40 (m, 6H, Ph), 7.50 (m, 4H, Ph); $^{13}$C{$^1$H} NMR (CDCl$_3$): δ 19.8 (d, J$_{C-P}$=7 Hz, CH$_2$P), 69.7 (dd, J$_{C-P}$=10.8, 14 Hz, PCHN), 73.3 (t, J$_{C-P}$=11.4 Hz, PCHN), 126.1 (s), 126.7 (s), 127.44 (s), 127.6 (d, J$_{C-P}$=11 Hz), 128.57 (s), 128.83 (s), 136.4 (s, C$_{ipso}$), 139.9 (t, J$_{C-P}$=8.3 Hz, C$_{ipso}$); $^{31}$P NMR (CDCl$_3$): δ 15.8 (m). Analysis calculated for C$_{30}$H$_{32}$N$_4$P$_2$: C, 70.58; H, 6.32; N, 10.97. Found: C, 70.29; H, 6.31; N, 11.0.

Synthesis of rac-8 Compound

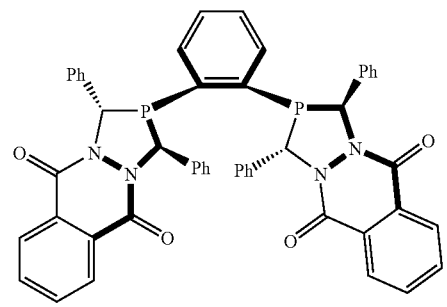

8

1,2-Bis(phosphino)benzene (0.2 mL, 1.55 mmol) was added to the ether solution of phenyl azine (648 mg, 3.1 mmol) and phthalolyl chloride (0.9 mL, 6.25 mmol) at 0° C. After the mixture stirred over night, an aqueous 10% K$_2$CO$_3$ solution (30 mL) was added into the resultant white slurry at ice-bath temperature. The aqueous and ether layers were removed via cannula and the residue dried in vacuo. The residue was washed with THF and Et$_2$O (1:1 (v/v)) to obtain a white solid of rac-8 in a 23% yield. X-ray quality crystals were grown from CH$_2$Cl$_2$/hexanes at room temperature. In addition, rac-8 was made from the addition of rac-7 into phthaloyl chloride in THF at 0° C. $^1$H NMR (CDCl$_3$): δ 6.15 (t, J$_{P-H}$=10.3 Hz, 2H, PCHN), 6.18 (s, 2H, PCHN), 6.96 (m, 4H), 7.1 (m, 4H), 7.17 (m, 2H), 7.3-7.4 (m, 14H), 7.8 (m, 4H), 8.2 (m, 2H, CH), 8.36 (m, 2H, CH); $^{13}$C{$^1$H} NMR (CDCl$_3$): δ 60.56 (s, PCHN), 65.75 (t, J$_{C-P}$=18.5 Hz, PCHN), 156.86 (s, CO), 157.11 (s, CO), Peaks at 125-140 ppm haven't been assigned due to the complexity; $^{31}$P NMR (CDCl$_3$): δ −14.4 (t, J$_{P-H}$=10.7 Hz). Analysis calculated for C$_{50}$H$_{36}$N$_4$O$_4$P$_2$ (CH$_2$Cl$_2$)$_{0.8}$: C, 68.81; H, 4.27; N, 6.32. Found: C, 68.55; H, 4.37; N, 6.14.

Resolution Procedure for Tartaric Acid Derivatives: Tart-1a, Tart-1e, and Tart-9

Di-O-methyl-tartaric acid was prepared according to the literature method. I. Felner, K. Schenker, *Helv. Chim. Acta.* 1970, 53, 4, 754-762. The acid was converted to the acid chloride based loosely on literature procedure. T. Purdie, C. R. Young, *J. Chem. Soc.* 1910, 1532. The acid was slowly added to a slight excess of PCl$_5$ in benzene at 0° C. under nitrogen followed by stirring overnight. The resulting solution was filtered and solvent was removed in vacuo to yield a yellow solid. The solid was purified by sublimation. $^1$H NMR (CDCl$_3$): 3.57 (s, 6H), 4.73 (s, 2H); $^{13}$C {$^1$H} NMR (CDCl$_3$): δ 60.5, 87.4, 169.3.

A THF solution of the acid chloride was added dropwise to a stirring THF solution of the diazaphospholane at room temperature. After stirring overnight, the THF was removed in vacuo. Ether was added to the resulting oil, and to the resulting solution was added aqueous 10% K$_2$CO$_3$. The ether layer was dried over MgSO$_4$, and the ether was removed in vacuo. Resolution of the Tart-9 diastereomers was accomplished on Aldrich silica preparative TLC plates (20 cm×20 cm×1 mm) with a mobile phase of ethyl acetate/hexane. Both diastereomers were separately recovered. Resolution of Tart-1a and Tart-1e was accomplished by flash chromatography using a column packed with Silica Gel 60 (EM Science) and eluents of 15:1 and 30:1 CH$_2$Cl$_2$/ethyl acetate. One diastereomer of each was cleanly recovered. The other diastereomers each had unidentified impurities in $^1$H and $^{31}$P NMR's. Absolute configurations of the resolved diastereomers are not currently known.

Tart-9: [Crude product has only 2 peaks in $^{31}$P NMR] (R$_f$=0.17): $^1$H NMR (CDCl$_3$): 0.95 (m, 4H, CH$_2$), 3.61 (s, 6H, OCH$_3$), 3.75 (s, 6H, OCH$_3$), 3.89 (d, J$_{H-H}$=12 Hz, 2H, CHOCH$_3$), 4.27 (d, J$_{H-H}$=12 Hz, 2H, CHOCH$_3$), 5.56 (s, 2H, PCHN), 5.56 (d, J$_{H-P}$=16 Hz, 2H, PCHN), 6.9-7.4 (m, 30H); $^{31}$P NMR (CDCl$_3$): δ 4.7 (m); (R$_f$=0.28): $^1$H NMR (CDCl$_3$): 3.41 (s, 6H, OCH$_3$), 3.61 (s, 6H, OCH$_3$), 3.88 (d, J$_{H-H}$=3 Hz, 2H, CHOCH$_3$), 3.97 (d, J$_{H-H}$=3 Hz, 2H, CHOCH$_3$), 5.42 (d, J$_{H-P}$=17 Hz, 2H, PCHN), 5.57 (s, 2H, PCHN), 6.9-7.4 (m, 30H); $^{31}$P NMR (CDCl$_3$): δ 3.5 (m).

Tart-1a: [Crude product has two diastereomers as main products with several unidentified impurities] (R$_f$=0.33): $^1$H NMR (CDCl$_3$): 3.58 (s, 3H, OCH$_3$), 3.71 (s, 3H, OCH$_3$), 3.97 (d, J$_{H-H}$=12 Hz, 1H, CHOCH$_3$), 4.17 (d, J$_{H-H}$=12 Hz, 1H, CHOCH$_3$), 5.80 (d, J$_{H-P}$=19 Hz, 1H, PCHN), 6.38 (s, 1H, PCHN), 6.6-7.4 (m, 15H); $^{31}$P NMR (CDCl$_3$): δ 9.2 (m) with a trace of other impurities; (R$_f$=0.55): $^1$H NMR (CDCl$_3$): 3.47 (s, 3H, OCH$_3$), 3.57 (s, 3H, OCH$_3$), 3.86 (d, J$_{H-H}$=4 Hz, 1H, CHOCH$_3$), 4.00 (d, J$_{H-H}$=4 Hz, 1H, CHOCH$_3$), 5.71 (d, J$_{H-P}$=19 Hz, 1H, PCHN), 6.42 (s, 1H, PCHN), 6.6-7.5 (m, 15H); $^{31}$P NMR (CDCl$_3$): δ 8.5 (m).

Tart-1e: [Crude product has two diastereomers as main products with several unidentified impurities] (R$_f$=0.31): $^1$H NMR (CDCl$_3$): 0.84 (d, J$_{H-P}$=1 Hz, 9H, C(CH$_3$)$_3$), 0.98 (s, 9H, C(CH$_3$)$_3$), 3.51 (s, 3H, OCH$_3$), 3.53 (s, 3H, OCH$_3$), 3.86 (d, J$_{H-H}$=3 Hz, 1H, CHOCH$_3$), 3.94 (d, J$_{H-H}$=3 Hz, 1H, CHOCH$_3$), 4.58 (d, J$_{H-P}$=21 Hz, 1H, PCHN), 4.74 (d, J$_{H-P}$=3 Hz, 1H, PCHN), 7.2-7.7 (m, 5H); $^{31}$P NMR (CDCl$_3$): δ 1.4; (R$_f$=0.15): $^1$H NMR (CDCl$_3$): 0.78 (d, J$_{H-P}$=1 Hz, 9H, C(CH$_3$)$_3$), 0.96 (s, 9H, C(CH$_3$)$_3$), 3.68 (s, 3H, OCH$_3$), 3.72 (s, 3H, OCH$_3$), 3.99 (d, J$_{H-H}$=11 Hz, 1H, CHOCH$_3$), 4.25 (d, J$_{H-H}$=11 Hz, 1H, CHOCH$_3$), 4.53 (d, J$_{H-P}$=21 Hz, 1H, PCHN), 4.81 (d, J$_{H-P}$=3 Hz, PCHN), 7.2-7.7 (m, 5H); $^{31}$P NMR (CDCl$_3$): δ 4.8 plus one impurity with peak height ratio about 5:1 product to impurity at δ −6.2.

Reaction of an Acid Dichloride with a Diimine

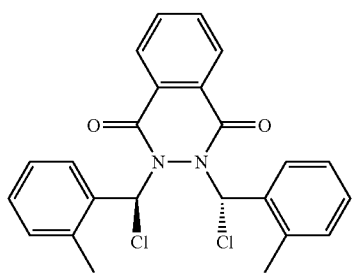

All manipulations were performed under a N$_2$ atmosphere and using standard Schlenk techniques.

Two equivalents of phthaloyl dichloride were added dropwise to a stirred ether solution of the azine (970 mg) formed by the reaction of equivalents of 2-methyl benzaldehyde with hydrazine. A small quantity of HCl (1.6 mmol as a 2M solution in diethyl ether) was added to the solution. After 5 days, 100 mg of crystals had formed which were characterized using X-ray crystallographic analysis.

Synthesis of Diazaphospholane from Dichloro Compound

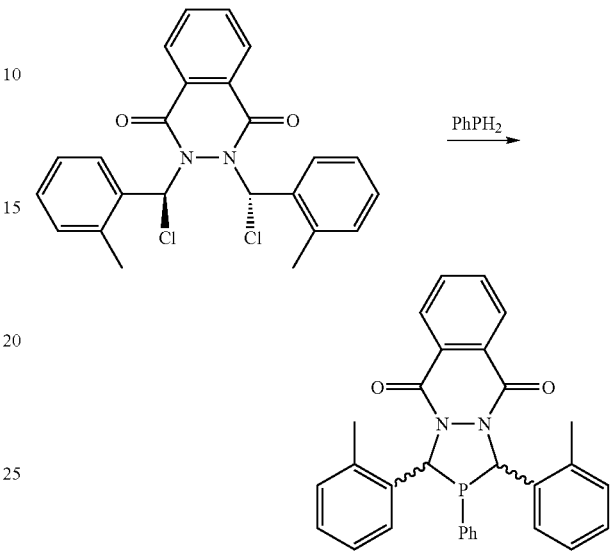

All manipulations were performed under N$_2$ using standard Schlenk techniques.

A solution of the azine (383 mg in 100 mL Et$_2$O) prepared from 2-methyl benzaldehyde and hydrazine was treated with 2 equivalents of phthaloyl dichloride and stirred overnight. Phenylphosphine (170 mg) was slowly added, and the solution was stirred overnight. To the resultant solution was added a 10% aqueous solution of K$_2$CO$_3$. The ether layer was separated, dried over MgSO$_4$, and filtered using a glass frit. The ether was removed, and 400 mg of the diazaphospholane was obtained as a 10:1 rac:meso mixture.

Synthesis of Diimine from trans-1,2-Diaminocyclohexane and 2-Naphthaldehyde

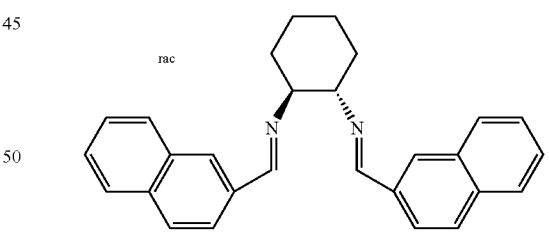

Trans-1,2-diaminocyclohexane (2.0 mL) was added dropwise to a stirred solution of two equivalents of 2-naphthaldehyde (8.2 g in 100 mL benzene). After stirring for one hour, the solution was heated to 50° C. for 30 minutes. The solvent was removed on a rotary evaporator. The resulting solid was redissolved in benzene and was then removed by rotary evaporation to azeotropically remove water. This procedure was repeated once more. The remaining solid was rinsed eight times with 25 mL of ether and filtered. The remaining solid was dried under vacuum for 15 minutes and was used without further purification (yield=5.17 g).

Synthesis of Diazaphosphacycle from Diimine Formed from trans-1,2-Diaminocyclohexane and 2-Naphthaldehyde

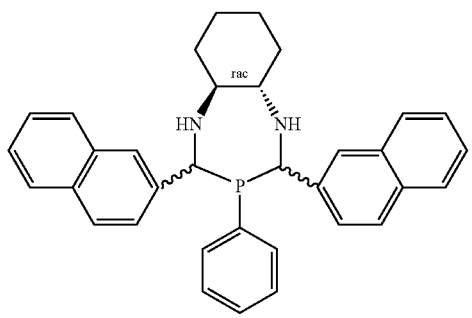

All manipulations were performed under $N_2$ using standard Schlenk techniques.

Phenyl phosphine (0.3 mL) was added dropwise to a stirred solution of the diimine formed from trans-1,2-diaminocyclohexane and benzaldehyde (1.06 g in 100 mL THF). After 10 minutes, an HCl solution (1.36 mL of a 2M solution in ether) was added dropwise. The resulting solution was then stirred for 18 hours. THF was removed under vacuum and 75 mL of ether was added. A 10% aqueous solution of $K_2CO_3$ was added to the ether mixture and was stirred until all solid had gone into solution. The ether layer was separated, dried over $MgSO_4$, and filtered. The ether was then removed under vacuum to yield a solid product (crude yield=1.31 g) consisting of two diastereomers. $^{31}P$ NMR ($CDCl_3$): δ 19, 9.

Synthesis of an $\eta^3$-allyl Pd Complex with a Bidentate Diazaphospholane

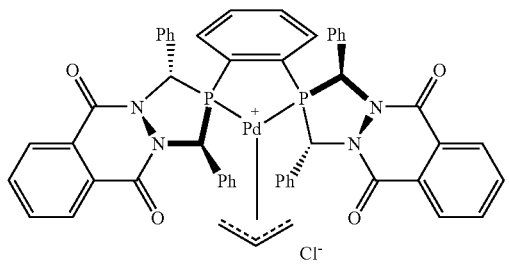

To a Teflon® brand fluorinated polymer capped NMR tube was added [($\eta^3$-$C_3H_5$)PdCl]$_2$ (5.2 μmol) (Aldrich Chemical (Milwaukee, Wis.)) and the diazaphospholane (10.3 μmol) indicated in the above structure. $CD_2Cl_2$ (ca 1 mL) was added, and the NMR tube was agitated until the solids went into solution. The designated Pd complex was obtained and characterized by NMR. $^1H$ NMR ($CD_2Cl_2$): δ 3.4 (allyl $CH_2$), 4.9 (allyl CH), 6.4 (PCHN), 6.6-7.6 (unassigned), 7.9 (phthaloyl), 8.3 (phthaloyl); $^{31}P$ NMR: δ 71 ppm.

Synthesis of a Dimethyl Pt Complex with a Bidentate Diazaphospholane

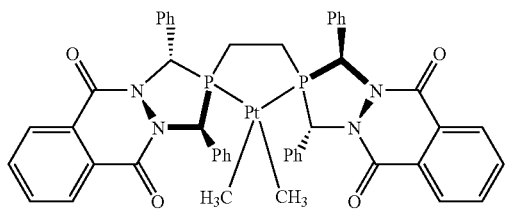

To a Teflon® brand fluorinated polymer capped NMR tube was added, [(cyclooctadiene)Pt(CH$_3$)$_2$] (1.3 μmol) (Aldrich Chemical (Milwaukee, Wis.) and the diazaphospholane (1.2 μmol) indicated by the above structure. Approximately 1 mL of $C_6D_6$ was added and the NMR tube was agitated until the solids went into solution. The solution was evaporated to dryness in vacuo to remove free cyclooctadiene, and approximately 1 mL of $C_6D_6$ was added. The dimethyl Pt complex indicated above was characterized by NMR. $^1H$ NMR ($C_6D_6$): δ 0.6 ($CH_3$), 0.2-1.6 (broad ethyl peaks unassigned), 5.8 (PCHN), 6.6 (PCHN), 6.7-7.4 (aromatics), 8.4 (phthaloyl); $^{31}P$ NMR: δ 63 (with $^{195}Pt$ satellites; $J_{Pt-P}$=1680 Hz).

Synthesis of Rhodium(diazaphospholane)Cl(norbornadiene)

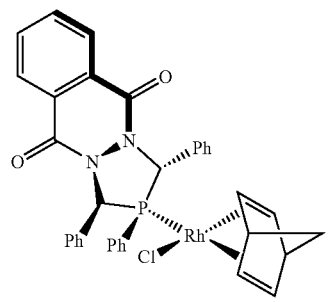

A $CH_2Cl_2$ solution of 2,5-diphenyldiazaphospholane (100 mg, 0.224 mmol) was added into a $CH_2Cl_2$ solution of [Rh(norbornadiene)Cl]$_2$ (51.7 mg, 0.112 mmol) at room temperature. The resulting mixture was stirred for 1 hour and pumped on under vacuum to quantitatively yield a red-orange solid. X-ray quality crystals were obtained from $CH_2Cl_2$ and hexane at room temperature. The Rh complex indicated above was characterized by X-ray crystallography and NMR spectroscopy. $^1H$ NMR ($CDCl_3$): δ1.33 (s, 2H), 3.04 (m 1H), 3.34 (m, 1H), 3.50 (m, 1H), 3.60 (m, 1H), 5.09 (m, 1H), 5.22 (m, 1H), 6.9-7.0 (m, 5H), 7.1-7.43 (m, 9H), 7.50 (m, 3H), 7.79 (m, 5H), 8.24 (m, 1H), 8.32 (m, 1H); $^{31}P\{^1H\}$ NMR ($CDCl_3$): δ 45.0 (d, $J_{Rh-P}$=189 Hz).

Synthesis of [{1,2-bis(diazaphospholanes)benzene}RhCl]$_2$

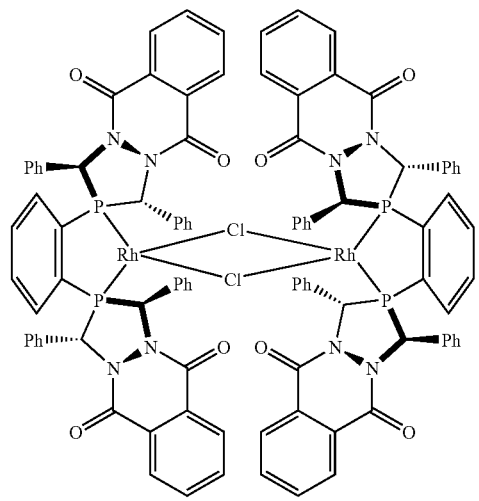

A CH$_2$Cl$_2$ solution of 1,2-bis(diazaphospholanes)benzene as indicated in the above structure was added into a [Rh(norbornadiene)Cl]$_2$ (prepared according to known procedure see E. W. Abel, M. A. Bennet, G. Wilkinson, J. Chem. Soc. 1959, 3178-3182 and available from Aldrich Chemical (Milwaukee, Wis.)) (or [Rh(COD)Cl]$_2$) (prepared according to known procedure see G. Giordano, R. H. Crabtree, Inorg. Synth. 1990, 28 88-90 and available from Strem Chemicals, Inc. (Newburyport, Mass.)) solution in CH$_2$Cl$_2$ at room temperature. The reaction mixture was stirred for 1 hour and pumped on under vacuum to quantitatively yield a red-orange solid. X-ray quality crystals were obtained from CH$_2$Cl$_2$ and hexane at room temperature. The dirhodium complex indicated above was characterized by X-ray crystallography and NMR spectroscopy. $^1$H NMR (CDCl$_3$): δ 5.71 (br, 2H), 6.16 (s, 2H), 7.1-7.3 (m, 14H), 7.47 (m, 6H), 7.88 (m, 4H), 8.32 (m, 2H), 8.40 (m, 2H); $^{31}$P{$^1$H} NMR (CDCl$_3$): δ 87.7 (d, $J_{Rh-P}$=209 Hz).

Synthesis of {Rhodium[1,2-bis(diazaphospholanes)benzene](COD)}BF$_4$

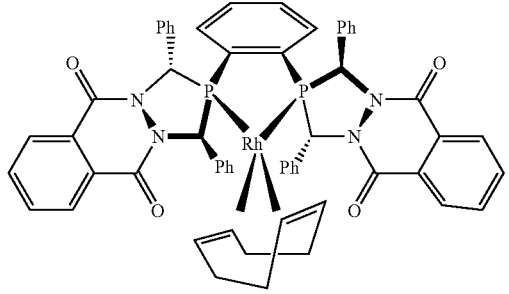

A 1:1 mixture of [Rh(COD)$_2$]BF$_4$ (prepared according to known procedure see T. G. Schenck, J. M. Downes, C. R. Miline, P. B. Mackenzie, M. Boucher, J. Wheland, B. Bosnich, Inorg. Chem. 1985, 24 2334-2337 and available from Pressure Chemical Co. (Pittsburgh, Pa.)) and 1,2-bis(diazaphospholanes)benzene was prepared in an NMR tube at room temperature. After CDCl$_3$ was added, the mixture was agitated well. $^{31}$P{$^1$H} NMR indicated that the initial product was Rh[bis(diazaphospholanes)benzene](COD)}BF$_4$ showing a resonance signal at 62.2 ppm ($J_{Rh-P}$=163 Hz). After 2 days, a new resonance signal appeared at 87.7 ppm ($J_{Rh-P}$=209 Hz), which was identified as [{1,2-bis(diazaphospholanes)benzene}RhCl]$_2$.

Catalytic Allylic Alkylation

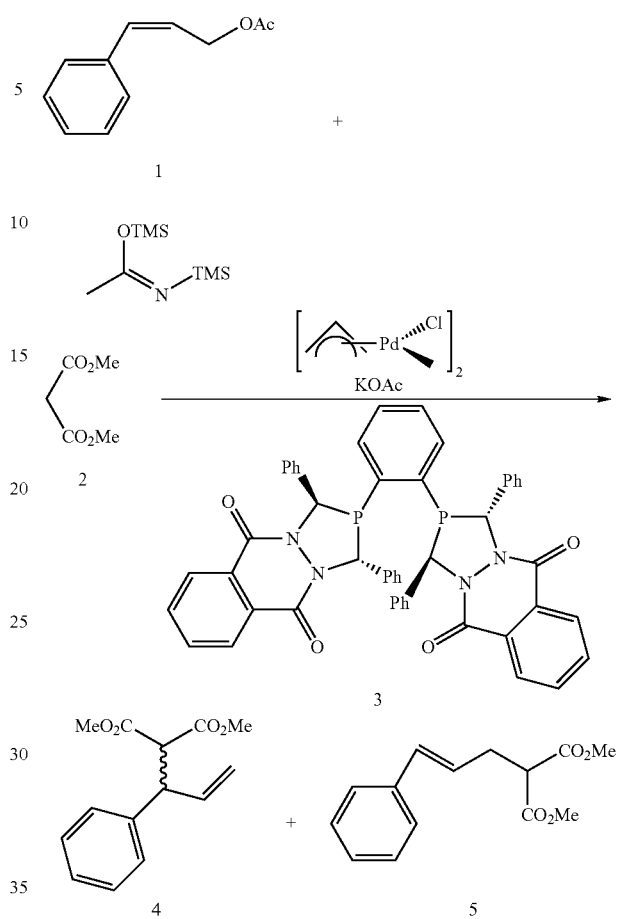

For the purposes of this example, the numbers refer to the numbers of the compounds in the reaction scheme presented above except as otherwise noted.

All manipulations were performed under a N$_2$ atmosphere.

A vial was prepared with 2.8 mg of [Pd($\eta^3$-C$_3$H$_5$)Cl]$_2$ (Aldrich Chemical (Milwaukee, Wis.)) and 15.0 mg of the diazaphospholane (3) (Example 8) in 1 mL CH$_2$Cl$_2$. A second vial was prepared with 1.0 mmol of cinnamyl acetate (1), 3.0 mmol of dimethyl malonate (2), 3.0 mmol of N,O-bis(trimethylsilyl)acetamide 2 (Aldrich Chemical (Milwaukee, Wis.)), and two grains of potassium acetate in 1 mL of CH$_2$Cl$_2$. The second vial was added to the first vial and the solution was stirred for 18 hours at ambient temperature. The solvent was removed under vacuum and the $^1$H NMR of the product dissolved in CDCl$_3$ was taken. As determined by NMR, the conversion of cinnamyl acetate to alkylated products 4 and 5 was >98% with a 33:1 ratio of 5:4.

Hydrogenation of Methylacetamidoacrylate

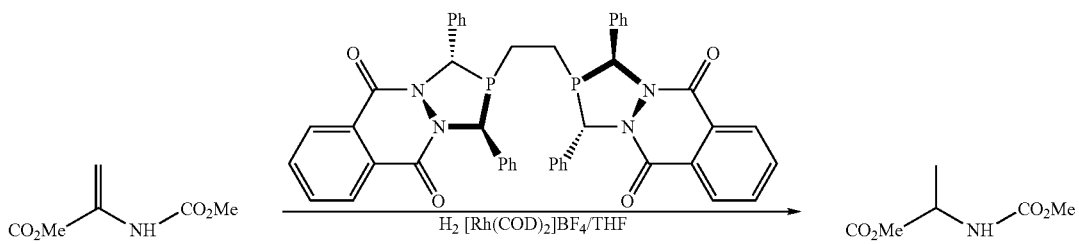

Figure 8:
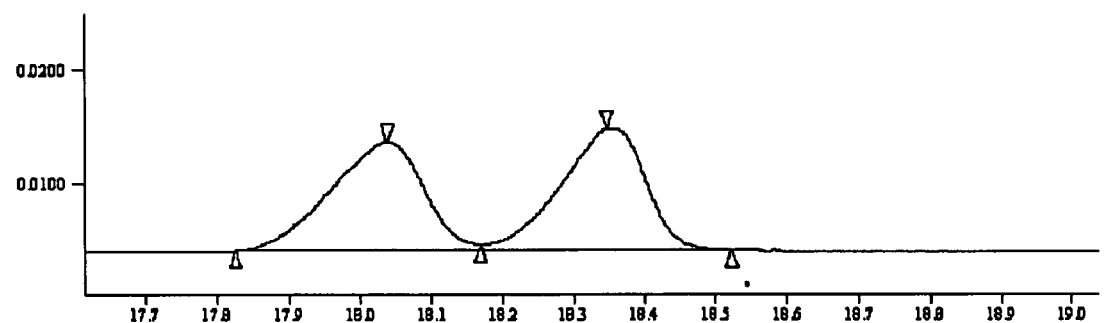
FIG. 8 is a GC spectrum for the hydrogenation product of the hydrogenation of methylacetamidoacrylate using a chiral column with a racemic mixture of the catalyst with a Rh diazaphosphacycle complex.
Figure 9:
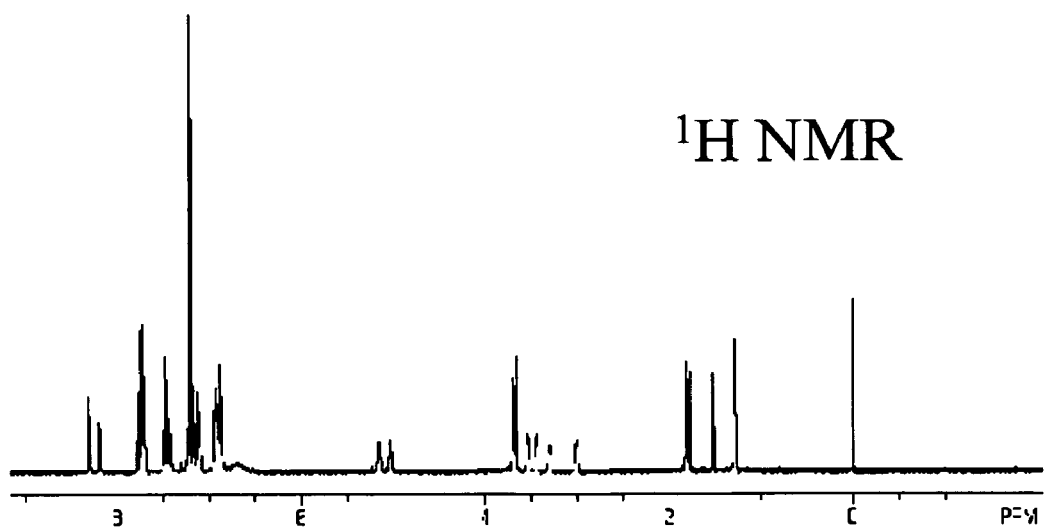
Figure 10:
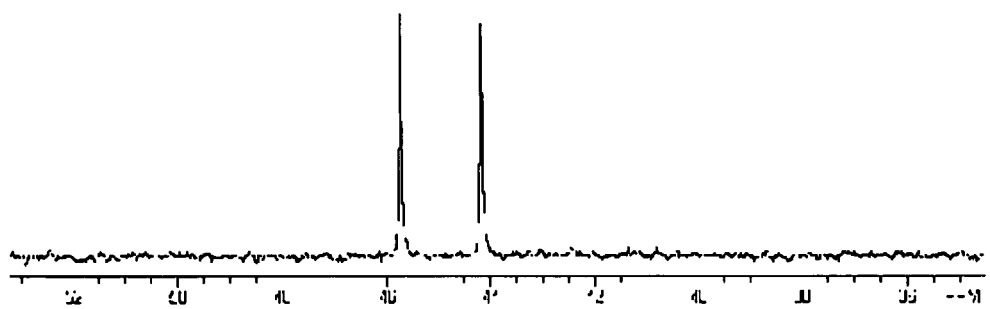
Figure 11:
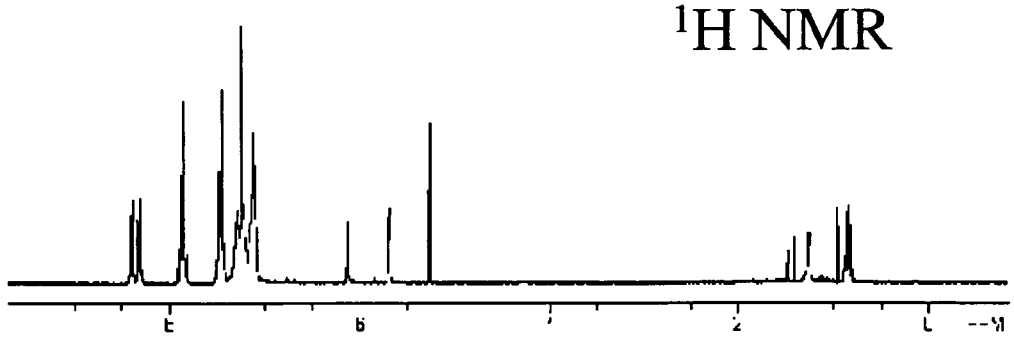
FIG. 11 is a $^{1}$H NMR spectrum of [{1,2-bis(diazaphospholanes)benzene}RhCl]$_{2}$ where the 1,2-bis(diazaphospholane)benzene is compound 8.
Figure 12:
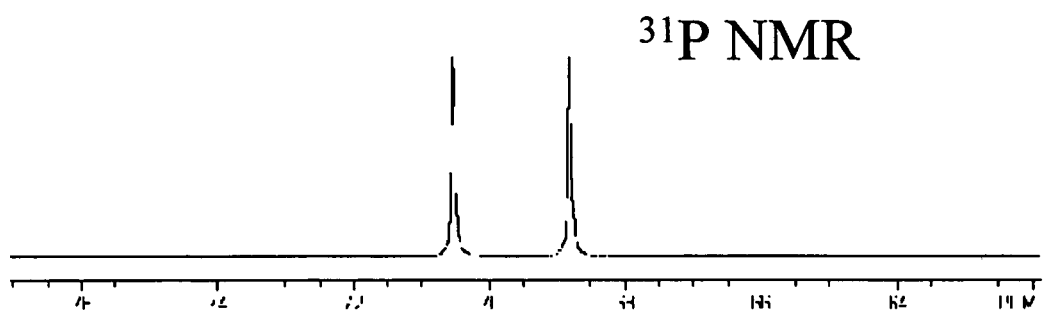
FIG. 12 is a $^{31}$P NMR spectrum ($^{1}$H coupled) of [{1,2-bis(diazaphospholanes)benzene}RhCl]$_{2}$ where the 1,2-bis(diazaphospholane)benzene is compound 8.
Figure 13:
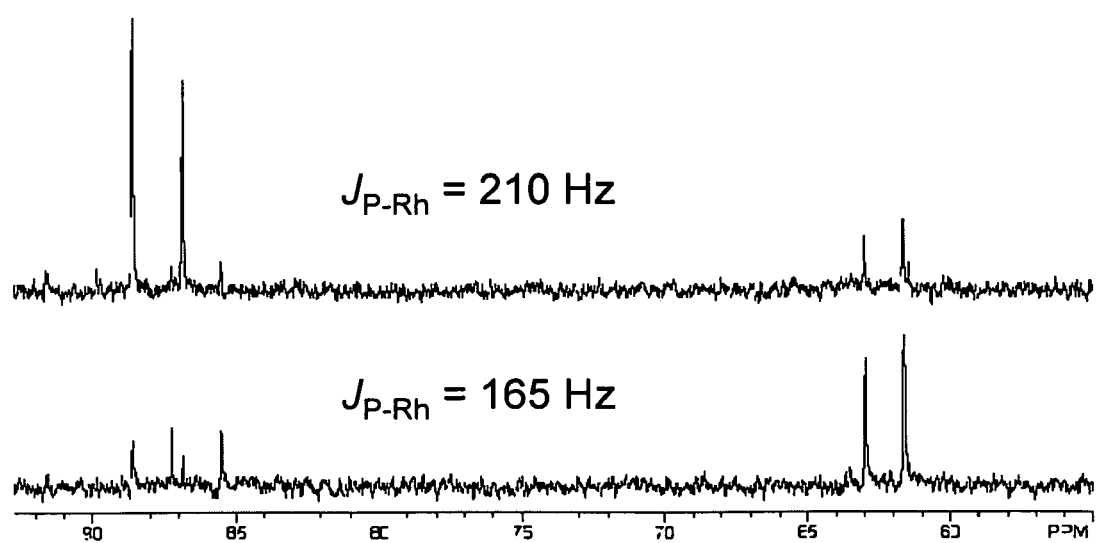
FIG. 13 is a stacked NMR spectrum comparing the $^{31}$P NMR spectrum of [{1,2-bis(diazaphospholanes)benzene}RhCl]$_{2}$ (top) with that of {Rhodium[1,2-bis(diazaphospholanes)benzene](COD)}BF$_{4}$ (bottom) where the 1,2-bis(diazaphospholane)benzene is compound 8.

Under a N₂ atmosphere, a mixture of 1,2-bis(diazaphospholane)ethane (3.85 mg, 0.005 mmol) and [Rh(COD)₂]BF₄ (2 mg, 0.005 mmol) ₂ (Pressure Chemical Co. (Pittsburgh, Pa.)) in THF (3 mL) was stirred for 1 hour at room temperature. Next, methylacetamidoacrylate (14.3 mg, 0.1 mmol) ₂ (Sigma-Aldrich (St. Louis, Mo.)) in THF (3 mL) was added and hydrogen (H₂) bubbled for 30 minutes at room temperature. The reaction flask was then sealed and stirred overnight. The reaction was then filtered through a short path of silica gel (150 mg) and washed with CH₂Cl₂ (5 mL). The hydrogenated product with complete conversion was identified using GC chromatography (FIG. 8) which shows the hydrogenation product of the hydrogenation using a chiral GC column with a racemic mixture of the catalyst.

Additional General Considerations. All syntheses were carried out under a dry nitrogen atmosphere using standard Schlenk techniques. Workup and flash chromatography of the amides 3 were performed open to air. Ether and THF were distilled over Na/benzophenone; CH₂Cl₂ was distilled over P₂O₅. Allyl acetates were synthesized by established procedures (von Matt, P.; Loiseleur, O.; Koch, G.; Pfaltz, A. *Tetrahedron: Asymm.* 1994, 5, 573; Leung, W.; Cosway, S.; Jones, R. H. V.; McCann, H.; Wills, M. *J. Chem. Soc., Perkin Trans.* 1 2001, 2588). Phthaloyl dichloride was placed under vacuum (400 mTorr) for 30 minutes to remove volatile impurities. Phenylphosphine and allylpalladium chloride dimer were purchased from Strem. Silver hexafluorophosphate was from Pennwalt. All other chemicals were purchased from Aldrich.

Synthesis and Resolution of Diazaphosphacycle, 2'

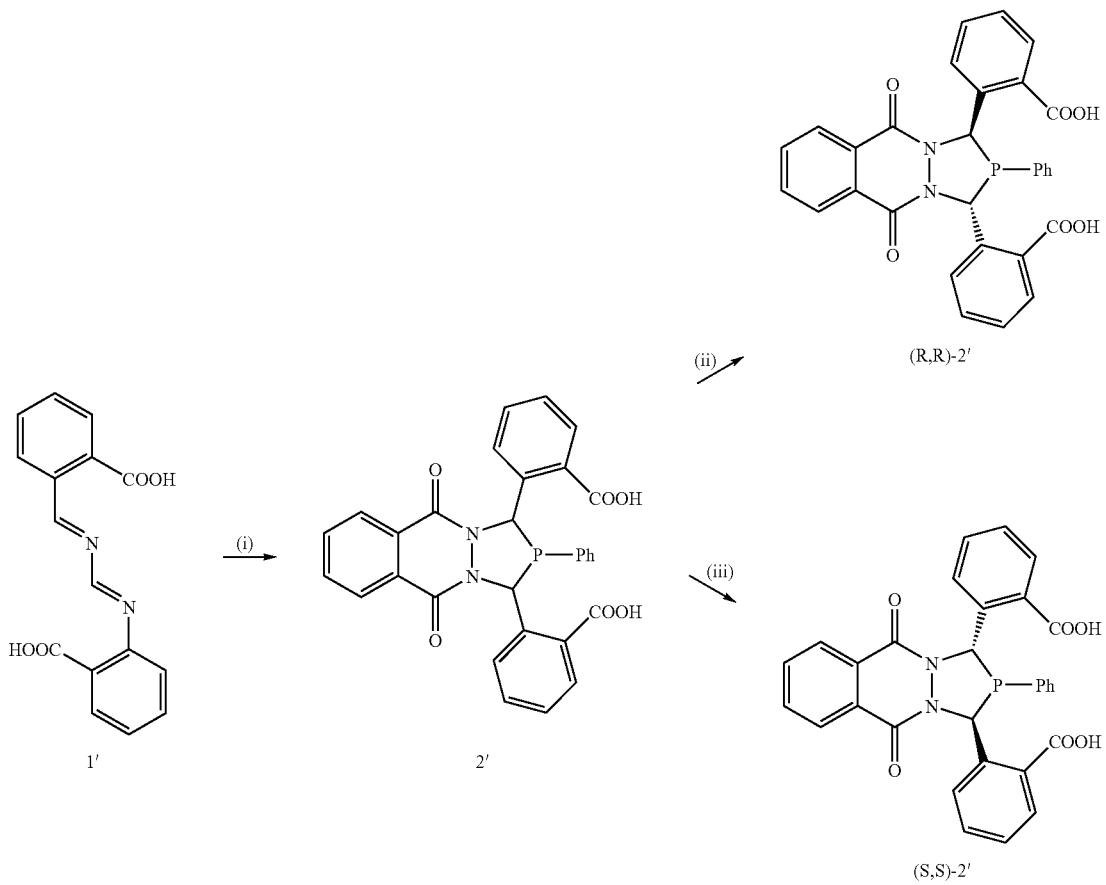

(i) a) Phthaloyl dichloride, phenyl phosphine, THF. b) 10% aq. K₂CO₃ c) 3 M HCl.
(ii) a) (S)-α-methylbenzylamine, THF. b) 10% aq. K₂CO₃. c) 3 M HCl.
(iii) a) (R)-α-methylbenzylamine, THF. b) 10% aq. K₂CO₃. c) 3 M HCl.

Diimine 1': The diimine 1' was prepared based on the procedure of Hencoch et al. (Hencoch, F. E.; Hampton, G.; Hauser, C. R. *J. Am. Chem. Soc.* 1969, 91, 676). Hydrazine monohydrate (1.5 mL, 30.9 mmol) in ethanol (20 mL) was added slowly to an ethanol solution (150 mL) of 2-carboxybenzaldehyde (9.52 g, 63.4 mmol). The resulting yellow solution was heated to 50° C. for 1 hr. After cooling to 0° C., the yellow solid was isolated by filtration, rinsed twice with ethanol, and dried under vacuum for 20 minutes. The product was used without further purification. Yield was 91% of a yellow powder.

Racemic 2': A THF solution (250 mL) of the diimine 1' (20.0 mmol) was treated with phenyl phosphine (20.0 mmol) and stirred for five minutes. Phthaloyl dichloride (36.1 mmol) was added to the resulting yellow slurry, and the solution was stirred at room temperature overnight. The THF was removed in vacuo to obtain a yellow oil. The oil was dissolved in a mixture of 150 mL Et₂O and 150 mL of a 10% aq. K₂CO₃ solution. The aqueous layer was isolated and rinsed three times with Et₂O. The aqueous layer was acidified by careful addition of a 2M HCl solution that had been sparged with N₂.

The white solid was filtered and rinsed once with water (50 mL) and once with Et$_2$O (50 mL). The solid was then dried under vacuum overnight to give the racemic product in 88% yield.

(R,R)-2': The racemic diazaphospholane (17.6 mmol) was dissolved in THF (250 mL) and filtered through a Schlenk frit. (S)-α-methylbenzylamine (15.5 mmol) was added to the solution, and the solution was heated gently for 5 minutes with a heat gun. Half of the THF was removed by passing N$_2$ over the solution. After seeding the solution, the Schlenk was left undisturbed for 4 days. The solution was separated from the yellow colored crystals and the solid was rinsed with 50 mL THF three times. The white solid was dried under vacuum for 15 minutes. The crystals were dissolved in 10% aq. K$_2$CO$_3$ (100 mL) and the solution was rinsed twice with Et$_2$O (50 mL). The solution was acidified with 2M HCl until gas generation stopped. The solid was isolated by cannula filtration, followed by rinses with degassed water and Et$_2$O. The solid was dried in vacuo overnight to yield the chiral acid (2.71 g, 5.1 mmol). Enantiomeric purity of the diazaphospholane was verified by converting a small sample to R,R-3a' (see below). X-ray quality crystals were grown from THF/diethyl ether using vapor diffusion. The acid was identified as R,R by X-ray crystallography. Yield=20%. $^1$H NMR (d-DMSO): δ 6.30 (d, 1H, J=8.1 Hz), 6.84 (t, 1H, J=7.3 Hz), 6.97-7.11 (m, 4H), 7.15 (d, 1H, J$_{H-P}$=16.9 Hz, PCHN), 7.16 (t, 2H, J=7.4 Hz), 7.25 (t, 1H, J=7.0 Hz), 7.47 (t, 1H, J=7.6 Hz), 7.52 (d, 1H, J=4.2 Hz, PCHN), 7.58 (t, 1H, J=7.3 Hz), 7.75 (d, 1H, J=8.0 Hz), 7.99 (m, 2H), 8.10 (d, 1H, J=7.9 Hz), 8.16 (m, 1H), 8.29 (m, 1H); $^{13}$C NMR (d-DMSO): 59.1 (d, J$_{C-P}$=19.3 Hz, PCHN), 60.8 (d, J$_{C-P}$=32.2 Hz, PCHN), peaks at 120-145 ppm have not been assigned due to the complexity, 155.4 (s, CONN), 155.9 (s, CONN), 168.0 (s, CO$_2$H), 168.2 (s, CO$_2$H); $^{31}$P NMR: δ 1.9. EMM calcd for C$_{30}$H$_{20}$N$_2$O$_6$P [M−H]$^−$: 535.1059. Found: 535.1033.

(S,S) 2': The THF solution from the isolation of the (R,R) diazaphospholane was used in this resolution procedure. The THF was removed in vacuo and the resulting oil was dissolved in 10% aq. K$_2$CO$_3$. The solution was rinsed three times with 100 mL ether, and the aqueous layer was acidified with 2M HCl. The solid was filtered by cannula and was rinsed with degassed water (50 mL) and Et$_2$O (50 mL). After drying under vacuum, 47% of the diazaphospholane was recovered (8.3 mmol). An identical procedure was used to set up the crystallization as in 1 and (R)-α-methylbenzylamine (8.2 mmol) was added. An identical workup procedure was followed to obtain the free acid. The enantiomeric purity was determined by converting a small sample to the (R)-methylbenzylamide and verifying the presence of only one diastereomer by NMR. Yield=28%. EMM calcd for C$_{30}$H$_{20}$N$_2$O$_6$P [M−H]$^−$: 535.1059. Found: 535.1040.

Synthesis of Amide-Containing Diazaphosphacycles, (R,R)- and (S,S)-3'

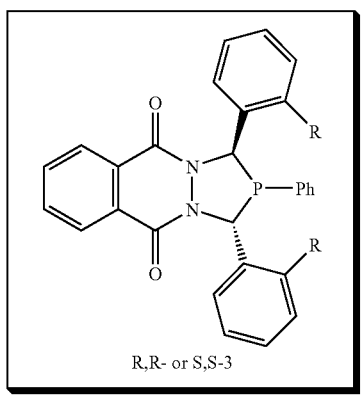

R,R- or S,S-3

-continued

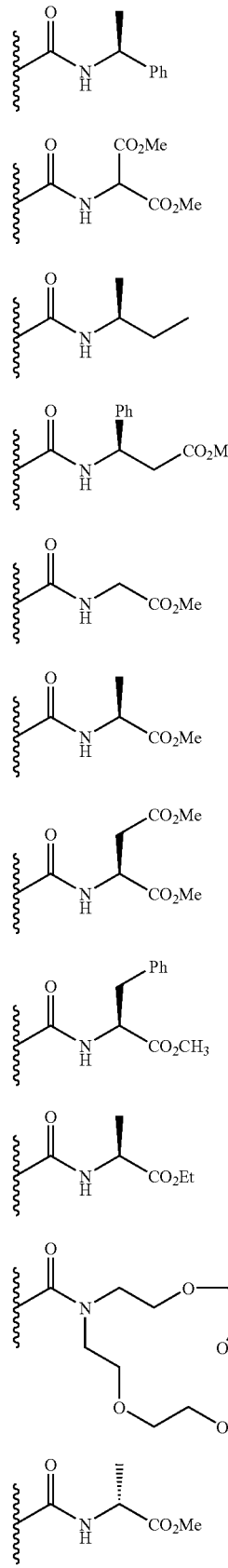

a b c d e f g h i j k

-continued

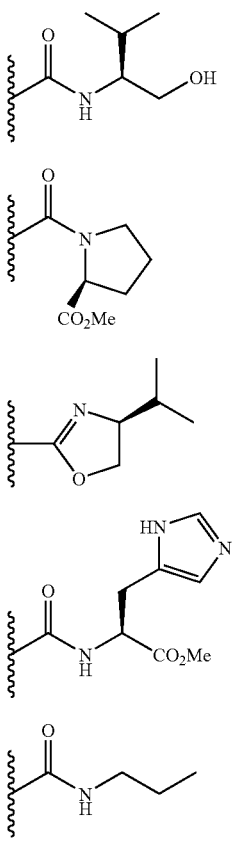

l m n o p

The compounds of formula I shown in the above chart were synthesized by the following procedures.

General Procedure for Amide-Diazaphospholane Synthesis ((R,R)-3a'-i', k', m'; (S,S)-3a', m', o'). The resolved carboxylic acid diazaphospholane (S,S)-2' or (R,R)-2' (1 mmol) was combined with 2.3 equivalents of the PyBOP® coupling reagent. Methylene chloride (75 mL) was added to the solid and stirred. This was followed by the addition of 2.3 equivalents of amine (or the hydrochloride salt) and 2.5 equivalents of diisopropylethylamine (DIEA). A further equivalent of DIEA was added to neutralize any equivalents of HCl that were added as the amine adducts. After stirring overnight (15 hours), methylene chloride was removed in vacuo and the reactions were checked for completeness by NMR. The product was dissolved in ethyl acetate and the organic layer was washed with saturated NaHCO$_3$, 3M HCl, saturated NaHCO$_3$ and H$_2$O. The organic layer was dried over magnesium sulfate and the solvent was removed. The residue was purified by flash chromatography with 2:1 CH$_2$Cl$_2$/ethyl acetate as eluent.

(R,R)-3a': Yield=42% of a white solid. $^1$H NMR (CDCl$_3$): δ 1.56 (d, 3H, J=7.1 Hz, CH$_3$), 1.59 (d, 3H, J=6.7 Hz, CH$_3$), 5.27 (quintet, 1H, J=7.1, CHCH$_3$), 5.34 (quintet, 1H, J=7.3 Hz, CHCH$_3$), 6.15 (d, 1H, J=8.1), 6.70 (t, 1H, J=7.9 Hz), 6.78 (d, 1H, J$_{H-P}$=18.6 Hz, PCHN), 6.95 (b, 1H), 7.00 (t, 1H, J=7.3 Hz), 7.06 (d, 1H, J=7.4 Hz), 7.10 (t, 2H, J=7.8 Hz), 7.18 (t, 2H, J=7.1 Hz), 7.20-7.44 (m, 12H), 7.47 (d, 1H, J=2.9 Hz, PCHN), 7.56 (d, 2H, J=6.8 Hz), 7.85 (m, 2H), 8.26 (d, 1H, J=7.8 Hz), 8.42 (d, 1H, J=8.42 Hz); $^{13}$C{$^1$H} NMR (CDCl$_3$): δ 22.8 (s, CH$_3$), 23.1 (s, CH$_3$), 49.8 (s, 2C, CHCH$_3$), 59.6 (d, J$_{C-P}$=21 Hz, PCHN), 62.8 (d, J$_{C-P}$=37 Hz, PCHN), peaks at 125-145 ppm were not assigned due to the complexity, 157.1 (s, CONN), 157.5 (s, CONN), 168.1 (s, CONH), 168.4 (s, CONH); $^{31}$P NMR (CDCl$_3$): δ 1.3 (d, J$_{P-H}$=18.6 Hz). EMM calcd for C$_{46}$H$_{39}$N$_4$O$_4$PNa [M+Na]$^+$: 765.2607. Found: 765.2608.

(R,R)-3b': Yield=72% of a white solid. $^1$H NMR (CDCl$_3$): δ 3.72 (s, 3H, OCH$_3$), 3.76 (s, 6H, OCH$_3$), 3.83 (s, 3H, OCH$_3$), 5.37 (d, 1H, J=7.3 Hz, NCH(CO$_2$CH$_3$)$_2$), 5.48 (d, 1H, J=7.4 Hz, NCH(CO$_2$CH$_3$)$_2$), 6.19 (d, 1H, J=7.9 Hz), 6.72 (m, 1H), 6.99 (d, 1H, J$_{H-P}$=17.4 Hz, PCHN), 7.05 (m, 1H), 7.08-7.50 (m, 10H), 7.67 (m, 1H), 7.82 (m, 3H), 8.18 (d, 1H, J=7.4 Hz), 8.26 (m, 1H), 8.40 (m, 1H); $^{13}$C{$^1$H} NMR (CDCl$_3$): δ 54.0 (s, CO$_2$CH$_3$), 54.1 (s, CO$_2$CH$_3$), 54.2 (s, 2C, CO$_2$CH$_3$), 57.1 (s, CH(CO$_2$CH$_3$)$_2$), 57.2 (s, CH(CO$_2$CH$_3$)$_2$), 59.6 (d, J$_{C-P}$=23 Hz, PCHN), 62.2 (d, J$_{C-P}$=36 Hz, PCHN), peaks at 125-145 ppm were not assigned due to the complexity, 157.0 (s, CONN), 157.4 (s, CONN), 167.2 (s, 2C, CO$_2$CH$_3$), 167.3 (s, CO$_2$CH$_3$), 167.4 (s, CO$_2$CH$_3$), 168.8 (s, CONH), 169.2 (s, CONH); $^{31}$P NMR (CDCl$_3$): δ 1.8 (d, J$_{P-H}$=17.4 Hz). EMM calcd for C$_{40}$H$_{35}$N$_4$O$_{12}$PNa [M+Na]$^+$: 817.1887. Found: 817.1854.

(R,R)-3c': Yield=64% of a white solid. $^1$H NMR (CDCl$_3$): δ 0.91 (t, 3H, J=7.4 Hz, CH$_2$CH$_3$), 0.97 (t, 3H, J=7.3 Hz, CH$_2$CH$_3$), 1.19 (d, 3H, J=6.6 Hz, CHCH$_3$), 1.20 (d, 3H, J=6.8 Hz, CHCH$_3$), 1.40-1.65 (m, 4H, CHCH$_2$CH$_3$), 3.95-4.20 (m, 2H, NCH(CH$_3$)CH$_2$CH$_3$), 6.10 (d, 1H, J=7.9 Hz), 6.48 (d, 1H, J=8.4 Hz), 6.68 (d, 1H, J$_{H-P}$=18.4 Hz, PCHN), 6.68 (m, 1H), 6.92 (d, 1H, J=8.4 Hz), 6.96-7.35 (m, 10H), 7.45 (d, 1H, J=3.1 Hz), 7.55 (m, 1H), 7.84 (m, 2H), 8.24 (m, 1H), 8.41 (m, 1H); $^{13}$C{$^1$H} NMR (CDCl$_3$): δ 11.1 (s, CH$_2$CH$_3$), 11.2 (s, CH$_2$CH$_3$), 21.1 (s, CHCH$_3$), 21.2 (s, CHCH$_3$), 30.3 (s, CH$_2$CH$_3$), 30.5 (s, CH$_2$CH$_3$), 47.7 (s, CHCH$_3$), 47.8 (s, CHCH$_3$), 59.5 (d, J$_{C-P}$=22 Hz, PCHN), 62.6 (d, J$_{C-P}$=37 Hz, PCHN), 157.1 (s, CONN), peaks at 125-145 ppm were not assigned due to the complexity, 157.4 (s, CONN), 168.5 (s, CONH), 168.9 (s, CONH); $^{31}$P NMR (CDCl$_3$): δ 0.5 (d, J$_{P-H}$=18.4 Hz). EMM calcd for C$_{38}$H$_{39}$N$_4$O$_4$PNa [M+Na]$^+$: 669.2607. Found: 669.2632.

(R,R)-3d': Yield=79% of a yellow solid. $^1$H NMR (CDCl$_3$): δ 3.68 (s, 3H, CO$_2$CH$_3$), 3.74 (s, 3H, CO$_2$CH$_3$), 5.67 (d, 1H, J=7.3 Hz, NHCH(Ph)CO$_2$CH$_3$), 5.77 (d, 1H, J=7.3 Hz, NHCH(Ph)CO$_2$CH$_3$), 6.09 (d, 1H, J=7.9 Hz), 6.68 (d, 1H, J$_{H-P}$=19.1 Hz, PCHN), 6.69 (m, 1H), 6.88 (d, 1H, J=7.5 Hz), 6.95-7.50 (m, 21H), 7.66 (d, 1H, J=6.3 Hz), 7.81 (m, 2H), 7.99 (d, 1H, J=7.4 Hz), 8.22 (m, 1H), 8.37 (m, 1H); $^{13}$C{$^1$H} NMR (CDCl$_3$): δ 53.4 (s, CHCO$_2$CH$_3$), 53.5 (s, CHCO$_2$CH$_3$), 57.6 (s, 2C, OCH$_3$), 59.3 (d, J$_{C-P}$=21 Hz, PCHN), 62.5 (d, J$_{C-P}$=36 Hz, PCHN), peaks at 125-140 ppm were not assigned due to the complexity, 156.7 (s, CON(N)CH), 157.2 (s, CONN), 168.4 (s, CONH), 168.7 (s, CONH), 171.8 (s, COCH$_3$), 171.9 (s, COCH$_3$); $^{31}$P NMR (CDCl$_3$): δ 1.2 (d, J$_{P-H}$=19.1 Hz). EMM calcd for C$_{48}$H$_{39}$N$_4$O$_8$PNa [M+Na]$^+$: 853.2403. Found: 853.2401.

(R,R)-3e': Yield=51% of a white solid. $^1$H NMR (CDCl$_3$): δ 3.68 (s, 3H, CO$_2$CH$_3$), 3.74 (s, 3H, CO$_2$CH$_3$), 4.06 (dd, 1H, J=18.2, 5.2 Hz, NHCH$_2$CO$_2$CH$_3$), 4.08 (dd, 1H, J=18.2, 5.2, NHCH$_2$CO$_2$CH$_3$), 4.32 (dd, 1H, J=18.2, 6.0 Hz, NHCH$_2$CO2CH3), 4.44 (dd, 1H, J=18.2, 6.4 Hz, NHCH$_2$CO$_2$CH$_3$), 6.18 (d, 1H, J=8.0 Hz), 6.70 (m, 1H), 7.04 (t, 1H, J=7.5 Hz), 7.06 (d, 1H, J$_{H-P}$=19.9 Hz, PCHN), 7.09-7.45 (m, 10H), 7.48 (d, 1H, J=3.5 Hz), 7.63 (m, 1H), 7.77-7.88 (m, 3H), 8.23 (m, 1H), 8.37 (m, 1H); $^{13}$C{H} NMR (CDCl$_3$): 42.1 (s, NHCH$_2$), 42.4 (s, NHCH$_2$), 53.0 (s, CO$_2$CH$_3$), 53.1 (s, CO$_2$CH$_3$), 59.7 (d, J$_{C-P}$=23 Hz, PCHN), 62.4 (d, J$_{C-P}$=37 Hz, PCHN), peaks at 125-140 were not assigned due to the complexity, 157.0 (s, CONN), 157.4 (s, CONN), 169.2 (s, CONH), 169.8 (s, CONH), 171.0 (s, CO$_2$CH$_3$), 171.1 (s, CO$_2$CH$_3$); $^{31}$P NMR (CDCl$_3$): δ 2.2 (d, J$_{P-H}$=19.9 Hz). EMM calcd for C$_{36}$H$_{31}$N$_4$O$_8$PNa [M+Na]$^+$: 701.1777. Found: 701.1744.

(R,R)-3f': Yield=63% of a white solid. $^1$H NMR (CDCl$_3$): δ 1.48 (d, 3H, J=7.2 Hz, CHCH$_3$), 1.49 (d, 3H, J=7.2 Hz, CHCH$_3$), 3.69 (s, 3H, CO$_2$CH$_3$), 3.76 (s, 3H, CO$_2$CH$_3$), 4.66 (dq, 1H, J=7.2, 7.2 Hz, NHCHCH$_3$), 4.78 (dq, 1H, J=7.2, 7.2 Hz, NHCHCH$_3$), 6.16 (d, 1H, J=8.3 Hz, NHCHCH$_3$), 6.71 (m, 1H), 6.77 (d, 1H, J$_{H-P}$=18.6 Hz, PCHN), 6.93 (d, 1H, J=7.7 Hz), 6.97-7.45 (m, 11H), 7.53 (d, 1H, J=7.5 Hz), 7.64 (m, 1H), 7.83 (m, 2H), 8.25 (m, 1H), 8.39 (m, 1H); $^{13}$C{$^1$H} NMR (CDCl$_3$): δ 19.0 (s, CHCH$_3$), 19.1 (s, CHCH$_3$), 49.1 (s, CHCH$_3$), 49.2 (s, CHCH$_3$), 53.1 (s, CO$_2$CH$_3$), 53.2 (s, CO$_2$CH$_3$), 59.5 (d, J$_{C-P}$=23 Hz, PCHN), 62.7 (d, J$_{C-P}$=36 Hz, PCHN), Peaks at 125-135 ppm were not assigned due to the complexity, 156.9 (s, CONN), 157.4 (s, CONN), 168.4 (CONH), 168.8 (CONH), 173.9 (s, CO$_2$CH$_3$), 174.0 (s, CO$_2$CH$_3$); $^{31}$P NMR (CDCl$_3$): δ 1.5 (d, J$_{P-H}$=18.6 Hz). EMM calcd for C$_{38}$H$_{35}$N$_4$O$_8$PNa [M+Na]$^+$: 729.2090. Found: 729.2091.

(R,R)-3g': Yield=83% of a white solid. $^1$H NMR (CDCl$_3$): δ 2.97 (dd, 2H, J=4.6, 17.2 Hz, CH$_2$CO$_2$Me), 3.07 (dd, 1H, J=4.9, 17.1 Hz, CH$_2$CO$_2$Me), 3.13 (dd, 1H, J=5.0, 17.1 Hz, CH$_2$CO$_2$Me), 3.66 (s, 3H, OCH$_3$), 3.68 (s, 3H, OCH$_3$), 3.71 (s, 3H, OCH$_3$), 3.76 (s, 3H, OCH$_3$), 4.92 (td, 1H, J=4.0, 8.1 Hz, CHCH$_2$), 5.05 (td, 1H, J=4.0, 8.1 Hz), 6.16 (d, 1H, J=8.2 Hz), 6.71 (t, 1H, J=8.3 Hz), 6.82 (d, 1H, J$_{H-P}$=18.6 Hz, PCHN), 7.02 (t, 1H, J=7.5 Hz), 7.09 (m, 3H), 7.20 (t, 3H, J=7.0 Hz), 7.37 (m, 5H), 7.66 (d, 1H, J=7.8 Hz), 7.68 (d, 1H, J=8.2 Hz), 7.83 (m, 2H), 8.31 (m, 2H); $^{13}$C{H} NMR (CDCl$_3$): δ 36.7 (s, CHCH$_2$), 36.9 (s, CHCH$_2$), 49.7 (s, 2C, CO$_2$CH$_3$), 52.8 (s, CO$_2$CH$_3$), 52.9 (s, CO$_2$CH$_3$), 53.5 (s, CHCH$_2$), 53.6 (s, CHCH$_2$), 59.6 (d, J$_{C-P}$=22 Hz, PCHN), 62.7 (d, J$_{C-P}$=37 Hz, PCHN), Peaks at 125-140 ppm were not assigned due to the complexity, 156.8 (s, CONN), 157.3 (s, CONN), 168.6 (s, CONH), 169.0 (s, CONH), 171.77 (s, CO$_2$CH$_3$), 171.81 (s, CO$_2$CH$_3$), 172.2 (s, CO$_2$CH$_3$), 172.4 (s, CO$_2$CH$_3$); $^{31}$P NMR (CDCl$_3$): δ 2.3 (d, J$_{P-H}$=18.6 Hz). EMM calcd for C$_{42}$H$_{39}$N$_4$O$_{12}$PNa [M+Na]$^+$: 845.2200. Found: 845.2231.

(R,R)-3h': Yield=87% of a white solid. $^1$H NMR (CDCl$_3$): δ 3.08-3.32 (m, 4H, CHCH$_2$Ph), 3.64 (s, 3H, CO$_2$CH$_3$), 3.71 (s, 3H, CO$_2$CH$_3$), 4.87 (dt, 1H, J=7.5, 5.7 Hz, NHCHCH$_2$), 5.03 (dt, 1H, J=8.1, 6.1 Hz), 6.15 (d, 1H, J=6.9 Hz), 6.69 (m, 1H), 6.70 (d, 1H, J$_{H-P}$=18.8 Hz, PCHN), 6.78 (d, 1H, J=8.0), 6.90-7.45 (m, 23H), 7.85 (m, 2H), 8.29 (m, 1H), 8.42 (m, 1H); $^{13}$C{$^1$H} NMR (CDCl$_3$): δ 38.5 (s, CHCH$_2$), 38.8 (s, CHCH$_2$), 53.0 (s, CO$_2$CH$_3$), 53.1 (s, CO$_2$CH$_3$), 52.48 (s, CHCH$_2$), 52.52 (s, CHCH$_2$), 59.6 (d, J$_{C-P}$=21 Hz, PCHN), 62.6 (d, J$_{C-P}$=36 Hz, PCHN), peaks at 125-140 were not assigned due to the complexity, 156.8 (s, CONN), 157.2 (s, CONN), 168.5 (s, CONH), 168.8 (s, CONH), 172.4 (s, CO$_2$CH$_3$), 172.6 (s, CO$_2$CH$_3$); $^{31}$P NMR (CDCl$_3$): δ 2.4 (d, J$_{P-H}$=18.8 Hz). EMM calcd for C$_{50}$H$_{43}$N$_4$O$_8$PNa [M+Na]$^+$: 881.2716. Found: 881.2717.

(R,R)-3i': Yield=93% of a white solid. $^1$H NMR (CDCl$_3$): δ 1.26 (t, 3H, J=7.1 Hz), 1.30 (t, 3H, J=7.3 Hz), 1.49 (t, 6H, J=7.1 Hz), 4.18 (q, 2H, J=7.2 Hz, OCH$_2$CH$_3$), 4.23 (q, 2H, J=7.1 Hz), 4.66 (dq, 1H, J=7.3, NHCHCH$_3$), 4.77 (dq, 1H, J=7.3 Hz, NHCHCH$_3$), 6.16 (d, 1H, J=7.9 Hz), 6.71 (m, 1H), 6.79 (d, 1H, J$_{H-P}$=19.6 Hz, PCHN), 6.85 (d, 1H, J=7.8 Hz), 6.95-7.43 (m, 11H), 7.46 (d, 1H, J=7.0 Hz), 7.63 (m, 1H), 7.83 (m, 2H), 8.26 (m, 1H), 8.39 (m, 1H); $^{13}$C{$^1$H} NMR (CDCl$_3$): δ 14.8 (s, CH$_2$CH$_3$), 14.9 (s, CH$_2$CH$_3$), 19.2 (s, CHCH$_3$), 19.3 (s, CHCH$_3$), 49.2 (s, 2C, CHCH$_3$), 59.6 (d, J$_{C-P}$=23 Hz, PCHN), 62.1 (s, CO$_2$CH$_2$), 62.3 (s, CO$_2$CH$_2$), 62.8 (d, J$_{C-P}$=35 Hz, PCHN), Peaks at 125-140 ppm were not assigned due to the complexity, 156.9 (s, CONN), 157.4 (s, CONN), 168.4 (s, CONH), 168.7 (s, CONH), 173.5 (s, CO$_2$CH$_2$), 173.6 (s, CO$_2$CH$_2$); $^{31}$P NMR (CDCl$_3$): δ 1.7 (d, J$_{P-H}$=19.6 Hz). EMM calcd for C$_{40}$H$_{39}$N$_4$O$_8$PNa [M+Na]$^+$: 757.2403. Found: 757.2412.

(R,R)-3k': Yield=81% of a white solid. $^1$H NMR (CDCl$_3$): δ 1.48 (d, 3H, J=7.2 Hz, CHCH$_3$), 1.51 (d, 3H, J=7.2 Hz, CHCH$_3$), 3.61 (s, 3H, CO$_2$CH$_3$), 3.68 (s, 3H, CO$_2$CH$_3$), 4.72 (dq, 1H, J=7.7, 7.3 Hz, NHCHCH$_3$), 4.83 (dq, 1H, J=8.0, 7.4 Hz, NHCHCH$_3$), 6.17 (d, 1H, J=8.0 Hz), 6.68 (t, 1H, J=7.9 Hz), 7.04 (t, 1H, J=7.5 Hz), 7.12 (d, 1H, J$_{H-P}$=18.7 Hz, PCHN), 7.10-7.18 (m, 2H), 7.20-7.29 (m, 4H), 7.29-7.44 (m, 3H), 7.57 (d, 1H, J=3.5 Hz), 7.62 (m, 2H), 7.83 (m, 2H), 8.02 (m, 1H), 8.24 (m, 1H); $^{13}$C{$^1$H} NMR (CDCl$_3$): δ; $^{31}$P NMR (CDCl$_3$): δ 1.9 (d, J$_{P-H}$=18.7). EMM calcd for C$_{38}$H$_{35}$N$_4$O$_8$PNa [M+Na]$^+$: 729.2090. Found: 729.2057.

(R,R)-3m': Yield=20% of a white solid. $^1$H NMR (CDCl$_3$): δ (main product) 1.6-2.5 (m, 8H, CH$_2$), 3.55 (s, 3H, CO$_2$CH$_3$), 3.25-3.80 (m, 4H, C(O)NCH$_2$), 4.68 (dd, 1H, J=8.1, 4.8 Hz, CHCO$_2$CH$_3$), 4.79 (dd, 1H, J=8.4, 6.0 Hz, CHCO$_2$CH$_3$), 6.05 (d, 1H, J=8.2 Hz), 6.35 (d, 1H, J$_{H-P}$=20.0 Hz, PCHN), 6.61 (t, 1H, J=7.4 Hz), 6.8-7.5 (m, 15H), 7.79 (m, 2H), 8.22 (m, 1H), 8.32 (m, 1H); $^{13}$C{$^1$H} NMR (CDCl$_3$): δ (main product) 25.87 (s, NCH$_2$CH$_2$), 25.90 (s, NCH$_2$CH$_2$), 30.3 (s, NCHCH$_2$), 30.4 (s, NCHCH$_2$), 50.2 (s, NCH$_2$CH$_2$), 50.7 (s, NCH$_2$CH$_2$), 52.8 (s, CO$_2$CH$_3$), 53.0 (s, CO$_2$CH$_3$), 58.7 (d, J$_{C-P}$=20 Hz, PCHN), 59.1 (s, NCHCO$_2$CH$_3$), 59.2 (s, NCHCO$_2$CH$_3$), 60.6 (d, J$_{C-P}$=38 Hz, PCHN), peaks at 125-140 ppm were not assigned due to the complexity, 156.9 (s, CONN), 157.1 (s, CONN), 169.5 (s, CONCH), 169.7 (s, CONCH), 173.1 (s, CO$_2$CH$_3$), 173.3 (s, CO$_2$CH$_3$); $^{31}$P NMR (CDCl$_3$): δ −1.2 (d, J$_{P-H}$=20 Hz, main peak), and other peaks at 0.0 and −4.4 with area ratio 100:40:8. EMM calcd for C$_{42}$H$_{39}$N$_4$O$_8$PNa [M+Na]$^+$: 781.2403. Found: 781.2406.

(S,S)-3a': Yield=88% of a white solid. $^1$H NMR (CDCl$_3$): δ 1.49 (d, 3H, J=6.9 Hz, CHCH$_3$), 1.56 (d, 3H, J=6.9 Hz, CHCH$_3$), 5.19 (dq, 1H, J=7.3, 6.9 Hz, NHCHCH$_3$), 5.29 (dq, 1H, J=7.3, 6.9 Hz, NHCHCH$_3$), 6.06 (d, 1H, J=8.1 Hz), 6.60 (d, 1H, J$_{H-P}$=19.0 Hz, PCHN), 6.66 (m, 1H), 6.77 (d, 1H, J=7.4 Hz), 6.97-7.08 (m, 6H), 7.15-7.43 (m, 16H), 7.55 (d, 1H, J=7.7 Hz), 7.84 (m, 2H), 8.24 (m, 1H), 8.41 (m, 1H); $^{13}$C{$^1$H} NMR (CDCl$_3$): δ 22.7 (s, CHCH$_3$), 23.2 (s, CHCH$_3$), 50.2 (s, CHCH$_3$), 50.3 (s, CHCH$_3$), 59.4 (d, J$_{C-P}$=22 Hz, PCHN), 62.4 (d, J$_{C-P}$=37 Hz, PCHN), Peaks at 125-145 not assigned due to the complexity, 156.9 (s, CONN), 157.2 (s, CONN), 168.3 (CONH), 168.7 (CONH); $^{31}$P NMR (CDCl$_3$): δ 1.6 (d, J$_{P-H}$=19.0 Hz). EMM calcd for C$_{46}$H$_{39}$N$_4$O$_4$PNa [M+Na]$^+$: 765.2607. Found: 765.2634.

(S,S)-3p': Yield=94% of a white solid. $^1$H NMR (CDCl$_3$): δ 0.90 (t, 3H, J=7.5 Hz, CH$_2$CH$_3$), 0.94 (t, 3H, J=7.4 Hz, CH$_2$CH$_3$), 1.46-1.66 (m, 4H, CH$_2$CH$_2$CH$_3$), 3.22-3.43 (m, 4H, NHCH$_2$CH$_2$), 6.12 (d, 1H, J=8.0 Hz), 6.70 (d, 1H, J$_{H-P}$=18.7 Hz, PCHN), 6.63-6.75 (m, 2H), 6.93-7.35 (m, 11H), 7.45 (d, 1H, J=3.5 Hz), 7.53 (m, 1H), 7.83 (m, 2H), 8.23 (m, 1H), 8.38 (m, 1H); $^{13}$C{$^1$H} NMR (CDCl$_3$): δ 12.2 (s, 2C, CH$_2$CH$_3$), 23.5 (s, CH$_2$CH$_2$CH$_3$), 23.6 (s, CH$_2$CH$_2$CH$_3$), 42.37 (s, NHCH$_2$CH$_2$), 42.41 (s, NHCH$_2$CH$_2$), 59.6 (d, J$_{C-P}$=21 Hz, PCHN), 62.7 (d, J$_{C-P}$=36 Hz, PCHN), Peaks at 124-140 ppm were not assigned due to the complexity, 157.0 (s, CONN), 157.4 (s, CONN), 169.1 (s, CONH), 169.6 (s, CONH); $^{31}$P NMR (CDCl$_3$): δ 1.0 (d, J$_{P-H}$=18.7 Hz). EMM calcd for C$_{36}$H$_{35}$N$_4$O$_4$PNa [M+Na]$^+$: 641.2294. Found: 641.2263.

(S,S)-3m': Yield=91% of a white solid. $^1$H NMR (CDCl$_3$): δ (main product) 1.7-2.4 (m, 8H, CH$_2$), 3.35 (s, 3H, CO$_2$CH$_3$), 3.52 (s, 3H, CO$_2$CH$_3$), 3.24-4.03 (m, 4H, C(O)NCH$_2$), 4.48 (dd, 1H, J=8.3, 4.4 Hz, CH$_2$CHCO$_2$CH$_3$), 4.67

(dd, 1H, J=9.1, 3.3 Hz, $CH_2CHCO_2CH_3$), 6.04 (d, 1H, J=7.9 Hz), 6.50 (d, 1H, $J_{H-P}$=18.4 Hz, PCHN), 6.62 (t, 1H, J=7.8 Hz), 6.9-7.5 (m, 12H), 7.83 (m, 2H), 8.27 (m, 1H), 8.47 (m, 1H); $^{13}C\{^1H\}$ NMR ($CDCl_3$): δ 25.3 (s, $NCH_2CH_2$), 25.6 (s, $NCH_2CH_2$), 30.20 (s, $NCHCH_2$), 30.24 (s, $NCHCH_2$), 49.4 (s, 2C, $NCH_2CH_2$), 52.7 (s, $CO_2CH_3$), 52.8 (s, $CO_2CH_3$), 58.9 (s, $NCHCO_2CH_3$), 59.0 (d, $J_{C-P}$=20 Hz, PCHN), 59.3 (s, $NCHCO_2CH_3$), 62.7 (d, $J_{C-P}$=37 Hz), peaks at 125-140 ppm were not assigned due to the complexity, 156.9 (s, CONN), 157.1 (s, CONN), 169.7 (s, $CONCH_2$), 169.9 (s, $CONCH_2$), 172.9 (s, $CO_2CH_3$), 173.3 (s, $CO_2CH_3$); $^{31}P$ NMR ($CDCl_3$): δ −0.88 (d, $J_{P-H}$=18.4 Hz), additional peak at −2.7 with 11% of integrated area. EMM calcd for $C_{42}H_{39}N_4O_8PNa$ [M+Na]$^+$: 781.2403. Found: 781.2401.

Synthesis of (R,R)-3j': The synthesis procedure was identical to the general procedure. However, the product moved too slowly through the column using $CH_2Cl_2$/ethyl acetate and was eluted using methanol. After column chromatography, the product was not sufficiently pure, and the product was therefore washed again using the general procedure described above. Yield=34% of a white solid. $^1H$ NMR ($CDCl_3$): δ 3.36-4.06 (m, 40H, crown ether), 6.05 (d, 1H, J=7.9 Hz), 6.15 (d, 1H, $J_{H-P}$=20.1 Hz), 6.60 (t, 1H, J=8.1 Hz), 6.90-7.38 (m, 12H), 7.82 (m, 2H), 8.25 (m, 1H), 8.40 (m, 1H); $^{13}C\{^1H\}$ NMR ($CDCl_3$): 47.1 (s, $NCH_2$), 48.2 (s, $NCH_2$), 51.4 (s, $NCH_2$), 52.0 (s, $NCH_2$), 59.5 (d, $J_{C-P}$=30 Hz, PCHN), 63.2 (d, $J_{C-P}$=38 Hz, PCHN), 69.0-72.5 (crown ether), peaks at 125-140 ppm were not assigned due to the complexity, 156.8 (s, CONN), 157.0 (s, CONN), 171.2 (s, $CON(CH_2)_2$), 171.4 (s, $CON(CH_2)_2$); $^{31}P$ NMR ($CDCl_3$): δ −1.0 (broad). EMM calcd for $C_{50}H_{59}N_4O_{12}PNa$ [M+Na]$^+$: 961.3765. Found: 961.3714.

Synthesis of (S,S)-3o': The resolved carboxylic acid diazaphospholane (1 mmol) was combined with 2.3 equivalents of the PyBOP® coupling reagent. Methylene chloride (75 mL) was added to the solid and stirred. This was followed by the addition of 2.3 equivalents of the amine salt and 7 equivalents of diisopropylethylamine (DIEA). After stirring overnight (15 hours), methylene chloride was removed in vacuo and the reaction was checked for completeness by NMR. The product was dissolved in 2M HCl and the aqueous layer was rinsed with ethyl acetate. After neutralizing the HCl by adding a saturated solution of $NaHCO_3$, the product was extracted with methylene chloride. Flash chromatography was performed with 6:1 $CH_2Cl_2$/methanol as eluent. Yield=34% of a white solid. $^1H$ NMR ($CDCl_3$): δ 3.18 (m, 4H, $NHCHCH_2$), 3.57 (s, 3H, $CO_2CH_3$), 3.77 (s, 3H, $CO_2CH_3$), 4.80-4.95 (m, 2H, $NHCHCH_2$), 6.06 (d, 1H, J=8.2 Hz), 6.58 (d, 1H, $J_{H-P}$=16.5 Hz, PCHN), 6.69 (t, 1H, J=7.1 Hz), 6.82 (s, 1H), 6.83 (m, 1H), 7.00 (s, 1H), 7.03 (m, 1H), 7.11 (m, 4H), 7.19 (m, 1H), 7.33-7.44 (m, 5H), 7.49 (s, 1H), 7.60 (s, 1H), 7.61-7.69 (m, 2H), 7.90 (m, 3H), 8.27 (m, 1H), 8.51 (m, 1H); $^{13}C\{^1H\}$ NMR ($CDCl_3$): δ 29.0 (s, $CHCH_2$), 30.3 (s, $CHCH_2$), 53.0 (s, $CO_2CH_3$), 53.3 (s, $CO_2CH_3$), 53.8 (s, $CHCH_2$), 54.1 (s, $CHCH_2$), 59.2 (d, $J_{C-P}$=19 Hz, PCHN), 62.5 (d, $J_{C-P}$=33 Hz, PCHN), peaks at 120-145 were not assigned due to the complexity, 156.8 (s, CONN), 157.4 (s, CONN), 169.1 (s, CONH), 169.6 (s, CONH), 172.1 (s, $CO_2CH_3$), 172.4 (s, $CO_2CH_3$); $^{31}P$ NMR ($CDCl_3$): δ 2.6 (d, $J_{P-H}$=16.5 Hz). EMM calcd for $C_{44}H_{39}N_8O_8PNa$ [M+Na]$^+$: 861.2656. Found: 861.2687.

Synthesis of Phosphine-Oxazolines (R,R)- and (S,S)-3n': The procedure used was based on literature precedent (see Peer, M.; de Jong, J. C.; Kiefer, M.; Langer, T.; Rieck, H.; Schell, H.; Sennhenn, P.; Sprinz, J.; Steinhagen, H.; Wiese, B.; Helmchen, G. *Tetrahedron* 1996, 52, 7547). The resolved carboxylic acid diazaphospholane (1 mmol) was combined with 2.3 equivalents of the PyBOP® coupling reagent and 2.5 equivalents of L-valinol. Methylene chloride (75 mL) was added to the solid and stirred. This was followed by the addition of 2.5 equivalents of diisopropylethylamine (DIEA). After stirring overnight (15 hours), solvent was removed in vacuo and the reactions were checked for completeness by NMR. The product was dissolved in ethyl acetate, and the organic layer was washed with saturated $NaHCO_3$, 3M HCl, saturated $NaHCO_3$ and $H_2O$. The organic layer was dried over magnesium sulfate and the solvent was removed to give the crude products (R,R)- and (S,S)-3l' as an oil. This product was used without further purification.

The oil was combined with 2.1 equivalents of p-toluenesulfonyl chloride in a Schlenk flask and placed under $N_2$. $CH_2Cl_2$ (100 mL), triethyl amine (1.0 mL) and a grain of DMAP were added. The solution was stirred for over 24 hours. Water (3 mL) was added to the solution, and the resulting mixture stirred for 1 hour. A further 50 mL of $CH_2Cl_2$ was added to the solution, and the organic layer was rinsed 3 times with degassed $H_2O$ (50 mL). The organic layer was dried over $MgSO_4$, filtered, and the solvent was removed under reduced pressure. The product was purified by flash chromatography (11:1 $CH_2Cl_2$/ethyl acetate).

(R,R)-3n': Yield=14% of a white solid. $^1H$ NMR ($CDCl_3$): δ 0.57 (d, 3H, J=6.6 Hz, $CHCH_3$), 0.62 (d, 3H, J=6.5 Hz, $CHCH_3$), 0.68 (d, 3H, J=6.5 Hz, $CHCH_3$), 0.74 (d, 3H, J=6.7 Hz, $CHCH_3$), 1.45 (m, 1H, $CHCH(CH_3)_2$), 1.57 (m, 1H, $CHCH(CH_3)_2$), 3.74-4.39 (m, 6H), 6.15 (d, 1H, J=7.8 Hz), 6.72 (t, 1H, J=7.2 Hz), 6.94-7.39 (m, 9H), 7.57 (d, 1H, J=14.8 Hz, PCHN), 7.78 (m, 1H), 7.84 (m, 2H), 7.95 (d, 1H, J=4.1 Hz), 8.02 (m, 1H), 8.29 (m, 1H), 8.43 (m, 1H); $^{13}C\{^1H\}$ NMR ($CDCl_3$): δ 19.1 (s, $CHCH_3$), 19.3 (s, $CHCH_3$), 19.6 (s, 2C, $CHCH_3$), 33.4 (s, $CH(CH_3)_2$), 34.0 (s, $CH(CH_3)_2$), 61.0 (d, $J_{C-P}$=21 Hz, PCHN), 62.9 (d, $J_{C-P}$=34 Hz, PCHN), 70.1 (s, $OCH_2$), 70.5 (s, $OCH_2$), 74.4 (s, NCH), 74.5 (s, NCH), peaks at 120-145 ppm were not assigned due to the complexity, peaks above 145 ppm were not identified; $^{31}P$ NMR ($CDCl_3$): δ −3.0 (broad). EMM calcd for $C_{40}H_{40}N_4O_4P$ [M+H]$^+$: 671.2787. Found: 671.2759.

(S,S)-3n': Yield=11% of a white solid. $^1H$ NMR ($CDCl_3$): δ 0.50 (d, 3H, J=6.6 Hz, $CHCH_3$), 0.52 (d, 3H, J=6.9 Hz, $CHCH_3$), 0.62 (d, 3H, J=6.6 Hz, $CHCH_3$), 0.68 (d, 3H, J=6.7 Hz, $CHCH_3$), 1.37 (m, 1H, $CHCH(CH_3)_2$), 1.56 (m, 1H, $CHCH(CH_3)_2$), 3.87-4.01 (m, 4H, $OCH_2CHN$), 4.19-4.33 (m, 2H, $NCHCH_2O$), 6.13 (d, 1H, J=8.3 Hz), 6.71 (t, 1H, J=7.1 Hz), 6.97-7.39 (m, 9H), 7.83 (m, 3H), 8.01 (m, 1H), 8.07 (d, 1H, J=3.8 Hz), 8.10 (d, 1H, $J_{H-P}$=15.9 Hz), 8.31 (m, 1H), 8.42 (m, 1H); $^{13}C\{^1H\}$ NMR ($CDCl_3$): δ 18.5 (s, $CHCH_3$), 18.7 (s, $CHCH_3$), 19.0 (s, $CHCH_3$), 19.6 (s, $CHCH_3$), 32.7 (s, $CH(CH_3)_2$), 33.9 (s, $CH(CH_3)_2$), 60.4 (d, $J_{C-P}$=21 Hz, PCHN), 62.9 (d, $J_{C-P}$=36 Hz, PCHN), 69.4 (s, $OCH_2$), 70.1 (s, $OCH_2$) 74.1 (s, NCH), 74.2 (s, NCH), peaks at 120-145 were not assigned due to the complexity, peaks above 145 were not identified; $^{31}P$ NMR ($CDCl_3$): δ −5.5 (broad). EMM calcd for $C_{40}H_{39}N_4O_4$ P [M+H]$^+$: 671.2787. Found: 671.2813.

Asymmetric Allylic Alkylation

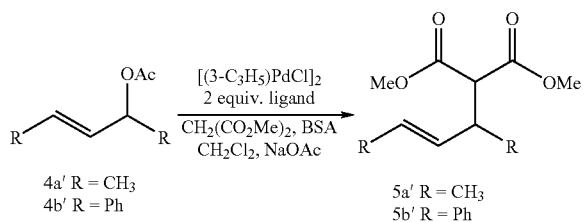

4a' R = CH₃
4b' R = Ph

5a' R = CH₃
5b' R = Ph

General Procedure for Stereoselective Allylic Alkylation: Dry CH$_2$Cl$_2$ (2.0 mL) was added to a mixture of [(η$^3$-C$_3$H$_5$)PdCl]$_2$ (1.8 mg, 5 μmol), diazaphosphacycle (20 μmol), NaOAc (approx. 5 mg), and if used AgPF$_6$/NaPF$_6$ (about 5 mg) in a septum-sealed vial under N$_2$. After stirring the solution at room temperature for 15 minutes, N,O-bis(trimethylsilyl)acetamide (0.7 mL, 3 mmol), dimethyl malonate (0.3 mL, 3 mmol), and the allyl acetate (1.0 mmol) were added. This solution was stirred for 17 hours at room temperature. The solutions were diluted with 6 mL of 5:1 hexane/ethyl acetate and filtered twice through plugs of silica. The enantiomeric excess and yield of 5a' were determined by chiral GC (β-DEX 120 column from Supelco, 30 mm×0.25 mm ID, undecane as internal standard). The absolute configuration of the product was determined by comparison of the HPLC retention times with literature values (Nettekoven, U.; Widhalm, M.; Kalchhauser, H.; Kamer, P. C. J.; van Leeuwen, P. W. N. M.; Lutz, M.; Spek, A. L. *J. Org. Chem.* 2001, 66, 759-770). The enantiomeric excess of 5b' was determined by chiral HPLC (Daicel's ChiralCel OD column with 99:1 hexane/isopropanol as mobile phase). Absolute configuration was determined by comparison of optical rotation with literature (Sprinz, J.; Helmchen, G. *Tet. Lett.* 1993, 34, 1769). Yields of 5b' were determined by mass after dissolving residue in hexane, filtering, and removing solvent. Samples that had less than 100% conversion had the ratio of starting material to product accurately measured by NMR (relaxation delay=20 seconds). This ratio was used to determine the mass of the product obtained.

Compounds of the invention were tested to assess their utility as chiral phosphines in the stereoselctive allylic alkylation reaction shown above. Results are shown in Table 1. Unexpectedly large salt effects on the catalytic reaction rates and enantioselectivities were observed (see Table 1). In all cases examined, sodium hexafluorophosphate was as effective as the silver salt. These results stand in contrast to previous reports of lowered enantiomeric excesses in allylic alkylations performed with AgPF$_6$. See, e.g., Porte, A. M.; Reibenspies, J.; Burgess, K. *J. Am. Chem. Soc.* 1998, 120, 9180.

TABLE 1

Pd-catalyzed Allylic Alkylation Results

| Substrate | Ligand | With AgPF$_6$ ee (%)$^d$ | With AgPF$_6$ Yield$^{b,d}$ (%) | Without AgPF$_6$ ee (%)$^d$ | Without AgPF$_6$ Yield$^{b,d}$ (%) |
|---|---|---|---|---|---|
| 4a | R,R-3a | 52(16) (S)$^{a,d}$ | 87(9) | 57(4) (S) | 78(10) |
| 4a | R,R-3b | 73(2) (S)$^a$ | 20(2) | 47(10) (S) | 8(2) |
| 4a | R,R-3c | 53(10) (S)$^a$ | 88(4) | 49(5) (S) | 68(16) |
| 4a | R,R-3d | 51(4) (S)$^a$ | 48(11) | 48(4) (S) | 26(7) |
| 4a | R,R-3e | 46(6) (S)$^a$ | 66(11) | 29(3) (S) | 30(9) |
| 4a | R,R-3f | 92(1) (S)$^a$ | 92(1) | 53(4) (S) | 71(7) |
| 4a | R,R-3g | 89(1) (S)$^a$ | 94(4) | 89(1) (S) | 84(3) |
| 4a | R,R-3h | 83(1) (S)$^a$ | 84(5) | 46(1) (S) | 29(5) |
| 4a | R,R-3i | 92(1) (S)$^a$ | 86(10) | 47(1) (S) | 65(3) |
| 4a | R,R-3j | 56(9) (R)$^a$ | 19(8) | 9(2) (R) | 4(1) |
| 4a | R,R-3k | 84(1) (S)$^a$ | 77(16) | 32(1) (S) | 23(9) |
| 4a | R,R-3m | 11(4) (S)$^a$ | 32(3) | 20(1) (S) | 8(2) |
| 4a | R,R-3n | 38(4) (S)$^a$ | 26(5) | | |
| 4a | S,S-3a | 59(4) (R)$^a$ | 87(5) | 50(3) (R) | 100(2) |
| 4a | S,S-3o | 55(6) (S)$^a$ | 5(2) | 44(4) (S) | 88(4) |
| 4a | S,S-3p | 40(1) (R)$^a$ | 16(5) | 30(6) (R) | 38(15) |
| 4a | S,S-3m | 54(3) (S)$^a$ | 14(3) | 34(2) (S) | 2(1) |
| 4a | S,S-3n | 64(1) (R)$^a$ | 92(7) | 60 (R) | 18 |
| 4b | R,R-2 | 71(1)$^c$(S) | 32(8) | 50(1)(S) | 13(1) |
| 4b | R,R-3f | 92(1)$^c$ (S) | 61(5) | 97(1)(S) | 92(6) |
| 4b | R,R-3m | −56$^c$ (R) | 26 | −19(2) (R) | 36(4) |
| 4b | S,S-3a | 91(6)$^c$ (R) | >95 | −75(1) (R) | 88(1) |
| 4b | S,S-3o | −9(1)$^c$(R) | 8(1) | 97(1)(S) | 99(2) |
| 4b | S,S-3p | −64(2)$^c$(R) | 34(1) | −67(1) (R) | 78(10) |

$^a$Determined by GC (β-DEX 120).
$^b$Isolated yields.
$^c$Determined by HPLC (ChiralCel OD).
$^d$Numbers in parentheses are standard deviations for multiple measurements.

Asymmetric Hydrogenation

A.

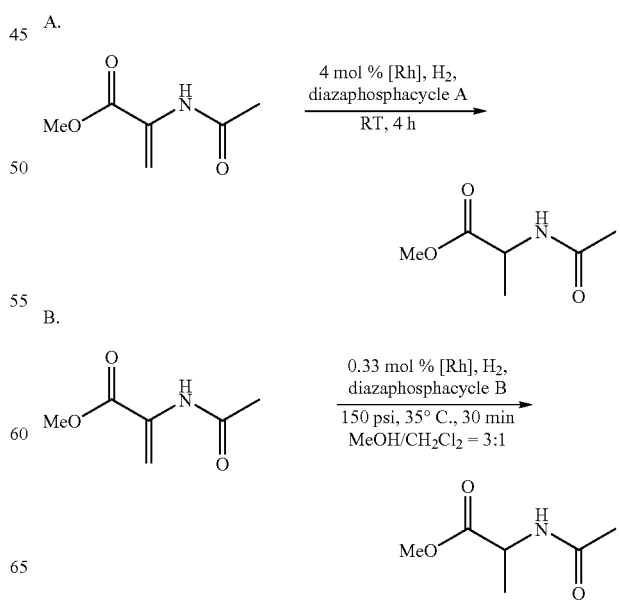

B.

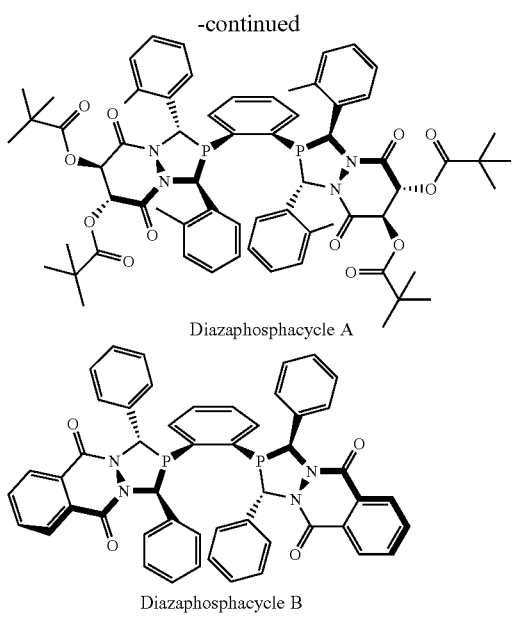

Diazaphosphacycle A

Diazaphosphacycle B

Hydrogenation of the above acrylate in the presence of Rh and diazaphosphacycles of the invention were carried out. Use of diazaphosphacycle A at room temperature resulted in an e.e. of 50% at 100% conversion. By comparison, use of diazaphosphacycle B at 150 psi $H_2$ at 35° C. resulted in an e.e. of 96.5% at 100% conversion.

Palladium Catalyzed Cross-Coupling Reaction

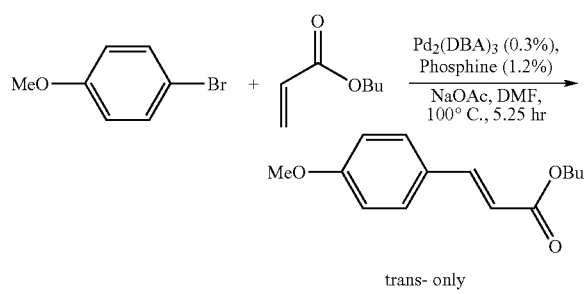

trans- only t-Butyl acrylate was coupled to 4-bromoanisole under Heck reaction conditions as shown in the scheme above. Table 2 shows that modest to excellent yields may be obtained with transition metal complexes formed from invention diazaphosphacycles.

General procedure for Heck reactions using NaOAc and $Pd_2(dba)_3$ in DMF at 100° C. Inside an inert atmosphere glove box, $Pd_2(dba)_3$ (4.7 μmol), NaOAc (1.8 mmol), and the appropriate phosphine (19.2 μmol) were weighed into an oven-dried vial before adding a stir bar and sealing the vial with a rubber septa. The vial was then brought out of the glove box and, while under a positive pressure of $N_2$, bromoanisole (1.6 mmol), dimethylformamide (DMF, 4.3 mL) and butyl acrylate (1.7 mmol) were added respectively by gastight syringe. The vial was then placed in a 100° C. silicone oil bath and left to stir for 5.25 hours. After allowing the solution to cool, it was diluted with a 1:1 mixture of $CH_2Cl_2$ and ethyl acetate (EtOAc) and then filtered through a small plug of silica. The yields were analyzed by either gas chromatograph (undecane added after filtration as an internal standard) or by isolating the product by column chromatography (5:1 hexane:ether).

TABLE 2

| R | R' | % Yield |
|---|----|---------|
| Ph | Ph | 15 |
| Ph | (1-phenylethyl-2-benzamido group) | 18 |
| Ph | (2-(carboxymethoxy)phenyl t-butyl group) | 19 |
| Ph | o-tolyl | 29 |
| Ph | 1-naphthyl | 87 |
| Cy | 1-naphthyl | 90 |
| Control: | P(o-tolyl)$_3$ | 17 |

Hydroformylation Procedure

Rhodium-catalyzed hydroformylation of allyl benzoate in the presence of the diazaphospholane 6 yields aldehydes with quantitative conversion and high regioselectivity.

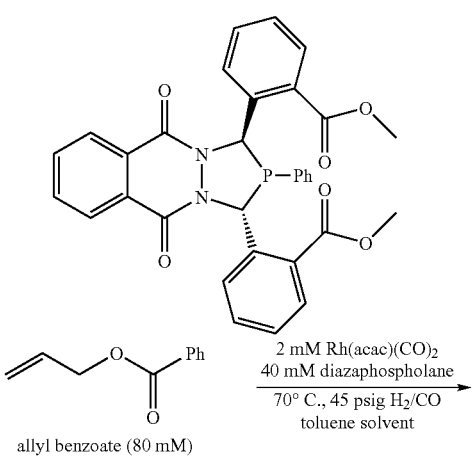

allyl benzoate (80 mM)

2 mM Rh(acac)(CO)$_2$
40 mM diazaphospholane
70° C., 45 psig $H_2$/CO
toluene solvent

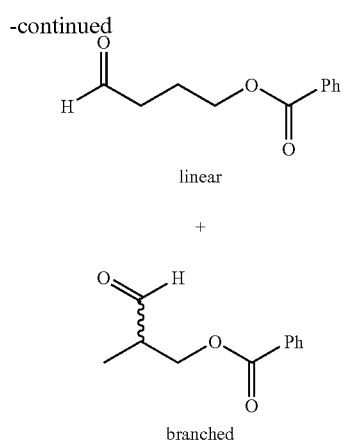

linear

+ branched

A pressure bottle was loaded with 1 mL of a toluene solution comprising 2 mM Rh(acac)(CO)$_2$, 80 mM allyl benzoate, and 40 mM racemic diazaphospholane 6. The bottle was pressurized to 45 psig with 1:1 H$_2$:CO gas and warmed to 70° C. for 16 hours. After cooling to room temperature and venting of the gas, the product was analyzed. Allyl benzoate was completely converted to aldehydes with a 25:2 regioselectivity favoring the linear aldehyde. Linear aldehyde $^1$H NMR (CDCl$_3$): δ 9.91 (t, 1H, CHO), 2.62 (t, 2H, CH$_2$CHO), 2.14 (tt, 2H, CH$_2$CH$_2$CH$_2$CHO), 4.43 (t, 2H, OCH$_2$CH$_2$CH$_2$CHO). Branched aldehyde $^1$H NMR (CDCl$_3$): δ 9.85 (d, 1H, CHO), 4.58 (d, 2H, —OCH$_2$—), 1.26 (d, 3H, CH$_3$CH(COH)CH$_2$O—).

Solid Phase Synthesis and Use of Diazaphosphacycles

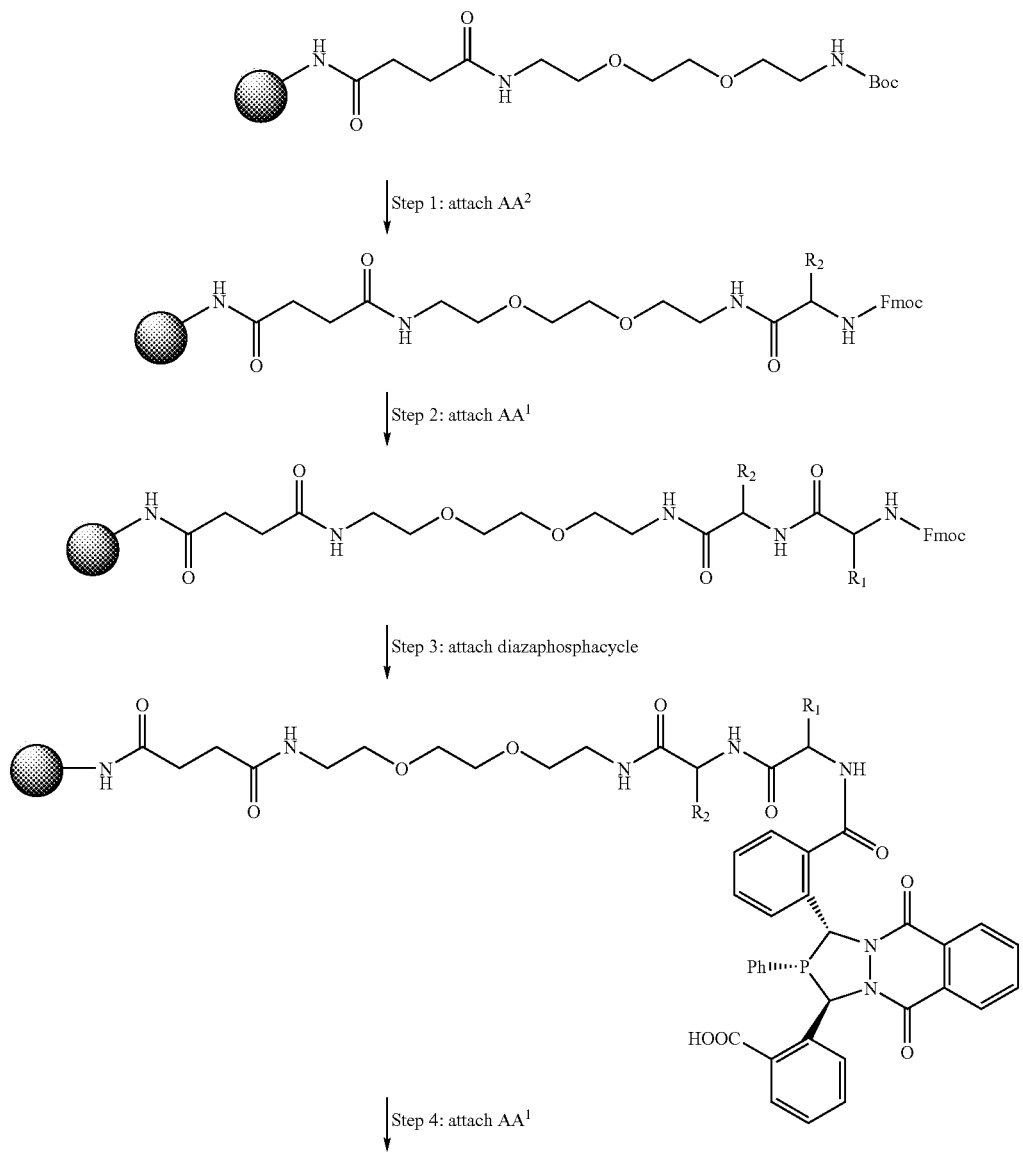

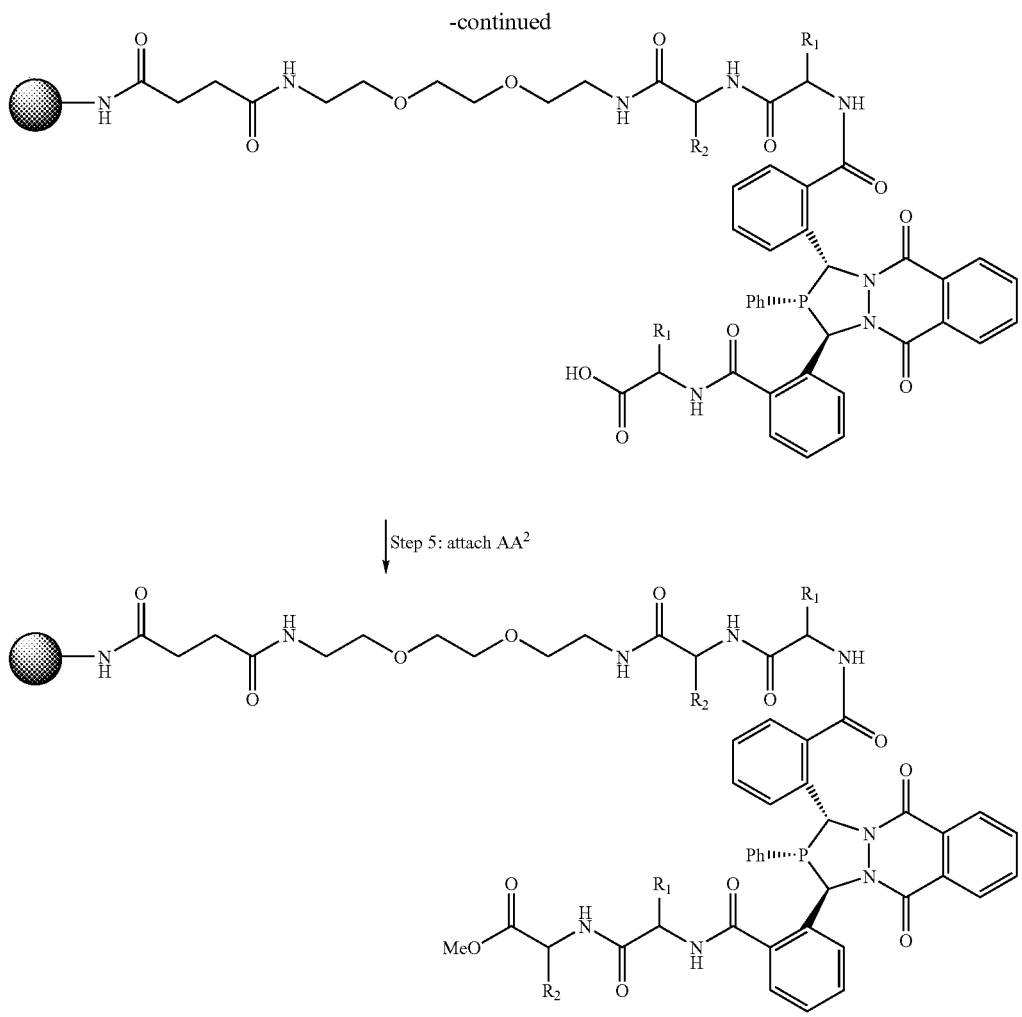

Step 1: a) 30% trifluoroacetic acid (TFA), 2% anisole; b) $CH_2Cl_2$, DMF, methanol (MeOH), DMF rinse; c) Fmoc-NH—$CHR_2$—COOH, diisopropyl carbodiimide (DIC)/1-hydroxybenzotriazole (HOBt); d) DMF, MeOH, $CH_2Cl_2$, DMF rinse. Step 2: a) 20% piperidine (2×); b) DMF, MeOH, $CH_2Cl_2$, DMF rinse; c) Fmoc-NH—$CHR_1$—COOH, DIC/HOBt; d) DMF, MeOH, $CH_2Cl_2$, DMF rinse. Step 3: a) 20% piperidine (2×); b) DMF, MeOH, $CH_2Cl_2$, DMF rinse; c) Diazaphosphacycle 2', DIC/HOBt; d) $CH_2Cl_2$ rinse. Step 4: a) HOBt, $NH_2$—$CHR_1$—COOt-Bu; b) DIEA, DIC/HOBt; c) $CH_2Cl_2$, DMF, $CH_2Cl_2$ rinse; d) 95% TFA, 2.5% $H_2O$, 2.5% triisopropylsilane (i-$Pr_3SiH$); e) $CH_2Cl_2$, DMF, $CH_2Cl_2$ rinse. Step 5: HOBt, MeO—C(O)—$CHR_2$—$NH_2$, DIEA, DIC; c) $CH_2Cl_2$, DMF, $CH_2Cl_2$ rinse. $R_1$ and $R_2$ are the amino acid side chains of $AA^1$ and $AA^2$ respectively.

Synthesis of an Immobilized Array of Diazaphosphacycles. The scheme above outlines the overall procedure for solid phase synthesis of additional amino acid functionalized phosphines, 3. Methylbenzyhydrylamine (MBHA) functionalized polystyrene resin (75 mg; 2% cross-linking; loading 1.1 mmol/g) was placed in 20 Poly-Prep Chromatography Columns (Bio-Rad), swelled in 8 mL DMF for 1 hour, and neutralized with 1 mL DIEA in 20 mL DMF, followed by rinsings. Each coupling step (including coupling of the linker, amino acids, and diazaphosphacyle) was performed in parallel using the DIC/HOBt coupling protocol in 1:4 DMF/DCM and the reactions were mixed overnight on a shaker. All reactants were added in large excess relative to the immobilized material (5-6 equivalents). The resins were isolated after each coupling cycle by thorough washings with DMF, $CH_2Cl_2$, and MeOH. The diazaphosphacycle 2', prepared as disclosed above, was used as the core phosphacycle. Coupling of 2' was performed under nitrogen. Removal of the Fmoc protecting group was effected by adding 20% piperidine in DMF solutions to the resins and mixing for 30 minutes. The Boc and t-butyl ester protecting groups were removed by treatment with TFA. A t-butyl cation scavenger cocktail of 2.5% triisopropylsilane and 2.5% water was also used during the ester deprotection. MAS-NMR characterization of products indicated that scavengers are necessary to minimize the appearance of additional phosphine-containing impurities as identified by $^{31}P$ NMR. The final products exhibit little oxygen sensitivity; $^{31}P$ NMR spectroscopy revealed that moderate exclusion of oxygen during the coupling steps involving the diazaphospohlane prevents oxidation of the phosphorous.

A 3×7 array of tetrapeptide diazaphosphacycles (resin-linker-$AA_2$-$AA_1$-diazaphosphacycle-$AA_1$-$AA_2$) was designed and synthesized. Three simple apolar residues, alanine, leucine, and valine, were installed in the positions ($AA_1$) adjacent to the diazaphosphacycle, 3. Seven different amino acids of varying bulk and functionality were attached in the $AA_2$ position. However, the array contained only 20 members because the Ala-Phe combination was not synthesized. Couplings were carried out as shown in the scheme above. To minimize oxidation at phosphorus of the 20-member array, each reaction involving the phosphine was prepared and sealed while inside a glove bag.

Allylic Alkylation Procedure. Methylene chloride (2.0 mL) was added to a septum sealed 3-dram vial containing [($\eta^3$-$C_3H_5$)PdCl]$_2$ (1.8 mg, 5 µmol), diazaphosphacycle (10 µmol or 15-20 mg of resin), n-tetrabutylammonium fluoride trihydrate (approx. 5 mg), and $NaPF_6$ under $N_2$. After stirring the solution at room temperature for 5 minutes, N,O-bis(trimethylsilyl)acetamide (0.70 mL, 3.0 mmol), dimethyl malonate (0.30 mL, 3.0 mmol), and 1,3-dimethylallyl acetate (0.15 mL, 1.0 mmol) were added. The mixture was stirred for 17 hours at room temperature. The products were diluted with 6 mL of 5:1 hexane/ethyl acetate and filtered twice through plugs of silica. The enantiomeric excess of the product was determined by chiral GC (Supelco β-DEX 120 column, 30 cm×0.25 mm ID, column temp 70° C., flow rate 1.8 mL/min). The absolute configuration of products was determined by comparison of GC retention times with results obtained previously[3c].

As a first example of the synthesis and use of inventive compounds on solid phase, PS-linker-Ala-diazaphosphacycle 3-Ala was tested. Asymetric allylic aklylation of dimethylallyl acetate with dimethylmalonate in the presence of 0.5 mole percent [Pd(allyl)Cl]$_2$, ca. 1 mole percent immobilized PS-linker-Ala-3-Ala, BSA (N,O-bis(trimethylsilyl)acetamide), sodium hexafluorophosphate, and tetrabutylammonium fluoride in dichloromethane solution at room temperature for 17 hours gives the alkylated allyl in 92% enantiomeric excess and 67% yield. Importantly, the immobilized monophosphine matched the enantioselectivity previously demonstrated for its homogeneous counterpart (93%).

Figure 22:
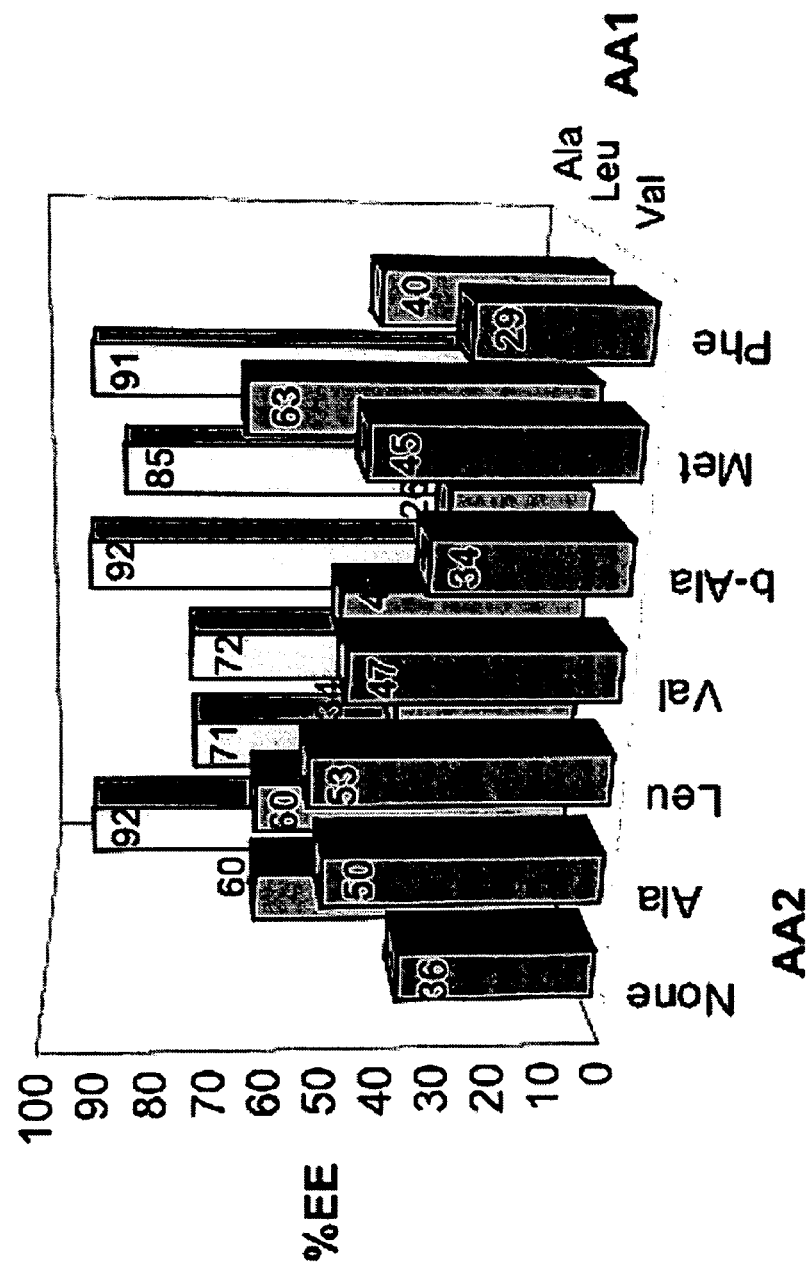
FIG. 22 is a three dimensional graph showing the enantioselectivities for Pd-catalyzed allylic alkylation of dimethyl malonate with 1,3-dimethylallyl acetate using AA$^2$-AA$^1$-diazophospholane 3-AA$^1$-AA$^2$ bound to a polystyrene resin. Details of the reaction are provided in the experimental

As a second example, a small library of PS-linker-$AA^1$-$AA^2$-3-$AA^1$-AA compounds was made and tested in the allylic alkylation as above. FIG. 22 displays the enantioselectivities obtained using resin-bound ligands of the library for asymmetric Allylic Alkylation. All products have the S configuration. As expected, the impact of the second amino acid ($AA_2$) was less than the impact of the first amino acid ($AA_1$). With alanine at $AA_1$, the best selectivities were obtained with either methionine or valine at $AA_2$.

Soluble versions of three of the phosphines from the above screen were synthesized according to procedures given above and compared to their solid phase counterparts: Ala-Met, Ala-Ala, and Val-Ala. Overall, activities on the polymer support resin of catalysts formed therein appear to be lower than solution activities by factors of 1.5 to 4. However, enantioselectivities were comparable between solid-phase and solution phase reactions.

All references cited herein are specifically incorporated by reference into the disclosure of this application.

It is understood that the invention is not limited to the embodiments set forth herein for illustration, but embraces all such forms thereof as come within the scope of the claims.

What is claimed is:

1. A diazaphosphacycle having the formula XI and salts of the diazaphosphacycle:

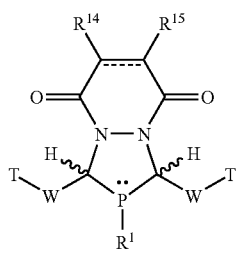

XI wherein
W, at each occurrence, is independently selected from the group consisting of aryl, cycloalkyl, and heterocyclyl groups wherein W optionally consists of one or more substituents in addition to T;
T, at each occurrence is independently selected from the group consisting of —C(O)—$OR^{16}$, —C(O)—$NR^{17}R^{18}$, —C(O)—N($R^{17}$)$OR^{18}$, substituted and unsubstituted oxazole, substituted and unsubstituted oxazoline, and substituted and unsubstituted oxazolidine groups;
$R^1$ is selected from the group consisting of substituted and unsubstituted aryl, substituted and unsubstituted alkyl, substituted and unsubstituted alkenyl, substituted and unsubstituted cycloalkyl, and substituted and unsubstituted ferrocenyl groups;
$R^{14}$ and $R^{15}$ are independently selected from the group consisting of —H, substituted and unsubstituted alkyl, substituted and unsubstituted cycloalkyl, and substituted and unsubstituted aryl; or $R^{14}$ and $R^{15}$ may join together to form a substituted or unsubstituted aryl, a substituted or unsubstituted cycloalkyl, or a substituted or unsubstituted cycloalkenyl group;
$R^{16}$, $R^{17}$ and $R^{18}$ are each independently selected from the group consisting of —H, and substituted and unsubstituted alkyl, substituted and unsubstituted aryl, substituted and unsubstituted aralkyl, substituted and unsubstituted heterocyclyl, substituted and unsubstituted heterocyclylalkyl groups; or $R^{17}$ and $R^{18}$ may join together to form a non-aromatic heterocyclyl group; and
the dashed line represents a single or double carbon-carbon bond.

2. The diazaphosphacycle of claim 1, wherein $R^{14}$ and $R^{15}$ join together to form a substituted or unsubstituted aryl group.

3. The diazaphosphacycle of claim 1, wherein $R^{14}$ and $R^{15}$ join together to form a substituted or unsubstituted cycloalkyl or a substituted or unsubstituted cycloalkenyl group.

4. The diazaphosphacycle of claim 1, wherein W at each occurrence is independently an aryl group.

5. The diazaphosphacycle of claim 1, wherein W at each occurrence is independently a phenyl group.

6. The diazaphosphacycle of claim 1, wherein T is —C(O)—$OR^{16}$.

7. The diazaphosphacycle of claim 1, wherein T is —C(O)—OH.

8. The diazaphosphacycle of claim 1, wherein T is —C(O)—$NR^{17}R^{18}$.

9. The diazaphosphacycle of claim 8, wherein $R^{17}$ is —H.

10. The diazaphosphacycle of claim 1, wherein T is 2,5-dihydro-oxazole.

11. The diazaphosphacycle of claim 1, wherein T, at each occurrence, is the same.

12. The diazaphosphacycle of claim 1, wherein the diazaphosphacycle has the formula XII:

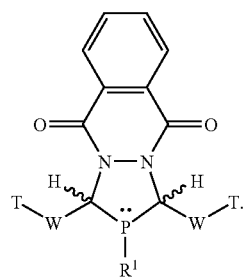

XII

13. The diazaphosphacycle of claim 1, having the formula XIII:

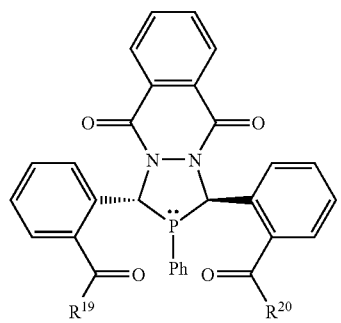

wherein $R^{19}$ and $R^{20}$ are independently selected from the group consisting of substituted and unsubstituted alkyl amine, substituted and unsubstituted aralkyl amine, substituted and unsubstituted N-containing heterocyclyl groups, protected and unprotected amino acids, protected and unprotected amino acid esters, and protected and unprotected dipeptides; and wherein $R^{19}$ and $R^{20}$ are attached to the rest of the compound of Formula XIII through a nitrogen atom.

14. The diazaphosphacycle of claim 13, wherein $R^{19}$ and $R^{20}$ are independently selected from the group consisting of

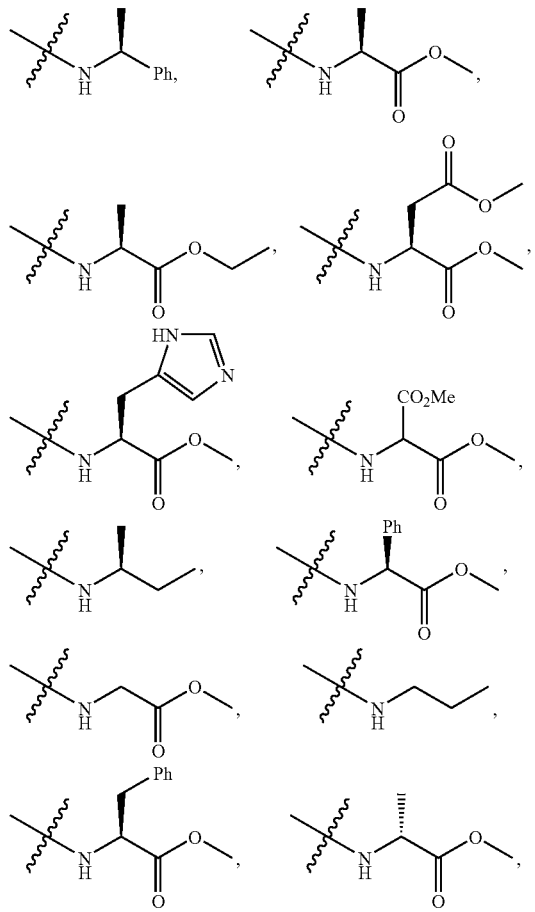

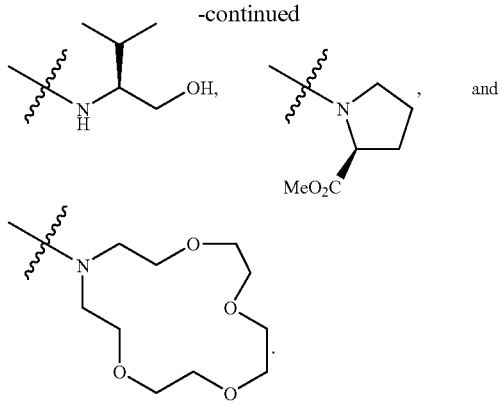

15. The diazaphosphacycle of claim 13, wherein $R^{19}$ and $R^{20}$ are independently selected from the group consisting of

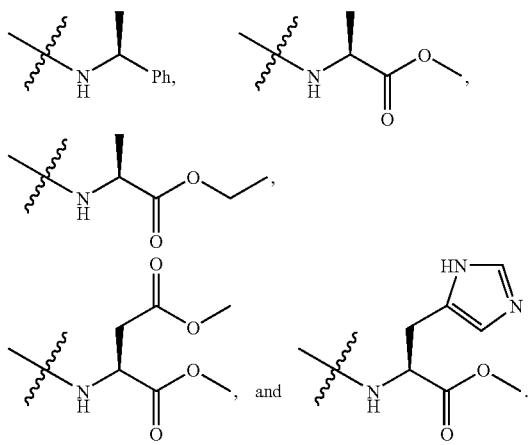

16. The diazaphosphacycle of claim 13, wherein $R^{19}$ and $R^{20}$ are the same.

17. The diazaphosphacycle of claim 13, wherein $R^{19}$ and $R^{20}$ are independently selected from the group consisting of protected or unprotected dipeptides.

18. The diazaphosphacycle of claim 17, wherein the dipeptide is a protected or unprotected Ala-Ala, Ala-Val, or Ala-Met group.

19. The diazaphosphacycle of claim 12 having the formula XIV

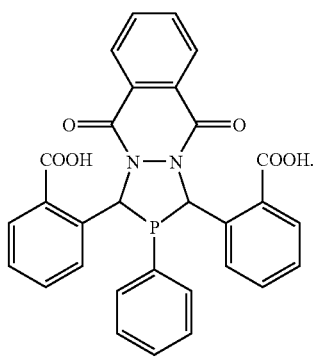

20. The diazaphosphacycle of claim 1, having the formula XIA or XIB, or a mixture thereof:

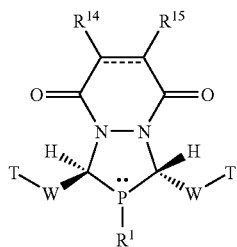

XIA

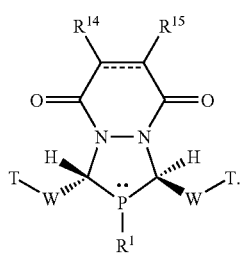

XIB

21. The diazaphosphacycle of claim 20 wherein the mixture contains XIA and XIB in a proportion of at least 80% XIA and 20% XIB or contains XIB and XIA in a proportion of at least 80% XIB and 20% XIA.

22. The diazaphosphacycle of claim 21 wherein the mixture contains XIA and XIB in a proportion of at least 90% XIA and 10% MB or contains XIB and XIA in a proportion of at least 90% XIB and 10% XIA.

23. The diazaphosphacycle of claim 21 wherein the mixture contains XIA and XIB in a proportion of at least 95% XIA and 5% XIB or contains XIB and XIA in a proportion of at least 95% XIB and 5% XIA.

24. The diazaphosphacycle of claim 21 wherein the compounds of formula XIA and XIB have the formulas XIVA and XIVB, respectively:

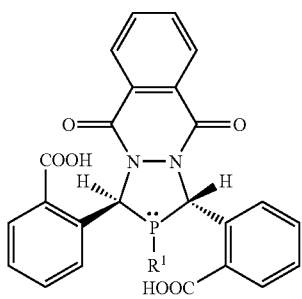

XIVA

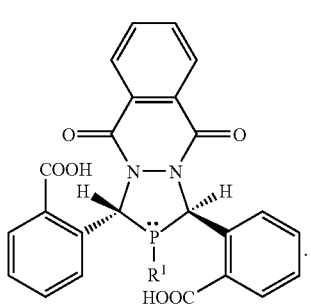

XIVB

25. The diazaphosphacycle of claim 1, having the formula XIC:

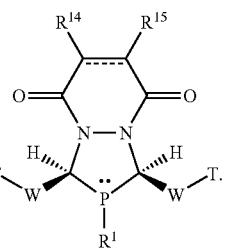

XIC

26. A library of compounds comprising at least one diazaphosphacycle of claim 1.

27. A transition metal complex, comprising the diazaphosphacycle of claim 1 and a transition metal, wherein the phosphorus atom of the diazaphosphacycle is bonded to the transition metal.

28. The transition metal complex of claim 27, wherein the transition metal is selected from the group consisting of Rh, Ru, Pd, Pt, Ir, Ni, Co, and Fe.

29. The transition metal complex of claim 27, wherein the transition metal is Pd or Rh.

30. The transition metal complex of claim 27, wherein the transition metal complex has catalytic activity.

31. A method comprising catalyzing a chemical reaction susceptible to catalysis by a transition metal using the transition metal complex of claim 28 as a catalyst.

32. A composition comprising the diazaphosphacycle of claim 1 and a solid support, wherein the diazaphosphacycle is covalently attached to the solid support.

33. The composition of claim 32 wherein the solid support is a polymeric support resin, controlled pore glass, silica, alumina, or zeolite.

34. The composition of claim 32, wherein the solid support is a polymeric support resin.

35. The composition of claim 34, wherein the polymeric support resin is a polystyrene, polyethylene glycol, or polysaccharide.

36. The composition of claim 32, wherein the diazaphosphacycle is covalently attached to the solid support at T.

37. The composition of claim 32, wherein the covalent attachment comprises a linker.

38. The composition of claim 37, wherein the linker comprises 2,2'-(ethylenedioxy)bis(ethylamino)-monosuccinamide.

39. A library of compounds comprising at least one diazaphosphacycle of claim 32.

40. A method of resolving the diazaphosphacycle of claim 1 wherein T at each occurrence is —COOH, the method comprising selectively crystallizing a mixture of the diazaphosphacycle of claim 1, wherein T at each occurrence is —COOH, with either (S)- or (R)-methylbenzylamine.

41. The method of claim 40 wherein W at each occurrence is phenyl.

42. The diazaphosphacycle of claim 1, wherein the diazaphosphacycle has the formula XV

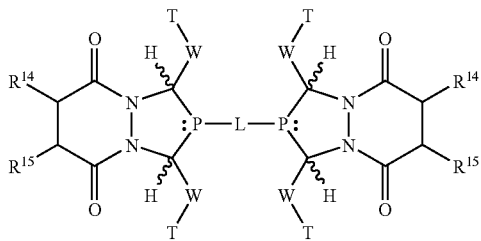

XV wherein L is a linking group selected from the group consisting of substituted and unsubstituted alkyl groups, substituted and unsubstituted alkenyl groups, substituted and unsubstituted aryl groups, and substituted and unsubstituted ferrocenyl groups.

43. The diazaphosphacycle of claim 42, wherein L is selected from the group consisting of ethane, ethylene, propane, benzene, anthracene, 9,10-dihydroanthracene, xanthene, and ferrocene groups.

44. A transition metal complex, comprising the diazaphosphacycle of claim 42 and a transition metal, wherein the phosphorous atoms of the diazaphosphacycle are bonded to the transition metal.

* * * * *

UNITED STATES PATENT AND TRADEMARK OFFICE
CERTIFICATE OF CORRECTION

| | | |
|---|---|---|
| PATENT NO. | : 7,507,820 B2 | Page 1 of 1 |
| APPLICATION NO. | : 10/914048 | |
| DATED | : March 24, 2009 | |
| INVENTOR(S) | : Landis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1034 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,507,820 B2 | Page 1 of 1 |
| APPLICATION NO. | : 10/914048 | |
| DATED | : March 24, 2009 | |
| INVENTOR(S) | : Clark R. Landis et al. | |

It is certified that error appears in the above-identified patent and that said Letters Patent is hereby corrected as shown below:

This certificate supersedes the Certificate of Correction issued September 21, 2010. The Certificate of Correction included change to patent term adjustment "by 1,034 days" which is corrected by decision dated March 2, 2011 changing the patent term adjustment to be extended or adjusted "by 1,165 days". The [*] Notice should read as follows:
--Subject to any disclaimer, the term of this patent is extended or adjusted under 35 U.S.C. 154(b) by 1,165 days.--

Signed and Sealed this
Twenty-sixth Day of April, 2011

David J. Kappos
*Director of the United States Patent and Trademark Office*